United States Patent
Du et al.

(10) Patent No.: US 10,782,297 B2
(45) Date of Patent: Sep. 22, 2020

(54) COMPOSITIONS AND METHODS FOR DIAGNOSING LUNG CANCERS

(71) Applicant: Indiana University Research and Technology Corporation, Indianapolis, IN (US)

(72) Inventors: Hong Du, Carmel, IN (US); Cong Yan, Carmel, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 14/785,067

(22) PCT Filed: Apr. 16, 2014

(86) PCT No.: PCT/US2014/034343
§ 371 (c)(1),
(2) Date: Oct. 16, 2015

(87) PCT Pub. No.: WO2014/172447
PCT Pub. Date: Oct. 23, 2014

(65) Prior Publication Data
US 2016/0077095 A1    Mar. 17, 2016

Related U.S. Application Data

(60) Provisional application No. 61/812,371, filed on Apr. 16, 2013.

(51) Int. Cl.
*G01N 1/00* (2006.01)
*G01N 33/574* (2006.01)

(52) U.S. Cl.
CPC .............. *G01N 33/57423* (2013.01)

(58) Field of Classification Search
CPC ............ G01N 33/57423; G01N 1/00
USPC ....................................... 435/7.23
See application file for complete search history.

(56) References Cited

U.S. PATENT DOCUMENTS

| | | | |
|---|---|---|---|
| 2009/0016967 A1* | 1/2009 | Schnapp | A61K 9/0043 424/43 |
| 2009/0068685 A1 | 3/2009 | Streeper et al. | |
| 2009/0104605 A1* | 4/2009 | Siuzdak | C12Q 1/6883 435/6.18 |
| 2010/0248271 A1 | 9/2010 | Miron et al. | |
| 2011/0082089 A1 | 7/2011 | Borlak et al. | |
| 2011/0195478 A1* | 8/2011 | Chen | C07K 14/47 435/188 |
| 2013/0052665 A1* | 2/2013 | Ling | G01N 33/6893 435/7.92 |

FOREIGN PATENT DOCUMENTS

| WO | WO 2009/108073 A1 * | 9/2009 |
|---|---|---|
| WO | WO2012031008 A2 | 3/2012 |
| WO | WO2012115885 A1 | 8/2012 |

OTHER PUBLICATIONS

Liu et al (Cancer Sci, 2007, 98(10): 1617-1624).*
Ueda et al (PLOS One, 2011, 6(4): 1-12).*
Knight et al (SHOCK, 2004, 21(1): 26-30).*
Etzioni et al (Nature Reviews, Apr. 2003, 3: internet pp. 1-10).*
Mercer (Immunol Ser, 1990, 53:39-54).*
The 1988 Stratagene catalog (3 pages).*
Chang et al (Am J Respir Crit Care Med, 2008, 178: 701-709).*
Milan et al (Journal of Proteomics, 2012, 76: 91-101).*
International Search Report and Written Opinion issued by the ISA/US, Commission for Patents, dated Sep. 12, 2014, for International Application No. PCT/US2014/034343; 20 pages.
International Preliminary Report on Patentability issued by The International Bureau of WIPO, dated Oct. 20, 2015, for International Application No. PCT/US2014/034343; 17 pages.
Li, Yuan, et al. "Activation of the Signal Transducers and Activators of the Transcription 3 Pathway in Alveolar Epithelial Cells induces Inflammation and Adenocarcinomas in Mouse Lung", Cancer Res 2007; vol. 67, No. 18, Sep. 15, 2007; pp. 8494-8503.
Qu, Peng, et al. "Stat3 Downstream Genes Serve as Biomarkers in Human Lung Carcinomas and Chronic Obstructive Pulmonary Disease", Lung Cancer, vol. 63, No. 3, Mar. 2009; 16 pages.
Qu, Peng, et al. "Myeloid-specific Expression of Api6/AIM/Spα Induces Systemic Inflammation and Adenocarcinoma in the Lung", J Immunol., vol. 182, No. 3, Feb. 1, 2009; 34 pages.
Qu, Peng, et al. "Matrix-metalloproteinase 12 Overexpression in Lung Epithelial Cells Plays a Key Role in Emphysema to Lung Brochioalveolar Adenocarcinoma Transition", Sep. 15, 2010; 21 pages.

* cited by examiner

*Primary Examiner* — Sean E Aeder
(74) *Attorney, Agent, or Firm* — Eric J. Kraus

(57) ABSTRACT

The present invention provides diagnostics for identifying and distinguishing various types of lung cancers using serum and/or bronchioalveolar lavage fluid. Signatures of secretory proteins are used to identify and distinguish lung cancers. The biomarker signatures may also be used to separate lung cancers from other inflammatory diseases, monitor progression, or assess treatment efficacy.

9 Claims, 42 Drawing Sheets

Data from Human: Serum

COMPOSITIONS AND METHODS FOR DIAGNOSING LUNG CANCERS

CROSS REFERENCE TO RELATED APPLICATIONS

This application claims the benefit of International Application No. PCT/US2014/034343, filed Apr. 14, 2014, which claims priority from U.S. Provisional Application No. 61/812,371, filed Apr. 16, 2013, the entire disclosures of which are incorporated by reference herein for all purposes.

STATEMENT REGARDING FEDERALLY SPONSORED RESEARCH

This invention was made with government support under CA138759 awarded by the National Institutes of Health. The Government has certain rights in the invention.

BACKGROUND OF THE INVENTION

Lung cancer is one of the biggest public health challenges in the world. Although incidence rates have been stabilized, more than 170,000 new cases of lung cancer are diagnosed each year in the United States, and it will continue to be the most common cause of cancer death among adults, with more than 163,000 people succumbing to the disease each year. According to the World Health Organization, more than 1.37 million people die from lung cancer each year worldwide. Furthermore, lung cancer is a difficult disease to detect in its early stages. In most cases, the tumors are detected at advanced stages and the overall 5-year survival rate is approximately 15%. Thus, it is essential to understand the events that initiate lung carcinogenesis and find strategies for identifying and distinguishing amongst lung cancers.

In particular, there is a need to identify soluble and secretory proteins as biomarkers in serum or bronchioalveolar lavage fluid (BALF) samples for lung cancer prediction and verification. The present invention provides signatures of secretory proteins for lung cancer prediction in mammals.

SUMMARY OF THE INVENTION

The present invention provides diagnostics for identifying, characterizing, and distinguishing various types of lung cancers. Signatures of secretory proteins are used to identify and distinguish lung cancers. Also provided are such methods using serum and/or bronchioalveolar lavage fluid.

Embodiments of the present invention provide methods to diagnose lung cancer in a human, comprising: a.) obtaining a blood onchioalveolar lavage fluid sample from a human; b) conducting an assay of the blood or bronchioalveolar lavage fluid sample so as to identify at least two lung cancer-associated secreted proteins in the sample, wherein the at least two lung cancer-associated secreted proteins are selected from the group consisting of: chitinase 3-like 1 (CHI3L1); transthyretin (TTR); fibrinogen beta polypeptide (FGb); guanylate cyclase activator 2A (GUCA2A); and fibrinogen alpha polypeptide (Fga); c.) diagnosing lung cancer in a human in the event that at least two lung-cancer associated secreted proteins are identified in the blood or bronchioalveolar lavage fluid sample.

Embodiments of the invention provide methods to diagnose lung cancer in a human, comprising: a.) obtaining a blood or bronchioalveolar lavage fluid sample from a human; b.) conducting an assay of the blood or bronchioalveolar lavage fluid sample so as to identify at least five lung cancer-associated secreted proteins in the sample, wherein the at least five lung cancer-associated secreted proteins are selected from the group consisting of: chitinase 3-like 1 (CHI3L1); transthyretin (TTR); fibrinogen beta polypeptide (FGb); fibrinogen-like protein 1 (FGL1); guanylate cyclase activator 2A (GUCA2A); delta-like 1 homolog (DLK1); glucose transporter 3 (GLUT3); cerebellin 1 (CBLN1); elastase 1, pancreatic (ELA1); fibrinogen alpha polypeptide (Fga); histidine-rich glycoprotein (HRG); sonic hedgehog homolog (SHH); transmembrane protein 27 (TMEM27); Matrix metalloproteinase 12 (MMP12); and Apoptosis inhibitor 6 (Api6); c.) diagnosing lung cancer in a human in the event that at least five lung-cancer associated secreted proteins are identified in the blood or bronchioalveolar lavage fluid sample.

Embodiments of the invention provide methods to identify a lung cancer subtype in a human, comprising:
a.) obtaining a blood or bronchioalveolar lavage fluid sample from a human;
b.) conducting an assay of the blood or bronchioalveolar lavage fluid sample so as to identify the concentration of at least transthyretin (TTR); fibrinogen beta polypeptide (FGb); and transmembrane protein 27 (TMEM27) in the sample;
c.) diagnosing adenocarcinoma lung cancer in a human in the event that the sample concentrations identified are:
TTR is greater than approximately 1002 ng/ml;
FGb is greater than approximately 53.36 ng/ml;
TMEM27 is less than approximately 11 ng/ml;
d.) diagnosing squamous cell lung cancer in a human in the event that the sample concentrations identified are:
TTR is greater than approximately 1002 ng/ml;
FGb is greater than approximately 53.36 ng/ml;
TMEM27 is greater than approximately 11 ng/ml;
e.) diagnosing small cell lung cancer in a human in the event that the sample concentrations identified are:
TTR is greater than approximately 1002 ng/ml;
FGb is less than approximately 53.36 ng/ml;
TMEM27 is not relevant;
f.) not diagnosing lung cancer in a human in the event that the sample concentrations identified are:
TTR is less than approximately 1002 ng/ml;
FGb is not relevant;
TMEM27 is not relevant.

Embodiments of the invention provide methods to identify a lung cancer subtype in a human, comprising:
a.) obtaining a blood or bronchioalveolar lavage fluid sample from a human, wherein the sample comprises at least one lung cancer cell;
b.) conducting an assay of the blood or bronchioalveolar lavage fluid sample so as to identify the concentration of at least fibrinogen beta polypeptide (FGb), afibrinogen-like protein 1 (FGL1), and transmembrane protein 27 (TMEM27) in the sample;
c.) diagnosing adenocarcinoma lung cancer in a human in the event that the sample concentrations identified are:
FGb is greater than approximately 60.81 ng/ml;
TMEM27 is less than approximately 11 ng/ml; and
FGL1 is not relevant;
d.) diagnosing squamous cell lung cancer in a human in the event that the sample concentrations identified are:
FGb is not relevant;
TMEM27 is greater than approximately 11 ng/ml; and/or
FGL1 is greater than approximately 1341 ng/ml;

e.) diagnosing small cell lung cancer in a human in the event that the sample concentrations identified are:
FGb is less than approximately 60.81 ng/ml;
TMEM27 is not relevant; and
FGL1 is less than approximately 1341 ng/ml.

Embodiments of the invention provide methods to monitor lung cancer progression comprising: a.) obtaining a first sample of blood or bronchioalveolar lavage fluid from a human patient; b.) conducting an assay of the first sample so as to measure at least three lung cancer-associated biomarkers in the sample, wherein the at least three lung cancer-associated biomarkers are proteins or mRNA selected from the group consisting of: chitinase 3-like 1 (CHI3L1); transthyretin (TTR); fibrinogen beta polypeptide (FGb); fibrinogen-like protein 1 (FGL1); guanylate cyclase activator 2A (GUCA2A); delta-like 1 homolog (DLK1); glucose transporter 3 (GLUT3); cerebellin 1 (CBLN1); elastase 1, pancreatic (ELA1); fibrinogen alpha polypeptide (Fga); histidine-rich glycoprotein (HRG); sonic hedgehog homolog (SHH); transmembrane protein 27 (TMEM27); Matrix metalloproteinase 12 (MMP12); and Apoptosis inhibitor 6 (Api6); c.) obtaining a second sample of blood or bronchioalveolar lavage fluid from the human patient, wherein the second sample is collected subsequent to the first sample; d.) conducting an assay of the second sample so as to measure at least three lung cancer-associated biomarkers, wherein at least two biomarkers correspond to biomarkers measured in the first sample; e.) comparing measurements of the corresponding biomarkers; and f.) monitoring lung cancer progression.

Also provided are such methods, wherein a first sample is collected prior to administering a treatment and a second sample is collected after administering the treatment.

Also provided are such methods, wherein periodic samples are collected and tested to monitor progression of the lung disease, wherein the characteristic of progression is selected from the group consisting of: responsiveness to treatment, prognosis, and relapse. In some embodiments periodic sampling and measurement of the biomarkers is performed once every 2-6 weeks, every 2-4 months, 2-5 times per year, weekly, monthly, or annually.

Also provided are such methods, which further comprise communicating a lung cancer diagnosis to the human. Also provided are such methods, which further comprise documenting a lung cancer assessment in a computerized database.

Also provided are such methods, which further comprise prescribing a lung cancer treatment to the human.

Also provided are such methods, which further comprise contraindicating or discontinuing a lung cancer treatment.

Also provided are such methods, which further comprise identifying at least one additional biomarker of lung cancer.

Also provided are such methods, wherein the at least one additional biomarker of lung cancer is selected from the group consisting of: chitinase 3-like 1 (CHI3L1); transthyretin (TTR); fibrinogen beta polypeptide (FGb); fibrinogen-like protein 1 (FGL1); guanylate cyclase activator 2A (GUCA2A); delta-like 1 homolog (DLK1); glucose transporter 3 (GLUT3); cerebellin 1 (CBLN1); elastase 1, pancreatic (ELA1); fibrinogen alpha polypeptide (Fga); histidine-rich glycoprotein (HRG); sonic hedgehog homolog (SHH); transmembrane protein 27 (TMEM27).

Also provided are such methods, wherein fifteen biomarkers are measured.

Also provided are such methods, wherein the sensitivity is between 60-100 percent, 70-100 percent, and 80-100 percent.

Also provided are such methods, wherein the specificity is between 60-100 percent, 70-100 percent, and 80-100 percent.

Also provided are such methods, which further distinguish lung cancer from other inflammatory diseases.

Also provided are such methods, wherein a biomarker level in a cancerous test sample is increased by 1-30 fold, 2-20 fold, 2-10 fold, or 5-15 fold relative to a non-cancerous control value. The control value may be derived from a non-cancerous sample from another human, a sample of non-cancerous tissue from the patient, a composite of non-cancerous samples, or control values recorded in a database.

Also provided are such methods, wherein said assay comprises an enzyme-linked immunosorbent (ELISA) assay.

Also provided are such methods, wherein said assay is selected from the group consisting of: ELISA; western blot; protein array; probe hybridization; gene microarray; mRNA microarray; in situ hybridization; quantitative real time polymerase chain reaction (qPCR); reverse transcription polymerase chain reaction (RT-PCR); radioimmunoassay (RIA); immunoassay; chemiluminescent assay; and microfluidic device.

Embodiments of the invention provide computer-assisted methods to generate a report of the results and/or conclusions of a method herein.

Embodiments of the invention provide compositions comprising at least two antibodies directed to secreted proteins selected from the group consisting of: chitinase 3-like 1 (CHI3L1); transthyretin (TTR); fibrinogen beta polypeptide (FGb); fibrinogen-like protein 1 (FGL1); guanylate cyclase activator 2A (GUCA2A); delta-like 1 homolog (DLK1); glucose transporter 3 (GLUT3); cerebellin 1 (CBLN1); elastase 1, pancreatic (ELA1); fibrinogen alpha polypeptide (Fga); histidine-rich glycoprotein (HRG); sonic hedgehog homolog (SHH); transmembrane protein 27 (TMEM27); Matrix metalloproteinase 12 (MMP12); and Apoptosis inhibitor 6 (Api6).

Also provided are methods of quantification of mRNA of at least two secreted protein biomarkers.

Also provided are methods wherein a level of the at least one marker is compared to a corresponding cancerous reference standard.

Embodiments of the invention provide methods for selecting a patient to undergo diagnostic imaging for lung cancer comprising: providing a sample from the patient; determining presence or level of at least one marker associated with lung cancer in the sample by laboratory assay; and selecting for diagnostic imaging patients having the at least one marker in the sample; wherein the at least one marker is selected from the group consisting of: CHI3L1, TTR, FGb, FGL1, GUCA2A, DLK1, GLUT3, CBLN1, ELA1, Fga, HRG, SHH, TMEM27, MMP12, and Api6; wherein the sample is derived from the patient's lung tissue, lymph, blood, and/or bronchoalveolar lavage fluid; and wherein the diagnostic imaging is selected from the group consisting of: chest radiograph (X-ray), positron emission tomography (PET), magnetic resonance imaging (MRI), computed tomography (CT).

Embodiments of the invention provide kits comprising a composition herein.

Embodiments of the invention provide compositions as shown and described herein.

Embodiments of the invention provide methods as shown and described herein.

Various objects and advantages of this invention will become apparent to those skilled in the art from the following detailed description, when read in light of the accompanying figures.

BRIEF DESCRIPTION OF THE FIGURES

FIG. 23. Graphic depicting marker analysis example for adenocarcinoma v. control FIG. 24. Graphic depicting marker analysis example for small cell v. control FIG. 25. Graphic depicting marker analysis example for adenocarcinoma v. control.

DETAILED DESCRIPTION OF THE INVENTION

Each cancer patient is unique, as is the tumor and the cancer. The course of the disease and the effect of therapy are a product of the genetics and the environment of both the patient and the tumor. Through tailoring treatment to the specific genetic profile of the patient and the tumor, biomarkers can be used to increase the efficacy, lessen the toxicity, and decrease the overall costs of treatments, including chemotherapy. At the cellular level, cancer is a genetic disease and progression of the tumor is associated with a progressively larger number of genetic changes, such as translocations, amplifications, deletions, and mutations. The genes involved in the cancerous process are oncogenes and tumor suppressor genes. In the cancerous process, oncogenes are activated and tumor suppressor genes are inhibited. As described herein, selected secretory biomarkers play an important role in lung cancer and are useful for lung cancer detection and characterization.

Secretory CHI3L1 plays an important role in inflammation-induced lung cancer formation and serves as a biomarker for lung cancer prediction.

Figure 1A:
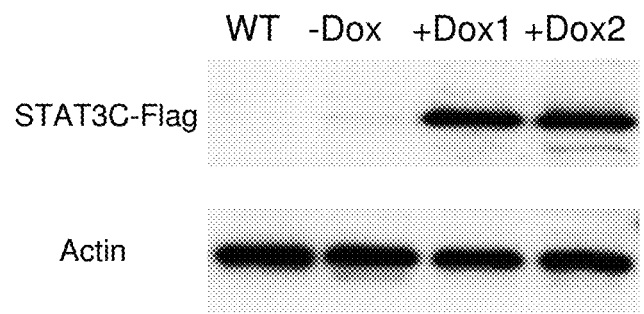
FIG. 1. Western Blot analysis of Stat3C-Flag and CHI3L1 protein in CCSP-rtTA/(TetO)$_7$-CMV-Stat3C mice. A) Expression of Stat3C-Flag in the whole lung of CCSP-rtTA/(TetO)$_7$-CMV-Stat3C double-transgenic mice. Actin was used as control. WT: wild type mouse lungs; −Dox: doxycycline untreated double transgenic mouse lungs; +Dox1 & +Dox2: doxycycline treated mouse lungs. B) Expression of CHI3L1 protein in BALF of CCSP-rtTA/(TetO)$_7$-CMV-Stat3C double-transgenic mice. Lane 1-3, doxycycline-untreated mice (Dox−); Lane 4-6, doxycycline-treated mice without showing lung tumor (Dox+); Lane 7-10, doxycycline-treated mice showing lung tumor (Lung Cancer).
Figure 1B:
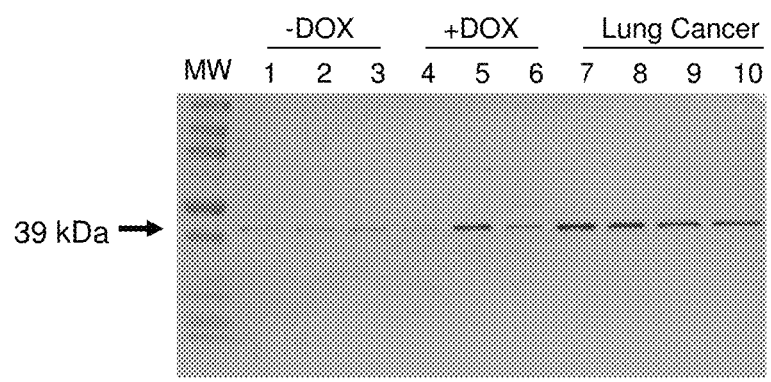
Figure 2:
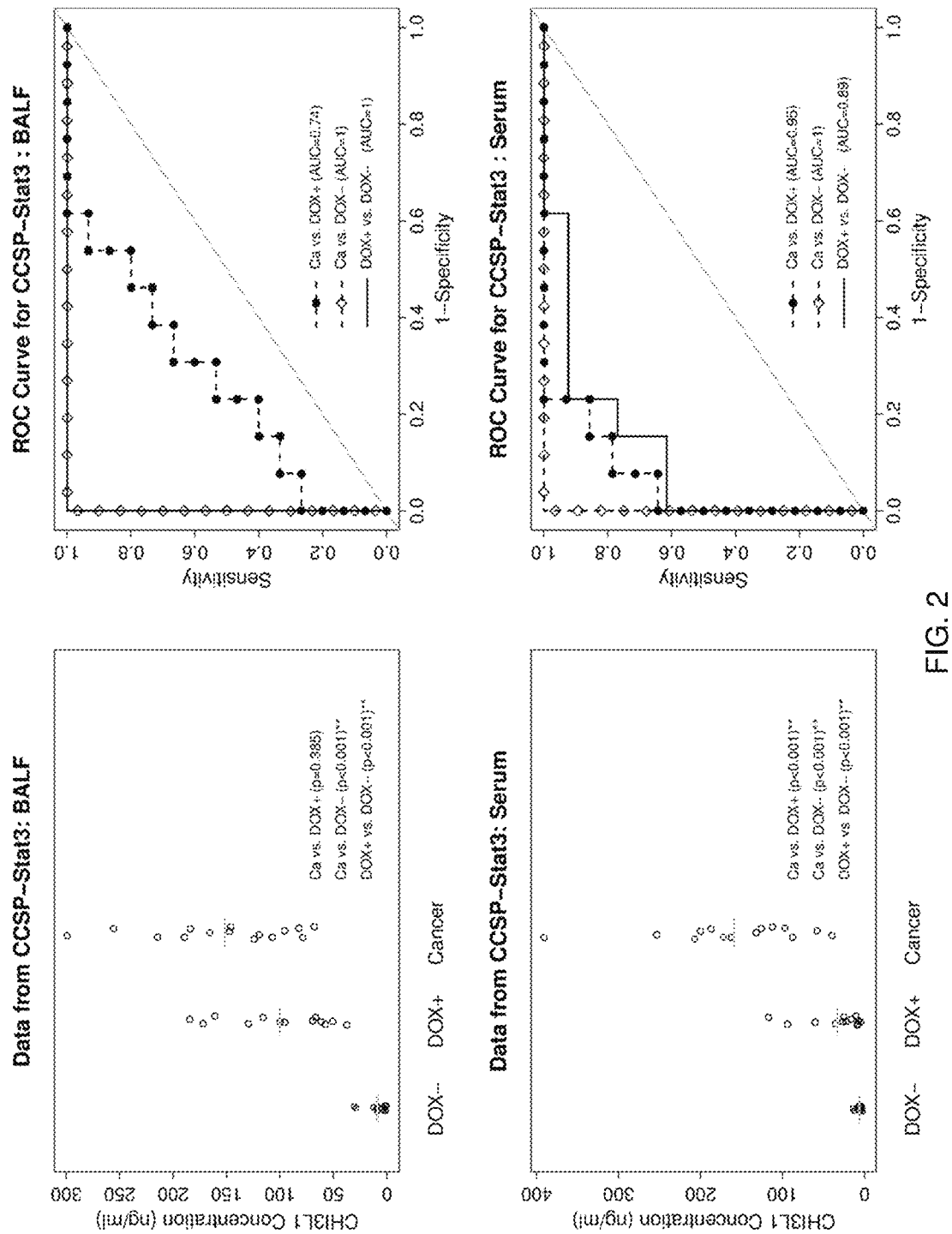
FIG. 2. ELISA analyses of CHI3L1 protein in BALF and serum of CCSP-rtTA/(TetO)$_7$-CMV-Stat3C bitransgenic mice. Left: CHI3L1 protein concentrations in BALF and serum of doxycycline-treated and untreated bitransgenic mice. Right: ROC (Receiver Operating Characteristic) curve analyses to determine the area under the curve (AUC). Dox−: doxycycline-untreated mice; Dox+: doxycycline-treated mice without showing lung tumor; Cancer, doxycycline-treated mice with lung tumor. Mean±SD in BALF (n>13), DOX−: 8.8±10.0, DOX+: 100.0±49.0, Cancer: 151.8±67.3. Mean±SD in serum (n>13), DOX−: 6.2±3.7, DOX+: 33.5±35.6, Cancer: 159.0±90.0. The gray lines represent the mean values.
Figure 5A:
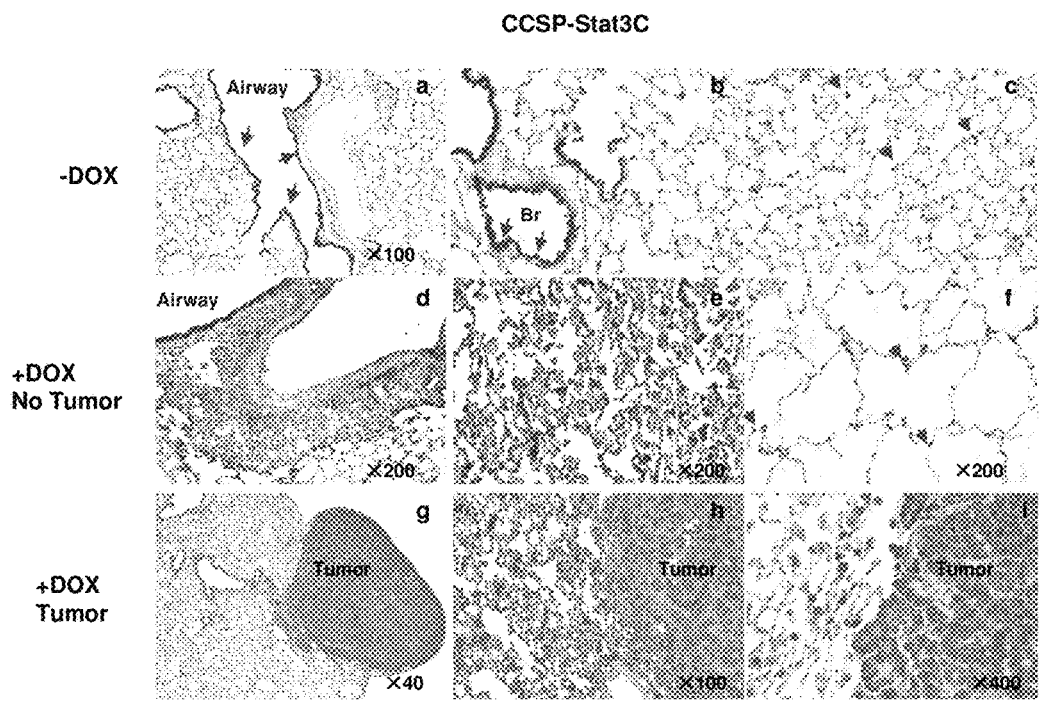
FIG. 5. Immunohistochemical staining of CHI3L1 protein in the lung of inflammation-induced tumor mice. A) Immunohistochemical staining in the lungs of doxycycline-treated or untreated CCSP-rtTA/(TetO)$_7$-CMV-Stat3C mice; B) Immunohistochemical staining of tumor regions in the lungs of doxycycline-treated CCSP-rtTA/(TetO)$_7$-CMV-MMP12 mice, c-fms-rtTA/(TetO)$_7$-CMV-MMP12 mice, and c-fms-rtTA/(TetO)$_7$-CMV-Api6 mice. −Dox: doxycycline-untreated mice; +Dox: doxycycline-treated mice.
Figure 6:
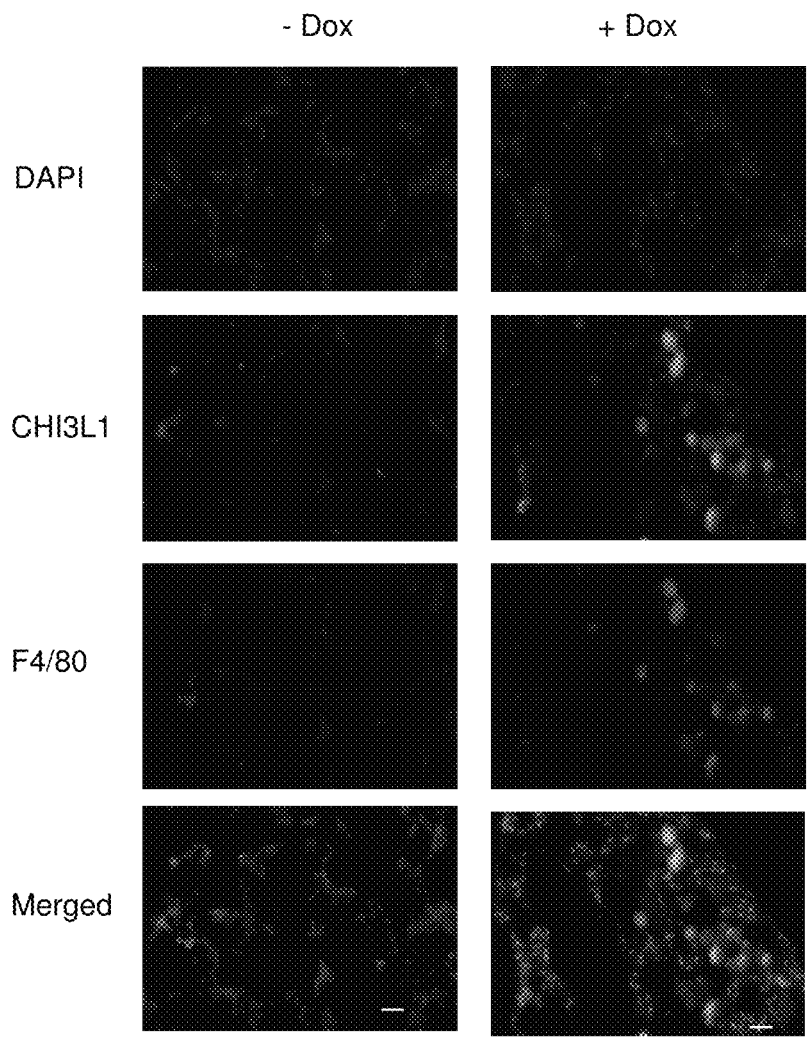
FIG. 6. Immunofluorescent co-staining of CHI3L1 and F4/80 in the lung of CCSP-rtTA/(TetO)$_7$-CMV-Stat3C mice. CCSP-rtTA/(TetO)$_7$-CMV-Stat3C bitransgenic mice were treated (+DOX) or untreated (−DOX) with doxycycline Immunofluorescent staining of lung sections was performed using anti-CHI3L1 and F4/80 antibodies. Co-localization of both staining was observed in the merged picture. Bar represents 20 μm.

CHI3L1 was first identified as a downstream gene of Stat3 in the CCSP-rtTA/(TetO)$_7$ Stat3C spontaneous lung tumor mouse model by Affymetrix GeneChip microarray. Its secretion was detectable in BALF of doxycycline-untreated mice (normal control) (FIG. 1B). Its spatial expression was restrictive to alveolar type II epithelial cells and conducting airway epithelial cells, as well as alveolar macrophages in the normal mouse lung (FIG. 5A a-c, FIG. 6). During inflammatory status, after Stat3C overexpression by doxycycline induction, the concentration of CHI3L1 was elevated in BALF of tumor-forming CCSP-rtTA/(TetO)$_7$Stat3C bitransgenic mice (FIG. 1B, lane 5, FIG. 2). This is tightly associated with strong tumor cell expression of CHI3L1 in the lung (FIG. 5A g-i). Even in the non-tumor-forming mice, CHI3L1 expression was highly induced in inflammatory cells of the lung (FIG. 5A d-e, FIG. 6). This often accompanied with emphysema (FIG. 5A f). Both tumor cells and inflammatory cells contribute to CHI3L1 protein elevation in BALF of doxycycline-treated CCSP-rtTA/(TetO)$_7$Stat3C bitransgenic mice. Interestingly, the CHI3L1 protein concentration was also elevated in the blood serum of doxycycline-treated CCSP-rtTA/(TetO)$_7$Stat3C bitransgenic mice (FIG. 2, lower panel). At least the myeloid population contributes to the increase of the CHI3L1 protein concentration in the blood of doxycycline-treated CCSP-rtTA/(TetO)$_7$Stat3C bitransgenic mice.

Increased CHI3L1 protein concentration was observed in BALF and serum of doxycycline-treated CCSP-rtTA/(TetO)$_7$-CMV-MMP12 and CCSP-rtTA/(TetO)$_7$-CMV-Api6 bitransgenic mice with tumor. No increase of the CHI3L1 protein concentration was observed in non-tumor mice even after doxycycline treatment (FIG. 3). The study was also repeated in two systemic inflammation-induced tumor models (FIG. 4), in which MMP12 and Api6 were overexpressed in myeloid cells of c-fms-rtTA/(TetO)$_7$-CMV-MMP12 and c-fms-rtTA/(TetO)$_7$-CMV-Api6 bitransgenic mice. Stat3 was activated in lung epithelial cells of both systemic inflammation-induced tumor models. Based on these studies in multiple inflammation-induced lung tumor mouse models, it is shown that Stat3 and its downstream genes are involved in lung tumorigenesis. The products of these genes can serve as biomarkers for lung cancer prediction and verification.

Figure 7A:
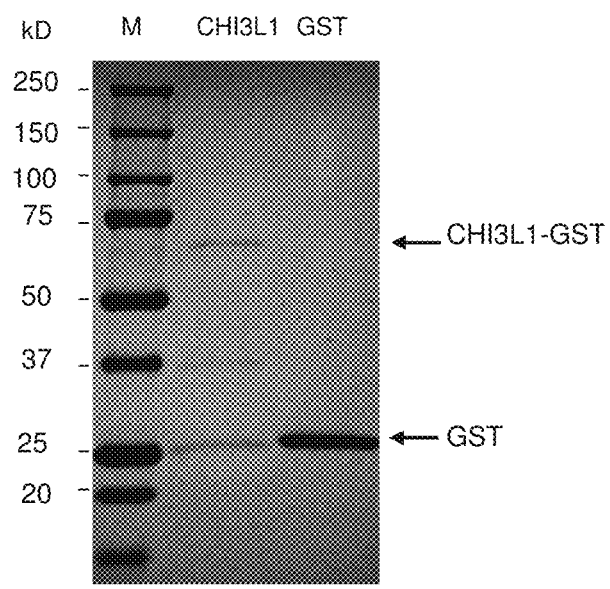
FIG. 7. Stimulatory effect of CHI3L1 on tumor cells in vitro. A) Purity of recombinant CHI3L1-Flag fusion protein (upper arrow); B) LLC cell proliferation treated with GST or CHI3L1-GST fusion protein; C) The apoptotic activity of LLC cells treated with GST or CHI3L1-GST fusion protein by Annexin V labeling assay. *, p<0.05, **, P<0.01.
Figure 7B:
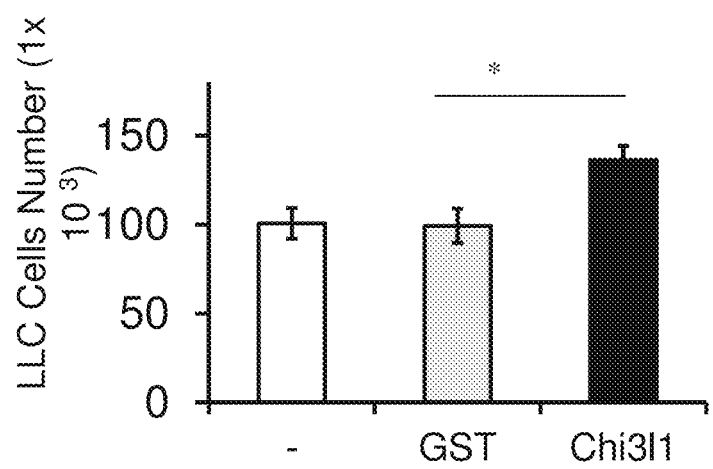
Figure 7C:
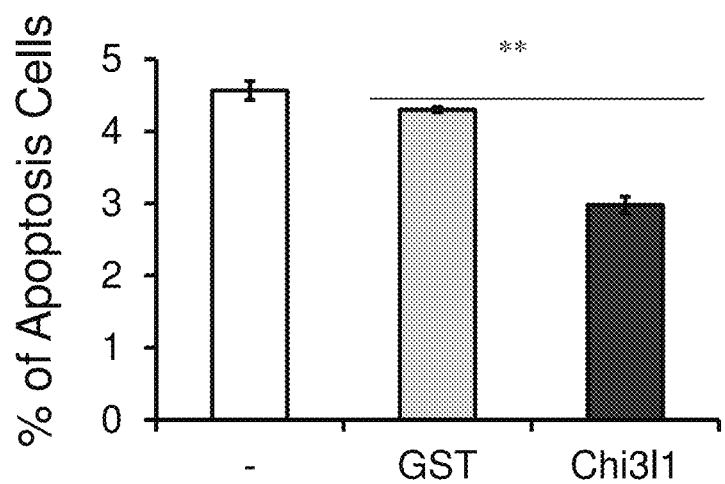
Figure 8A:
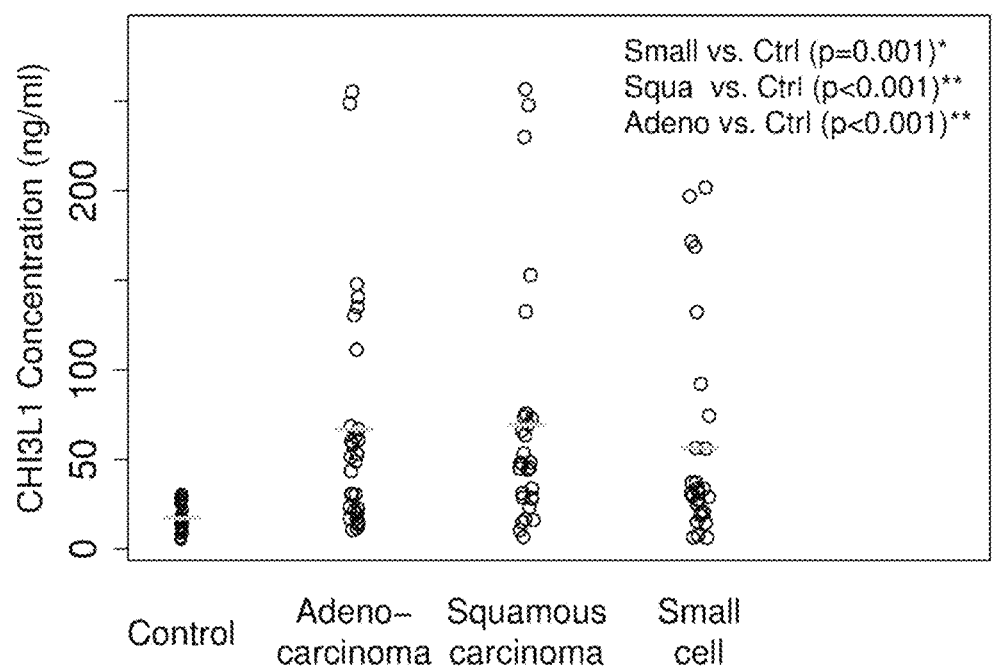
FIG. 8. ELISA analysis of CHI3L1 protein in serum of human lung cancer patients. Top: CHI3L1 protein concentrations in human serum. Bottom: ROC (Receiver Operating Characteristic) curve analysis to determine the area under the curve (AUC). Mean±SD in control (n>30): 17.3±7.8. Mean±SD in adenocarcinoma (n>30): 66.9±64.8. Mean±SD in squamous carcinoma (n>30): 69.3±69.0. Mean±SD in small cell cancer (n>30): 56.3±58.8. The gray lines represent the mean values. Control: Normal human without cancer.
Figure 8B:
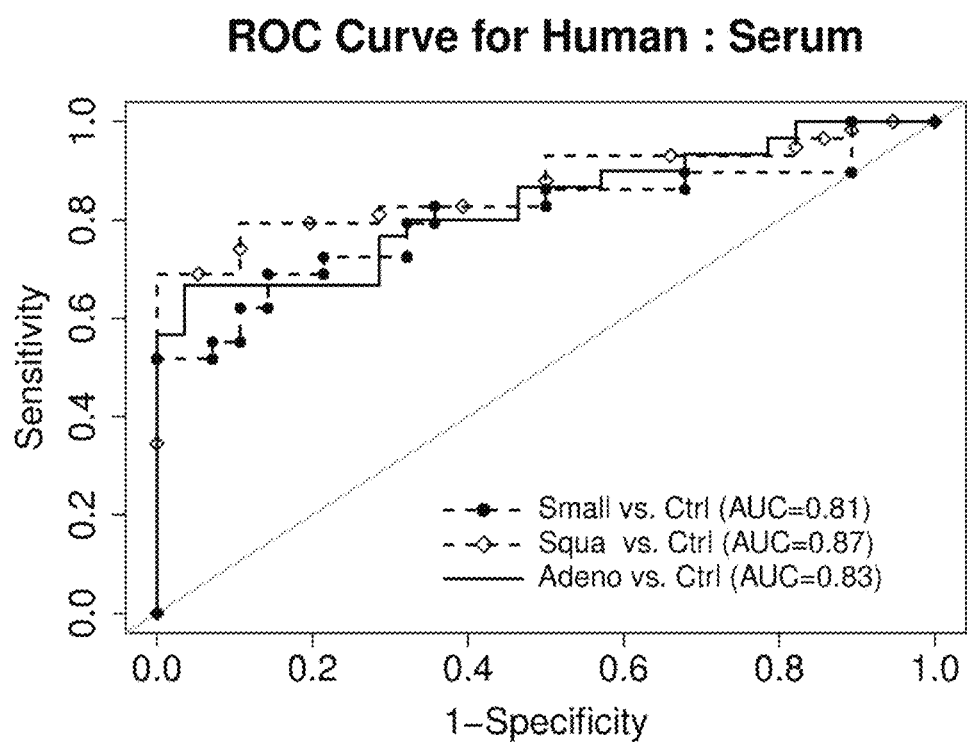
Figure 9A:
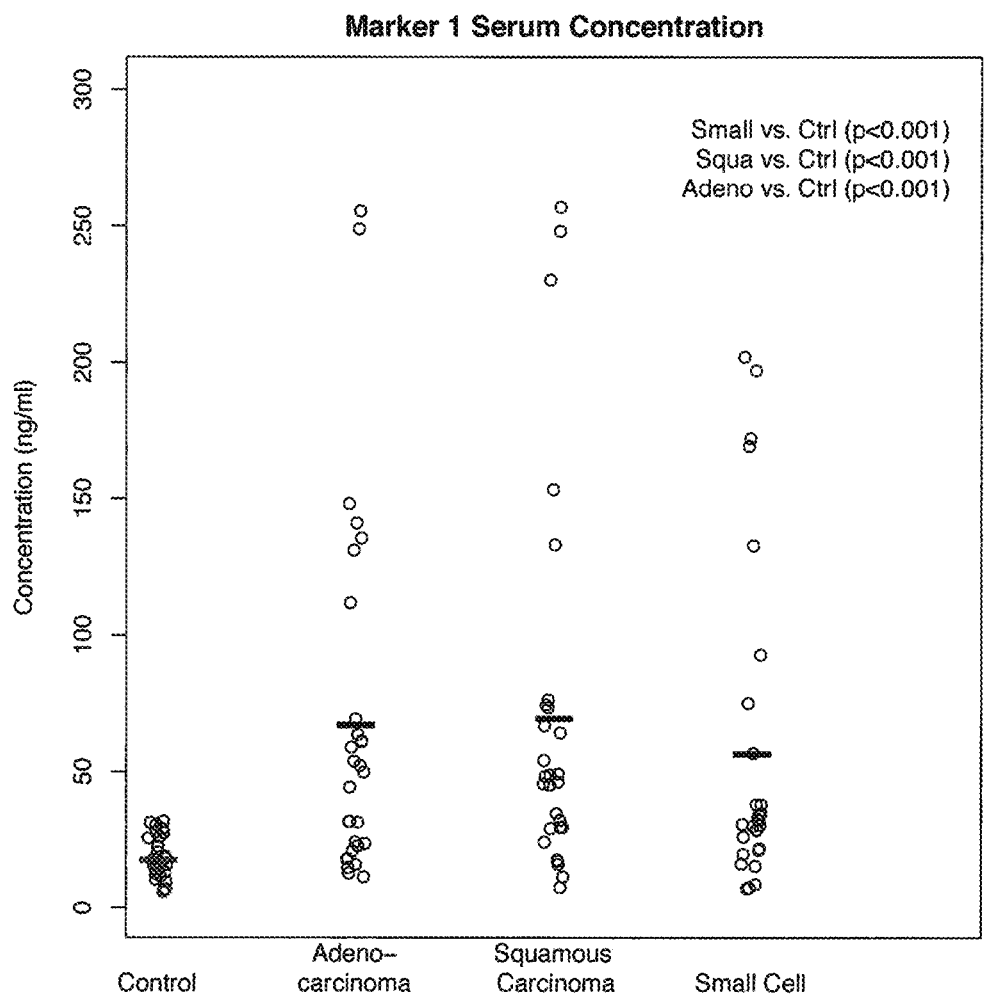
FIG. 9. (A) Marker 1 Serum Concentration by cell type; (B) ROC Curves: Marker 1
Figure 9B:
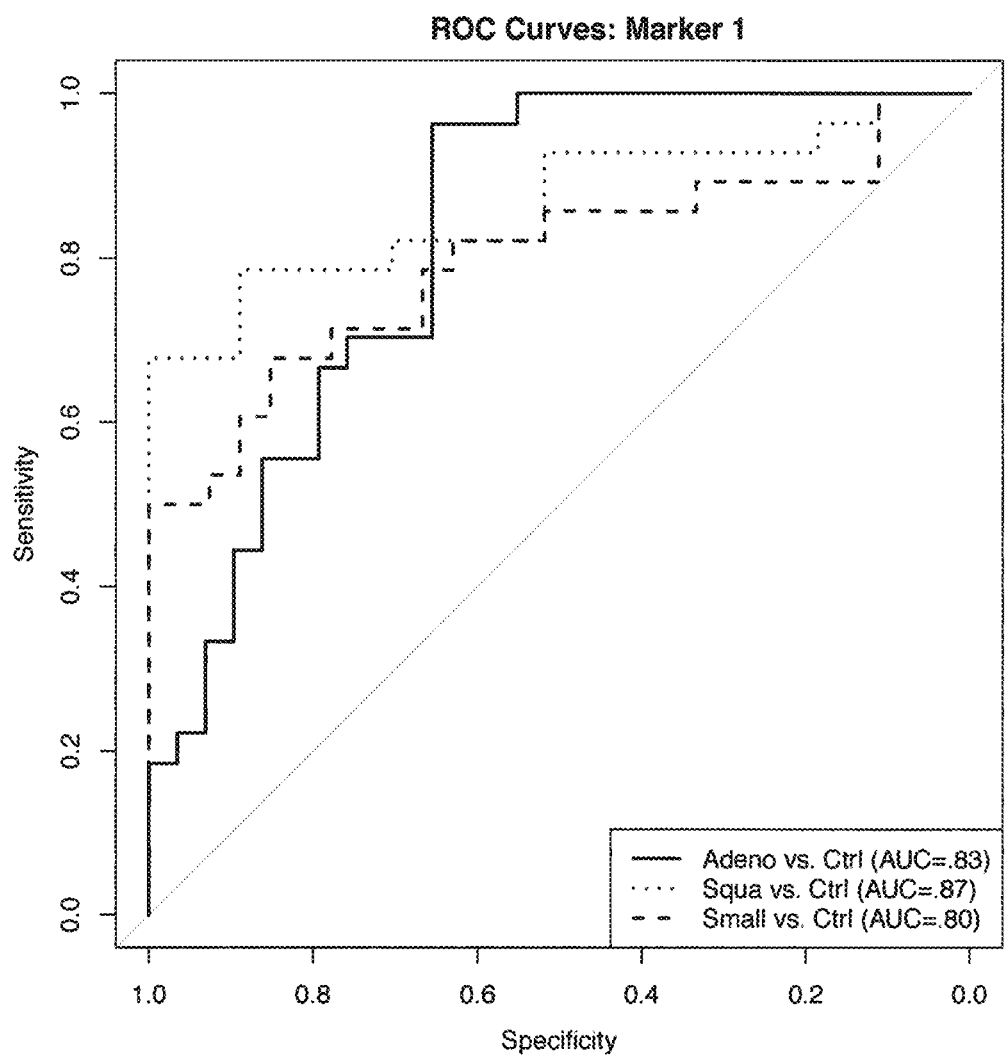
Figure 10A:
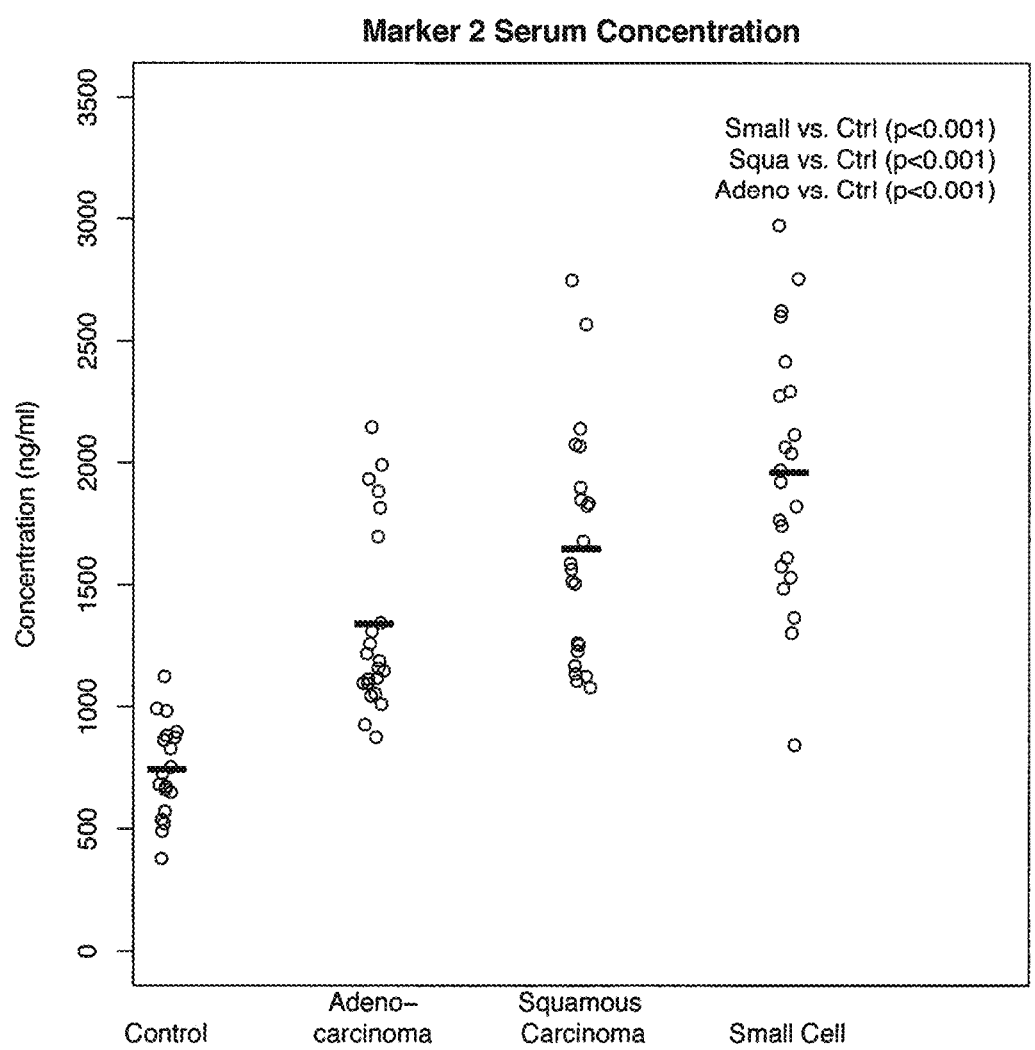
FIG. 10. (A) Marker 2 Serum Concentration by cell type; (B) ROC Curves: Marker 2
Figure 10B:
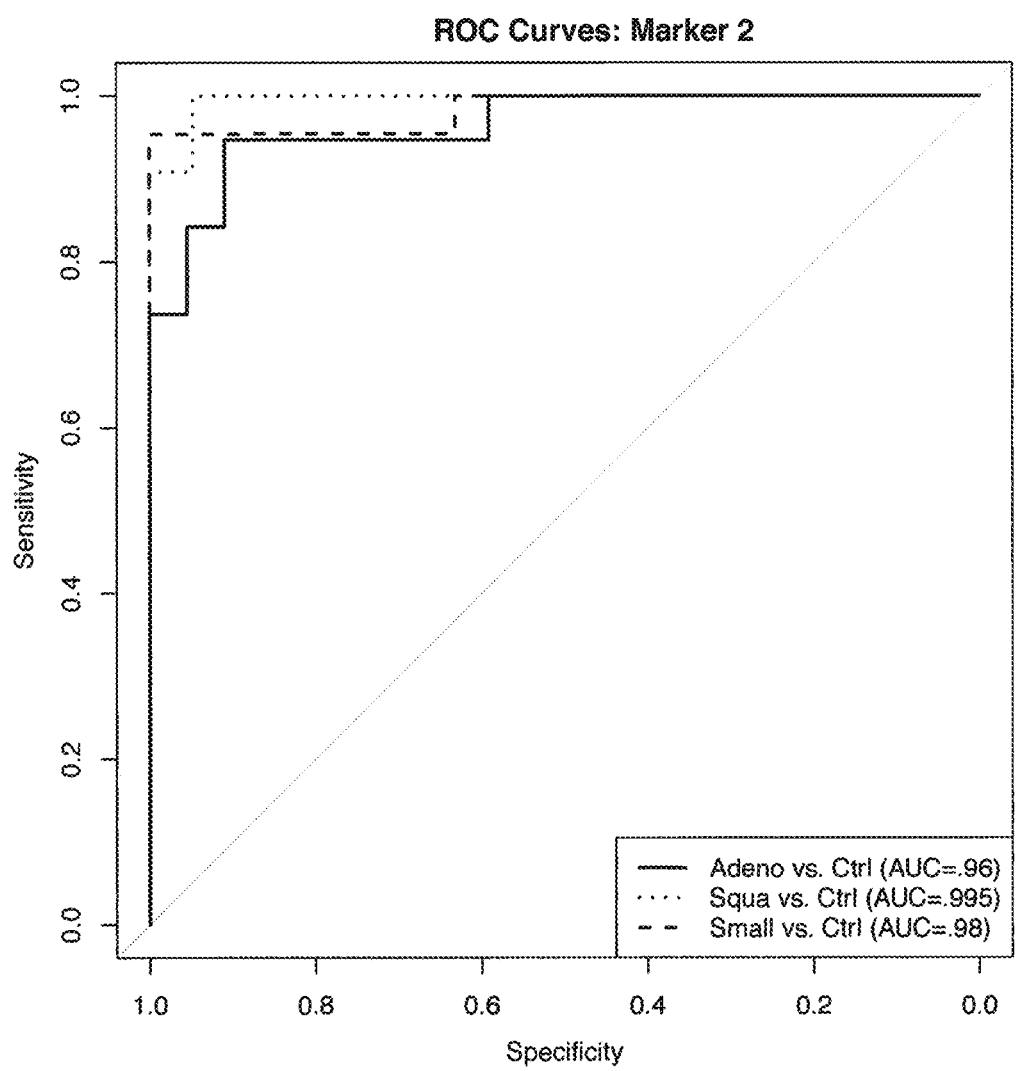
Figure 11A:
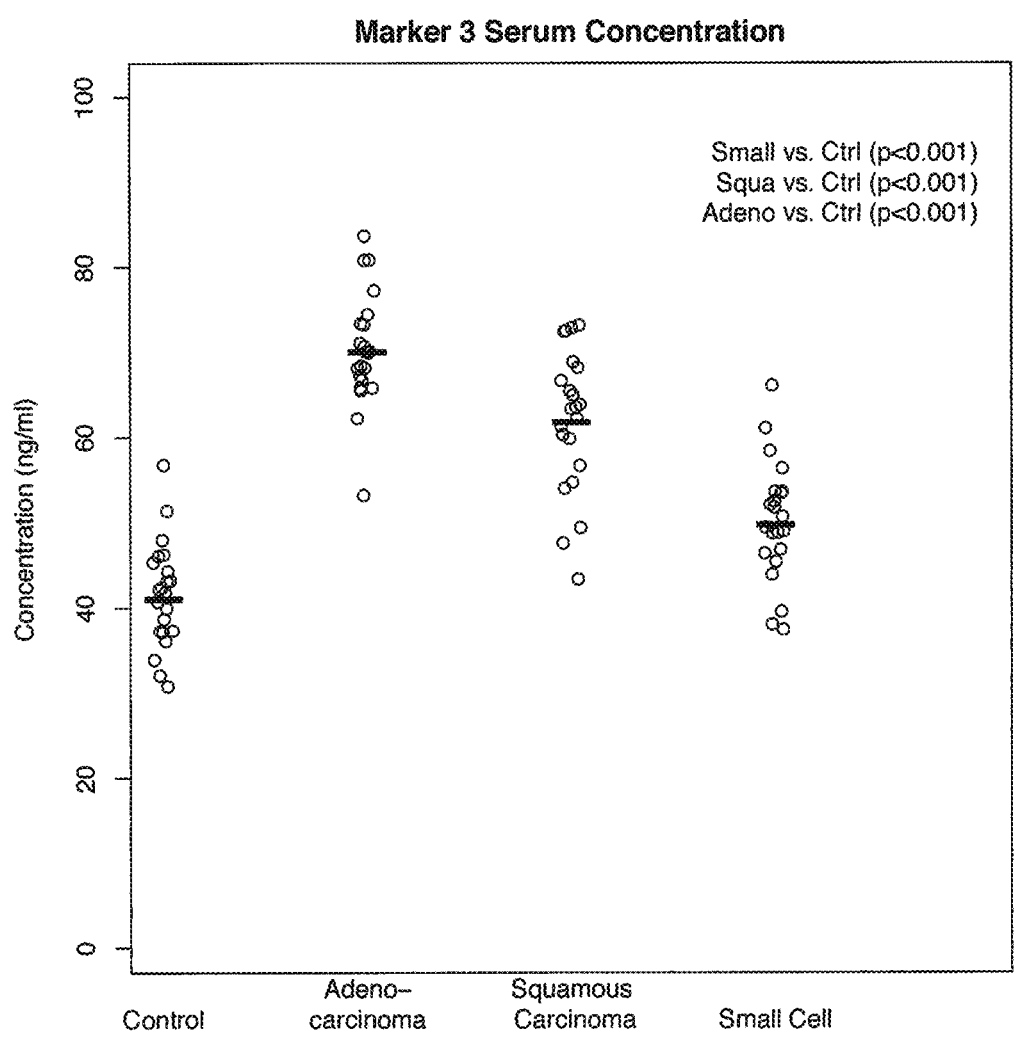
FIG. 11. (A) Marker 3 Serum Concentration by cell type; (B) ROC Curves: Marker 3
Figure 11B:
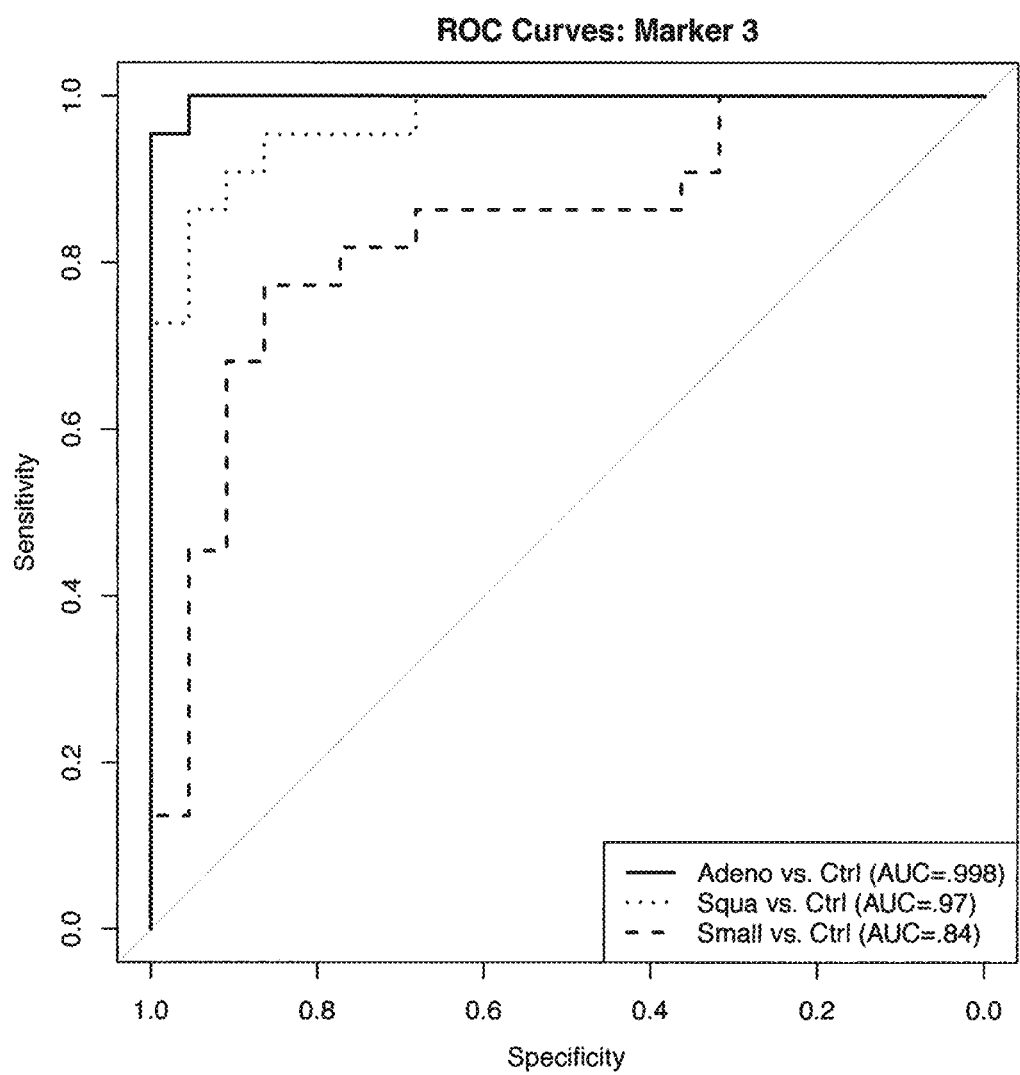
Figure 12A:
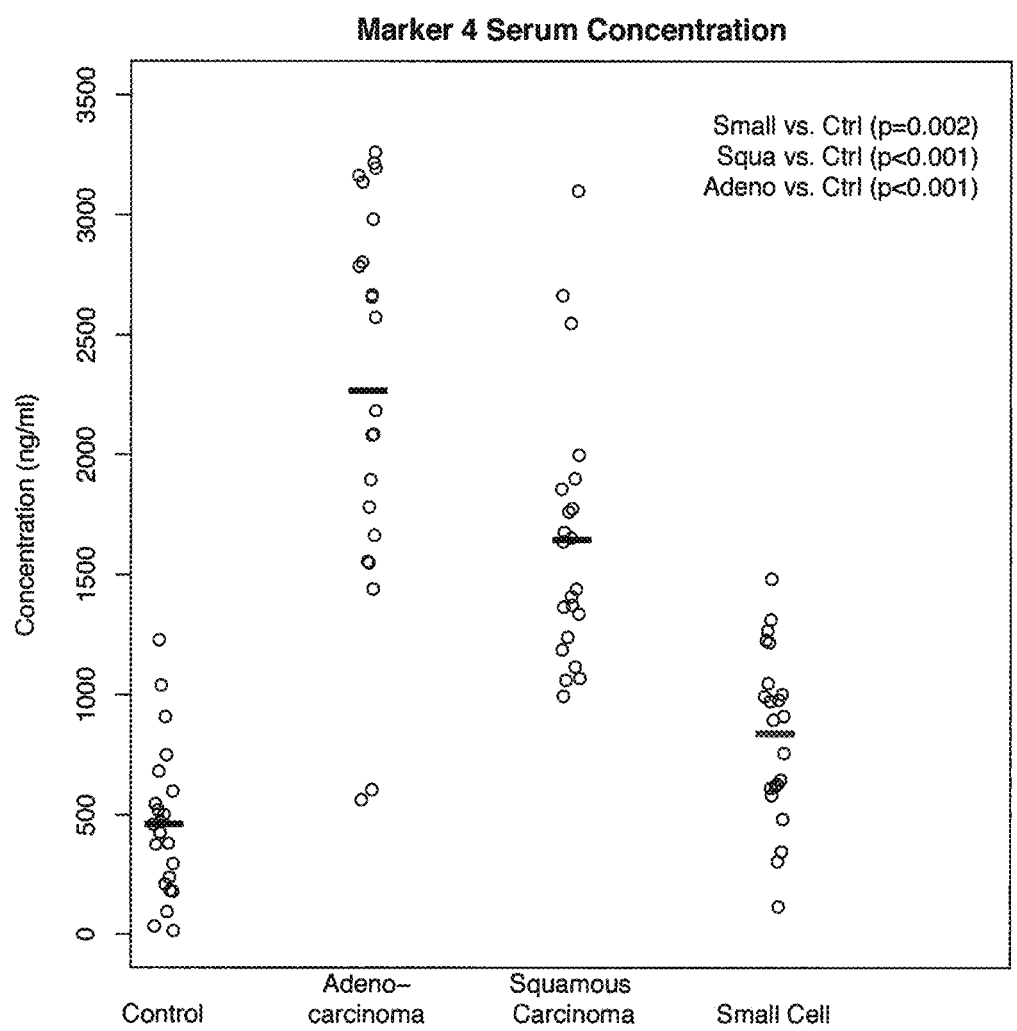
FIG. 12. (A) Marker 4 Serum Concentration by cell type; (B) ROC Curves: Marker 4
Figure 12B:
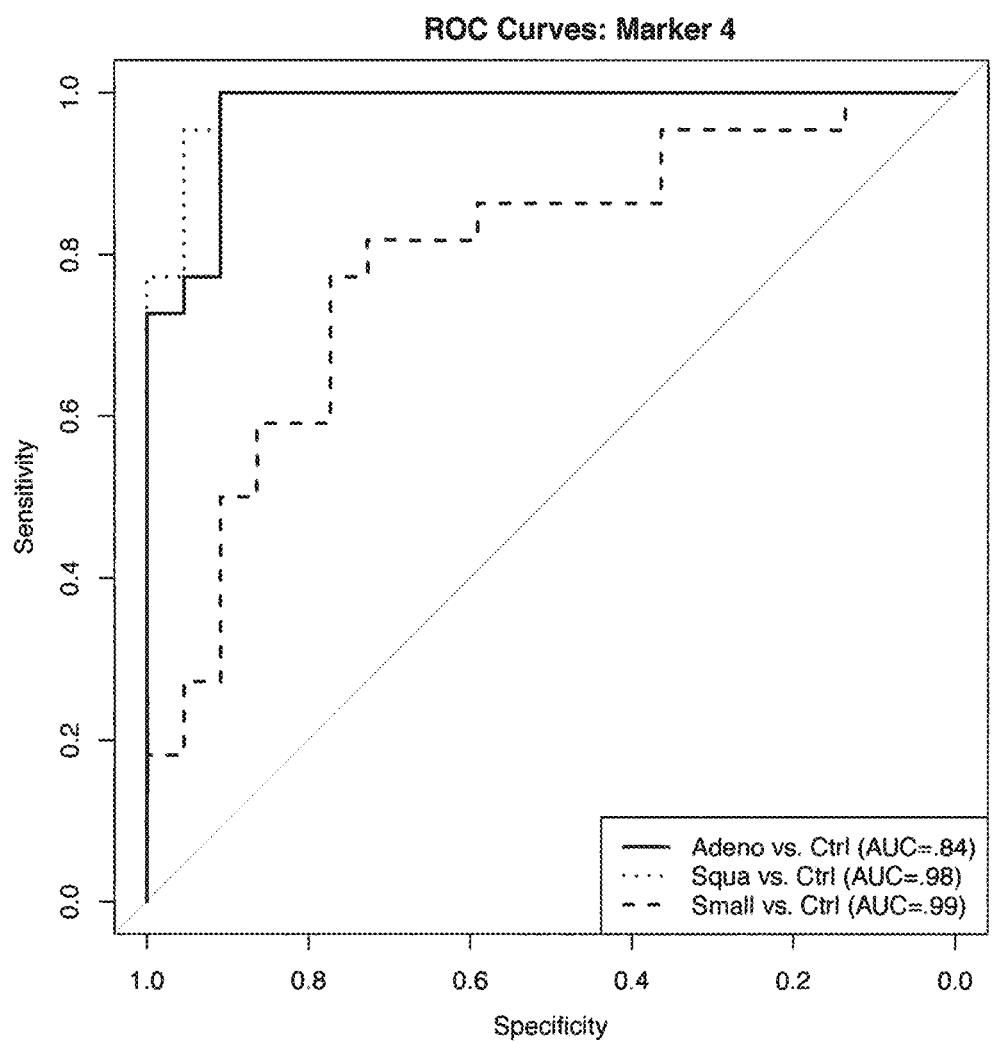
Figure 13A:
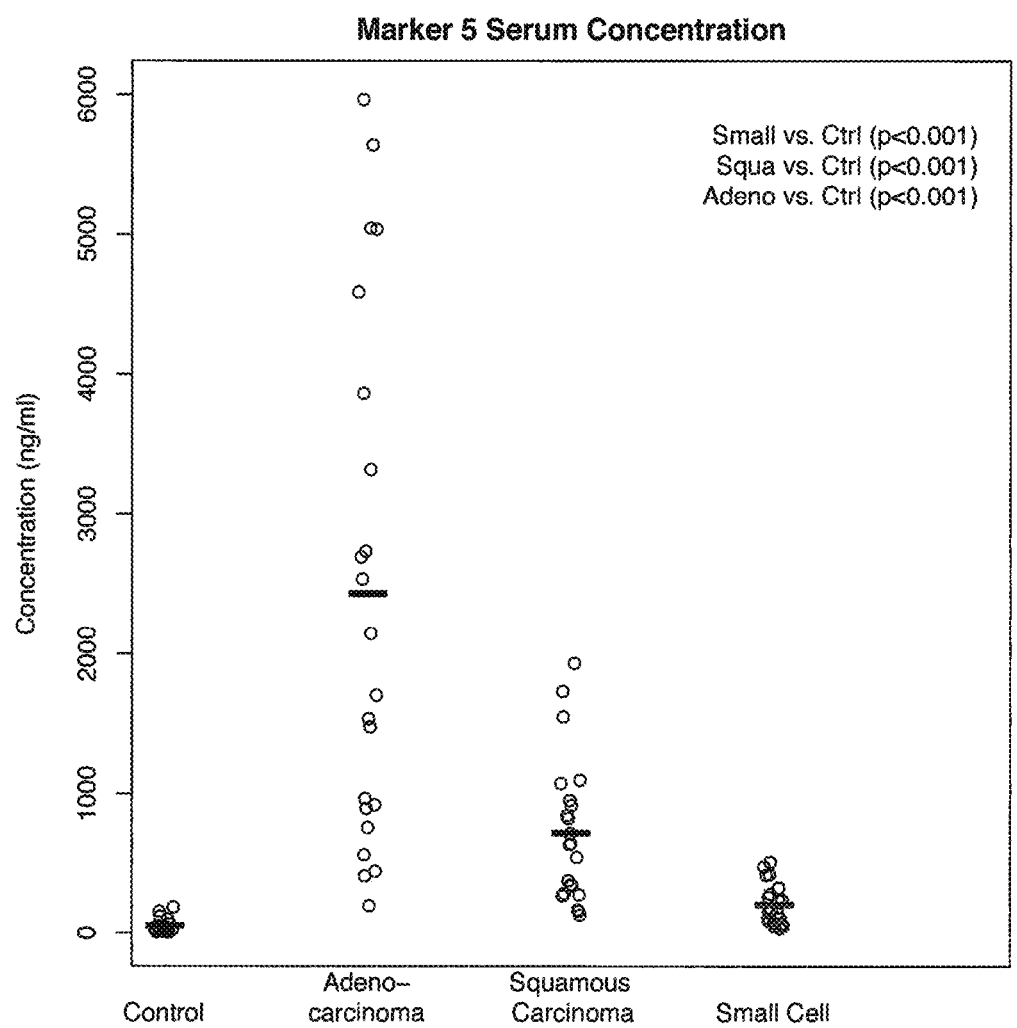
FIG. 13. (A) Marker 5 Serum Concentration by cell type; (B) ROC Curves: Marker 5
Figure 13B:
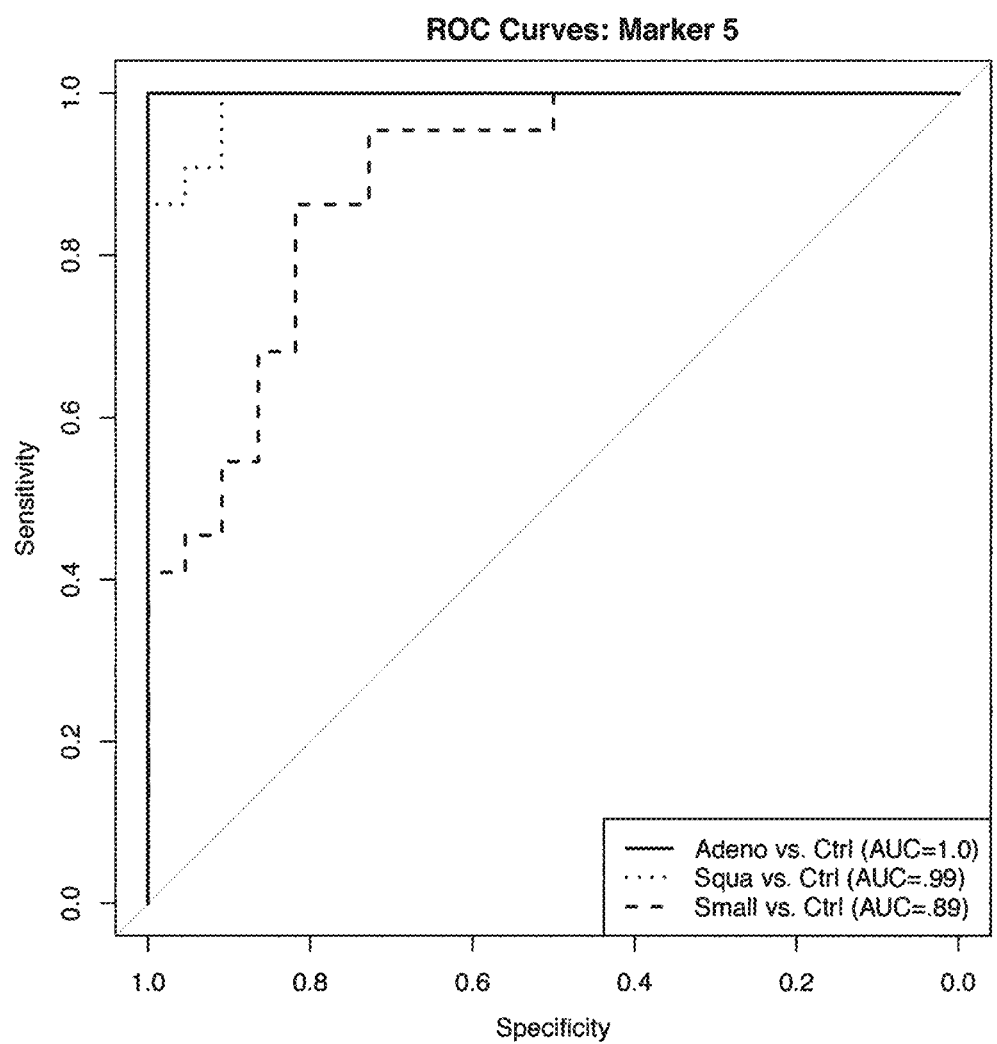
Figure 14A:
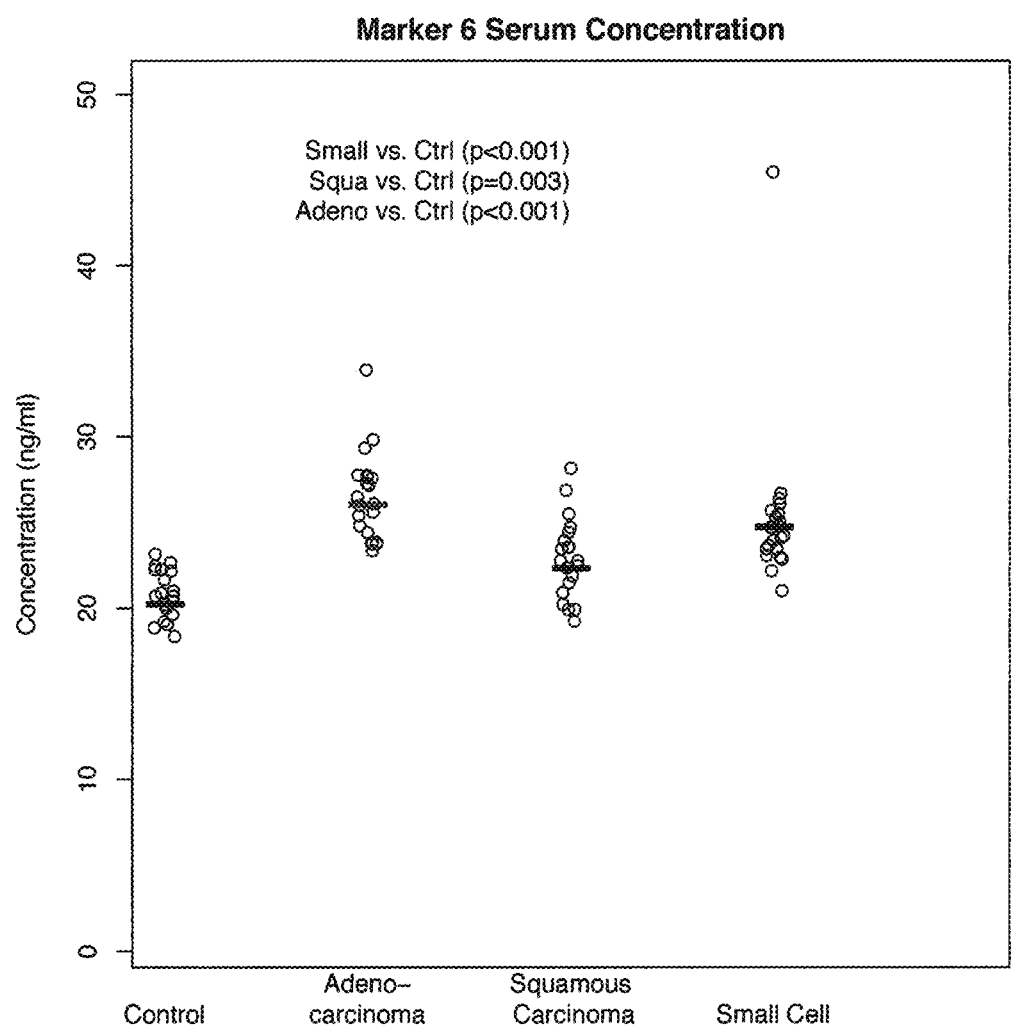
FIG. 14. (A) Marker 6 Serum Concentration by cell type; (B) ROC Curves: Marker 6
Figure 14B:
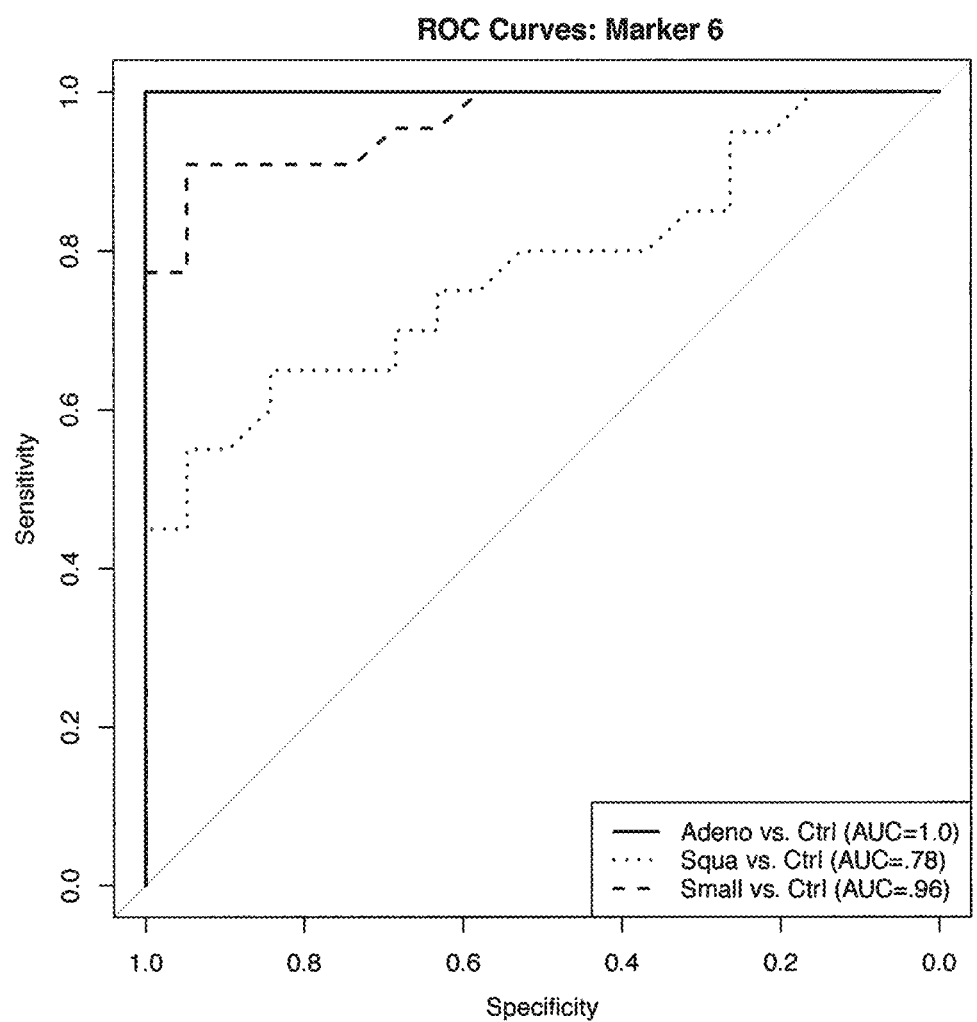
Figure 15A:
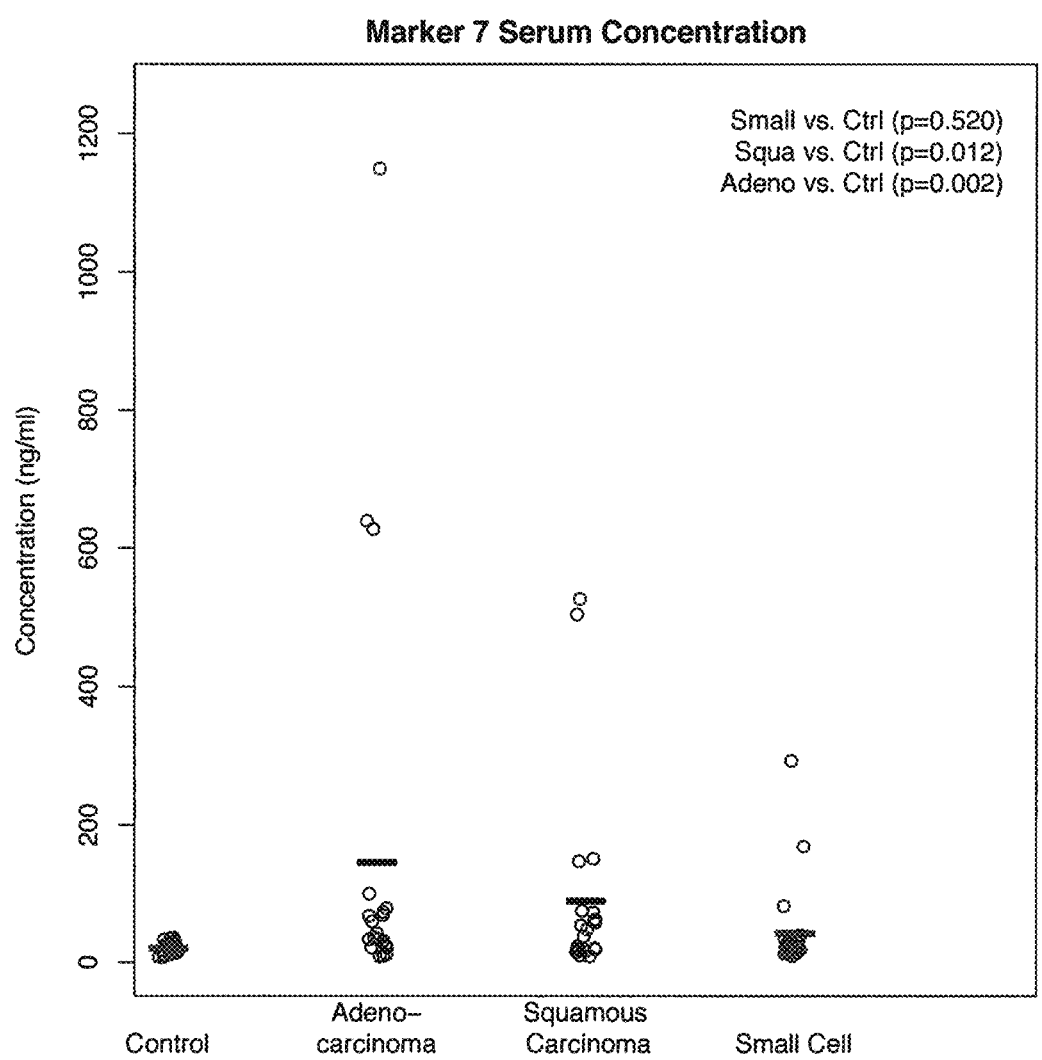
FIG. 15. (A) Marker 7 Serum Concentration by cell type; (B) ROC Curves: Marker 7
Figure 15B:
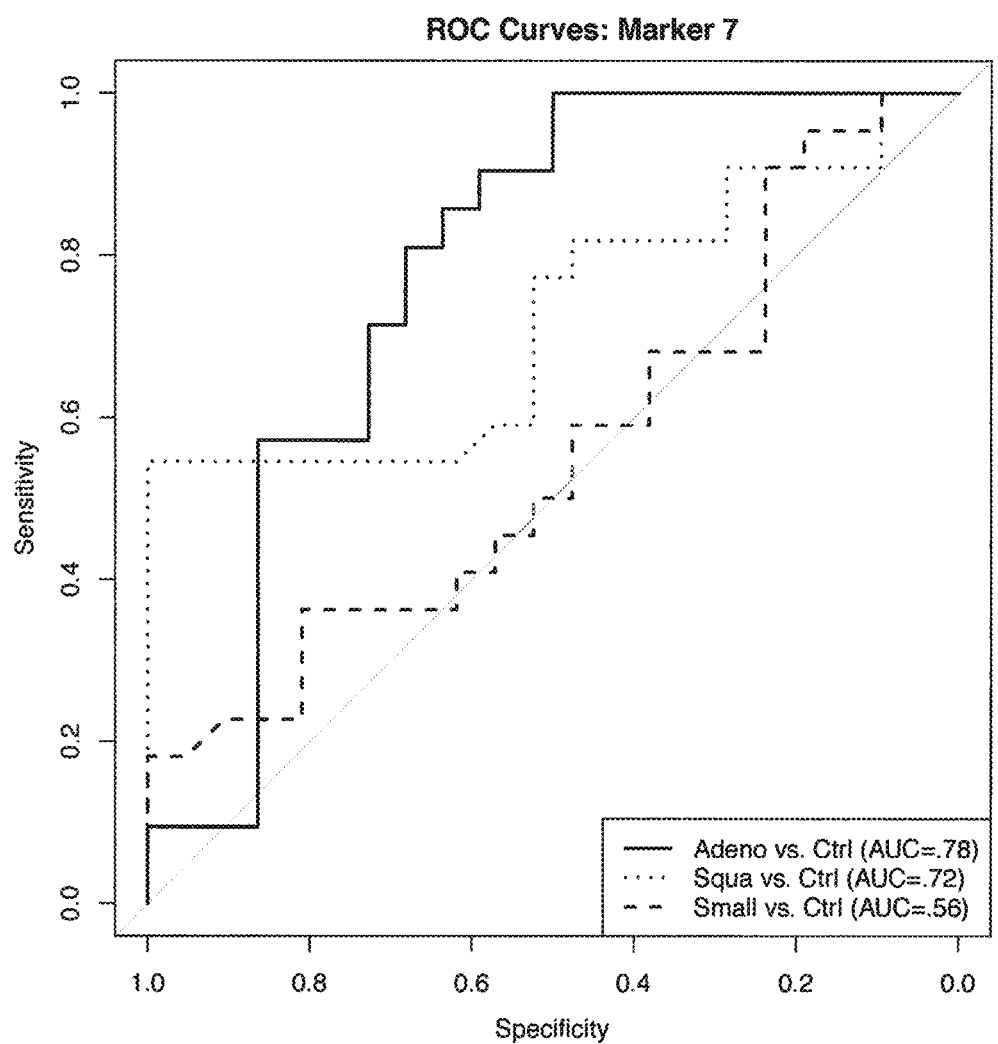
Figure 16A:
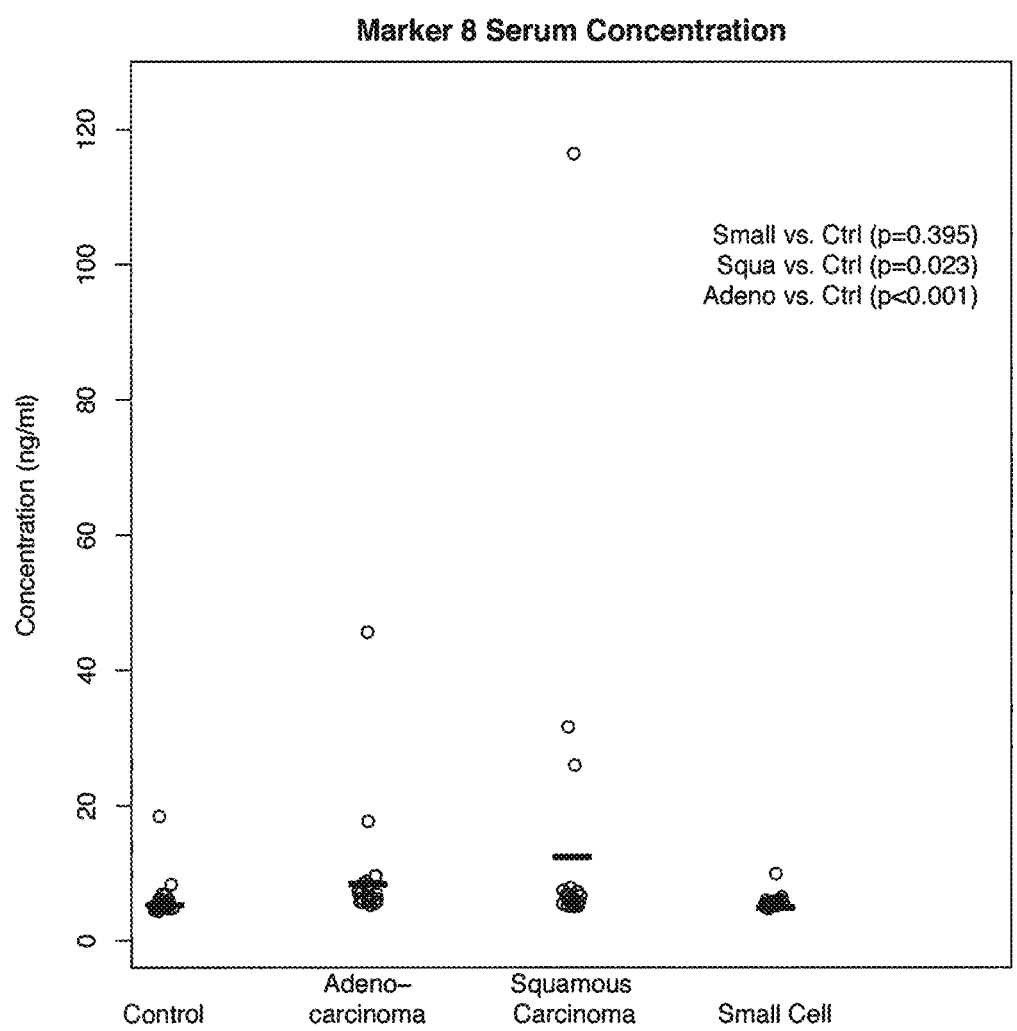
FIG. 16. (A) Marker 8 Serum Concentration by cell type; (B) ROC Curves: Marker 8
Figure 16B:
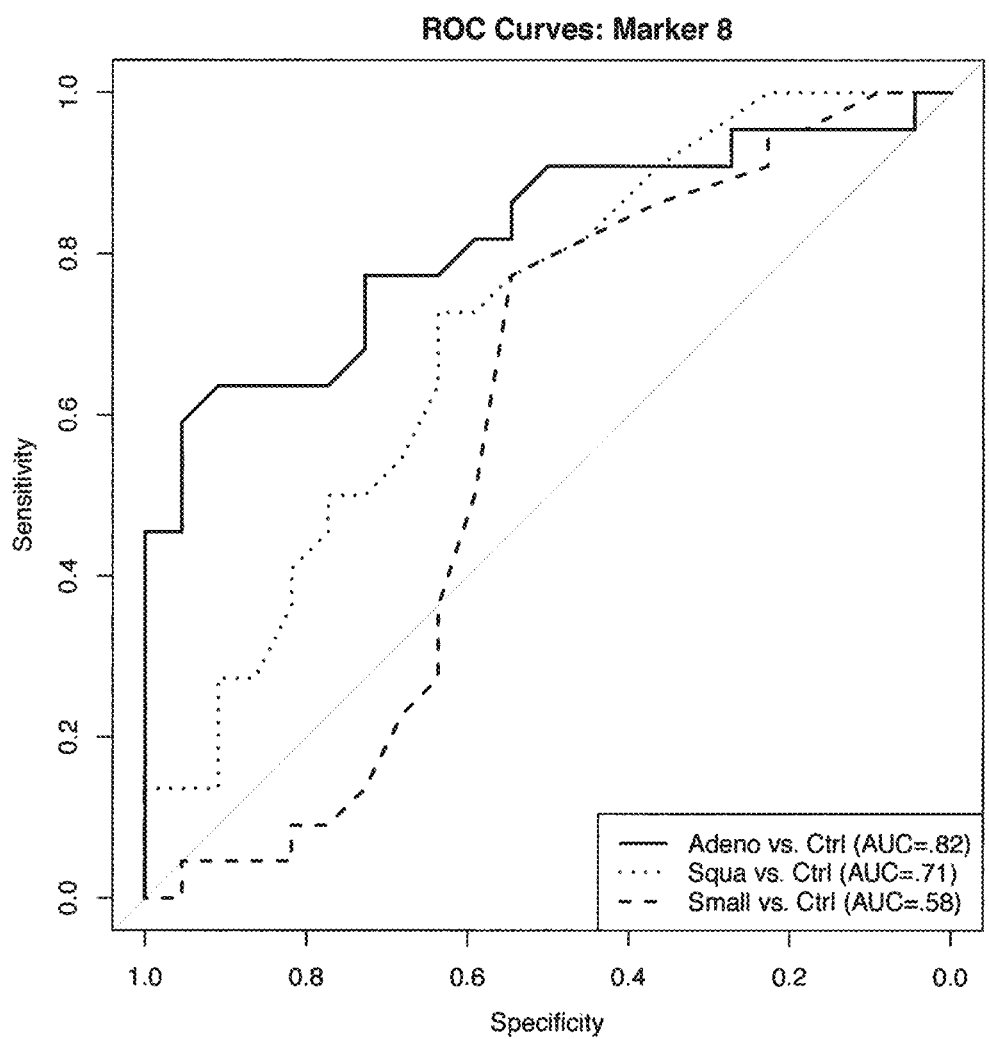
Figure 17A:
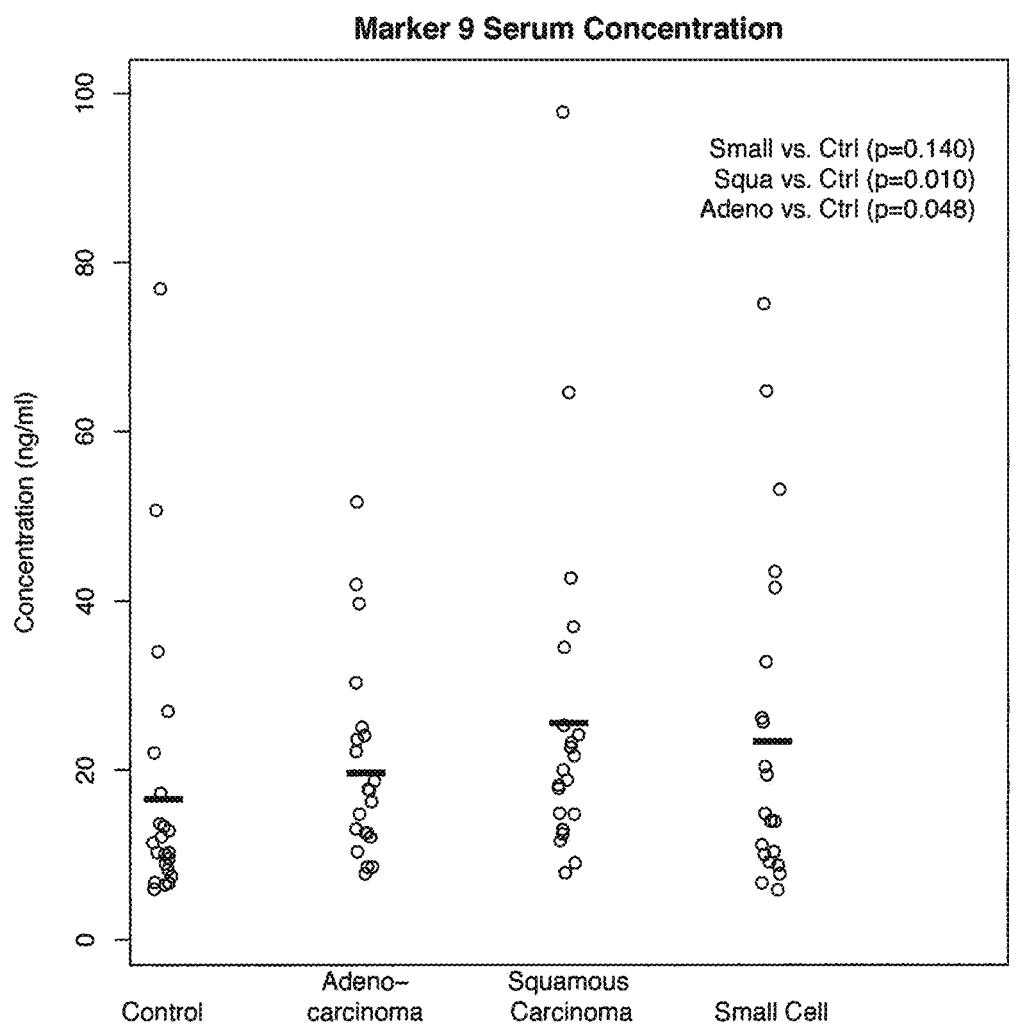
FIG. 17. (A) Marker 9 Serum Concentration by cell type; (B) ROC Curves: Marker 9
Figure 17B:
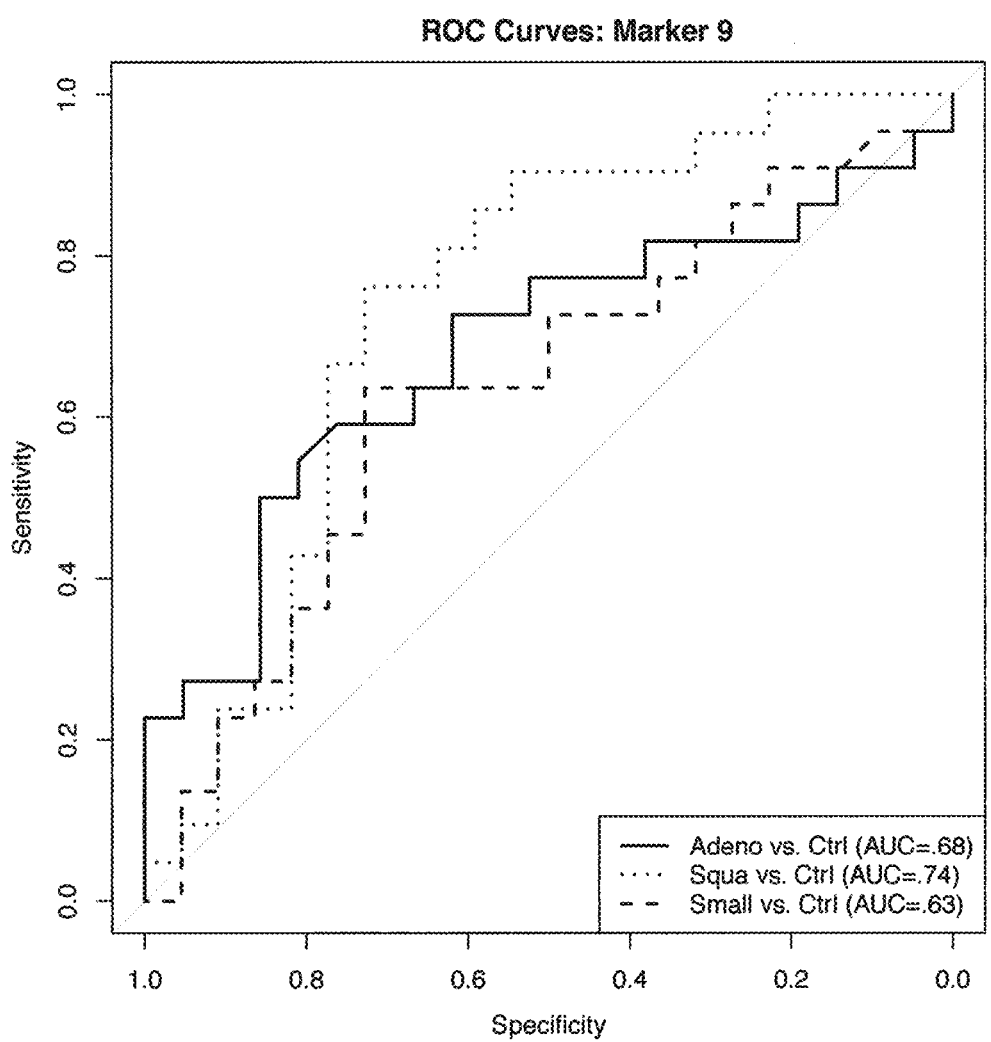
Figure 18A:
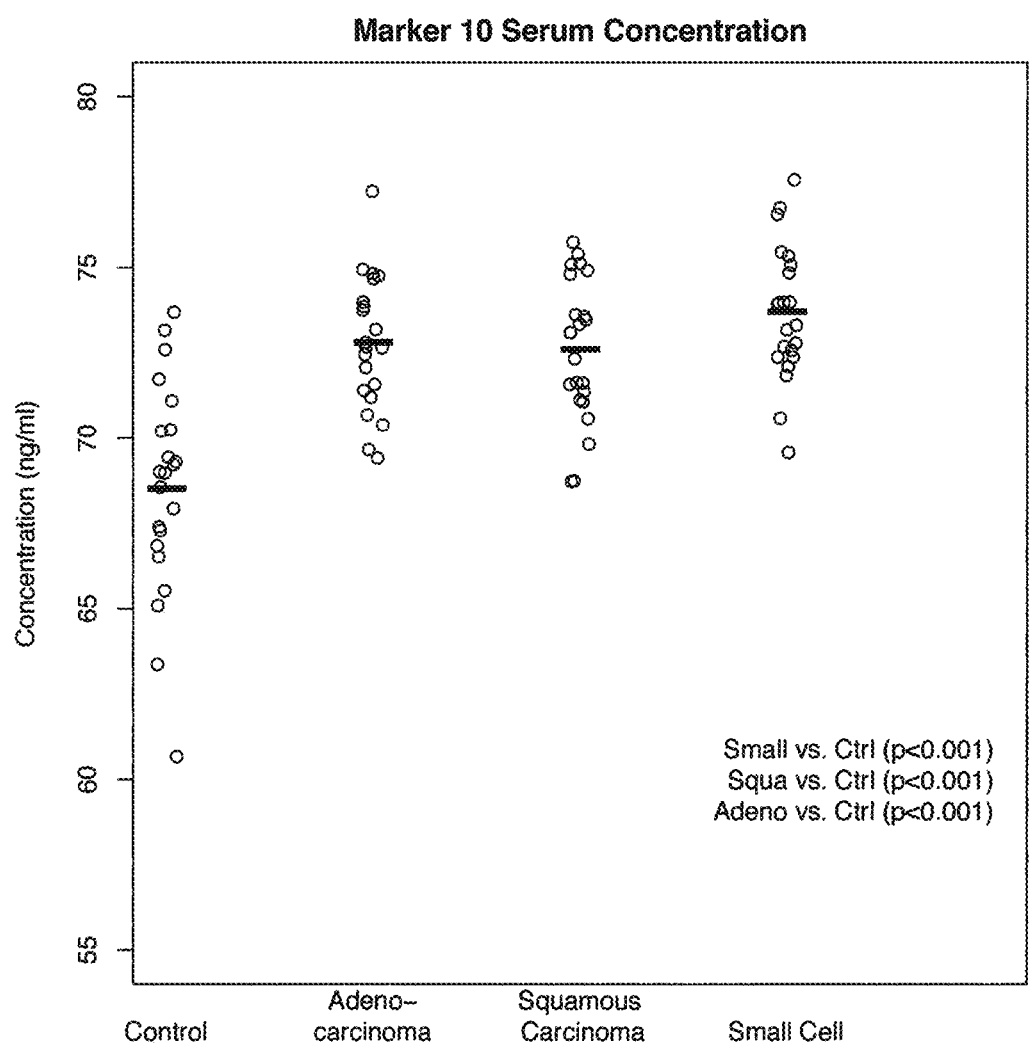
FIG. 18. (A) Marker 10 Serum Concentration by cell type; (B) ROC Curves: Marker 10
Figure 18B:
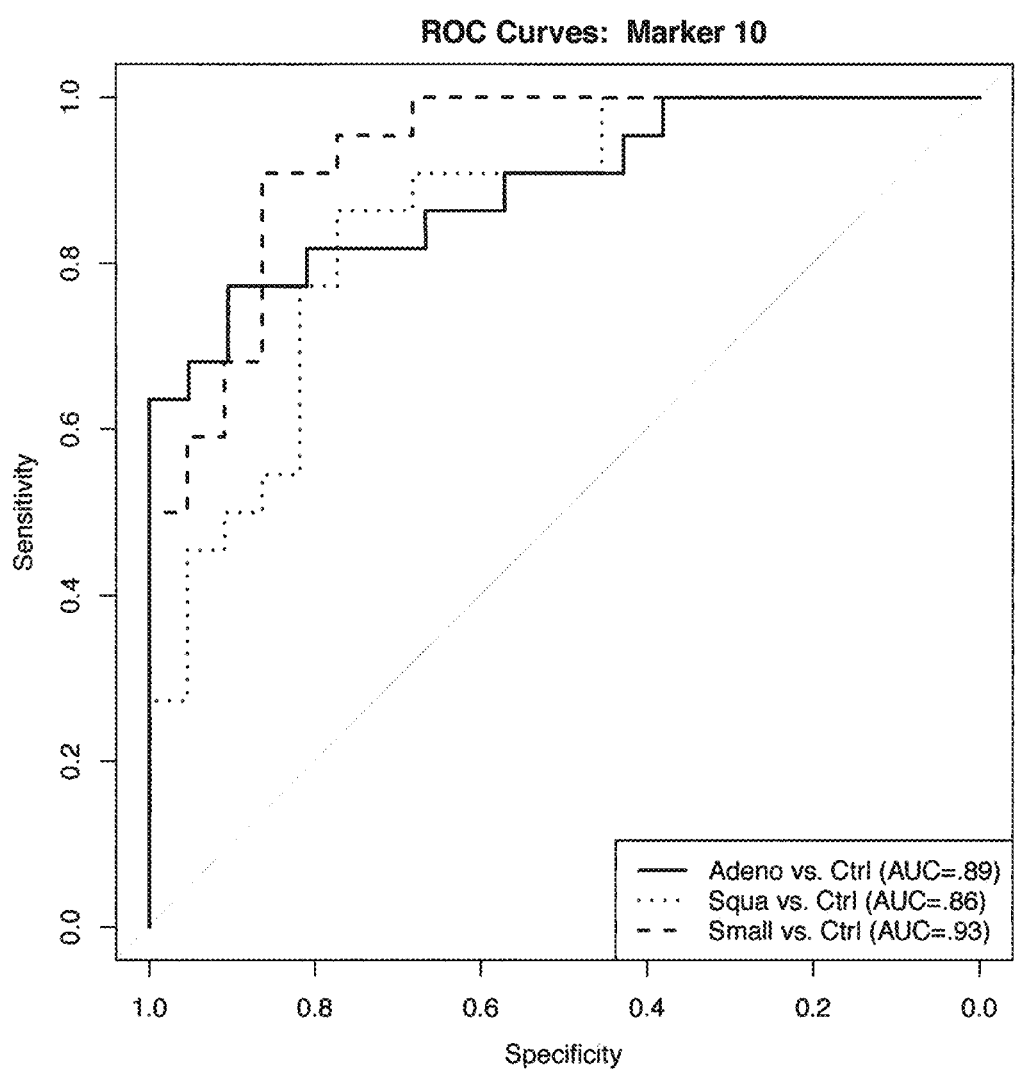
Figure 19A:
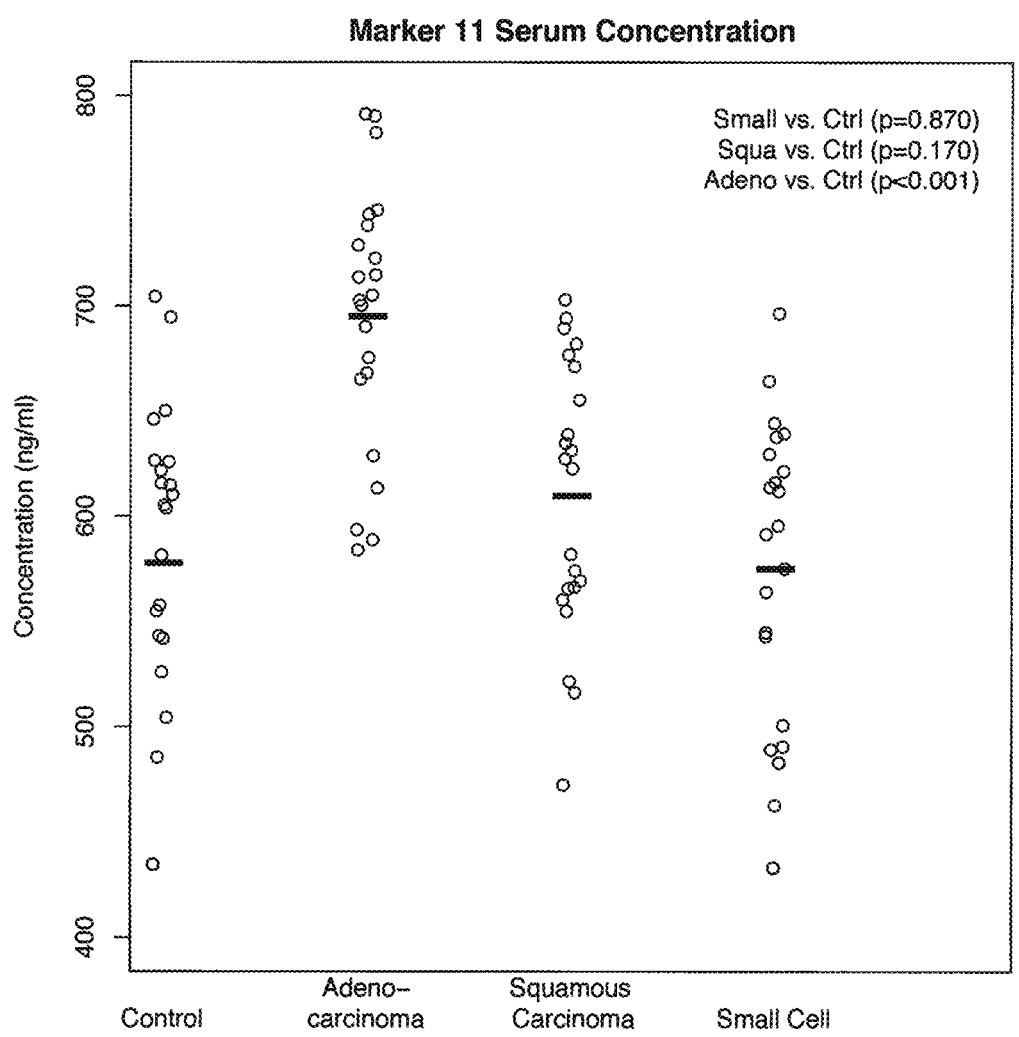
FIG. 19. (A) Marker 11 Serum Concentration by cell type; (B) ROC Curves: Marker 11
Figure 19B:
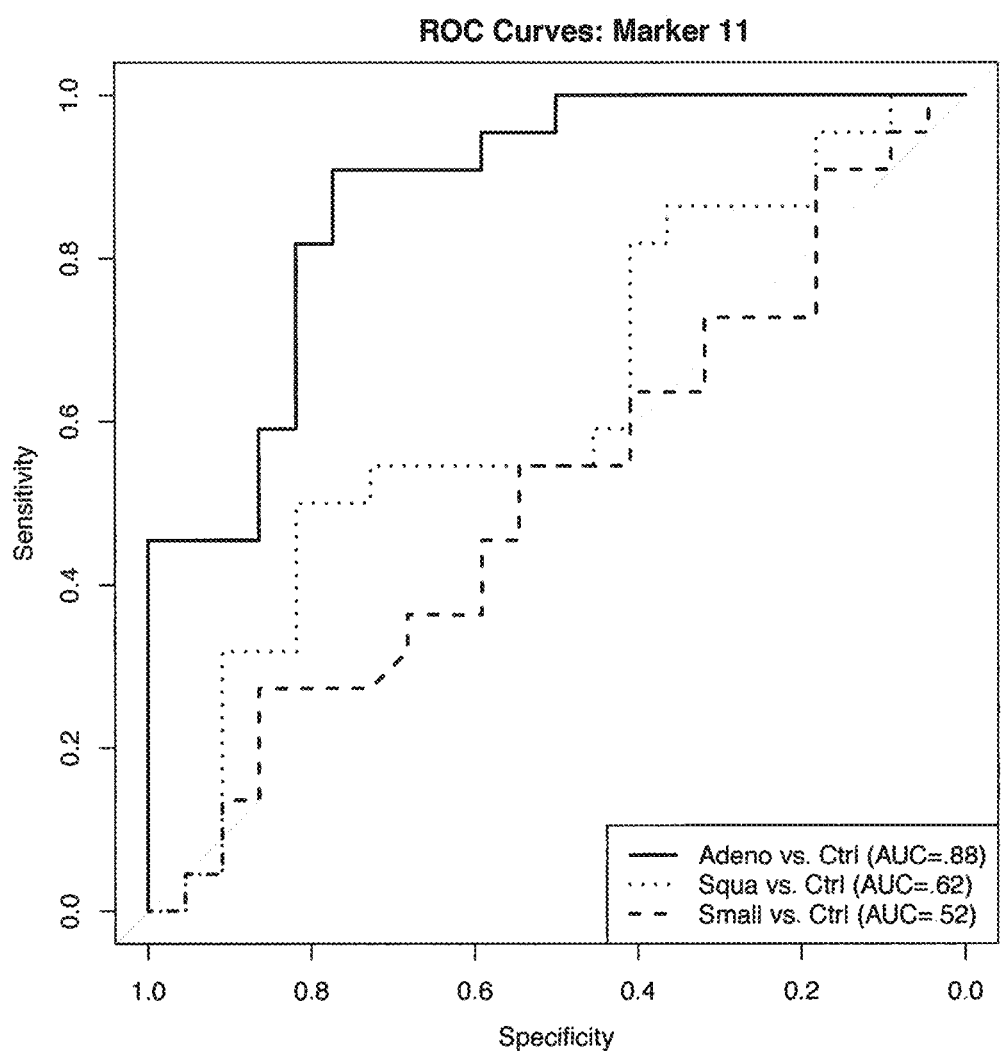
Figure 20A:
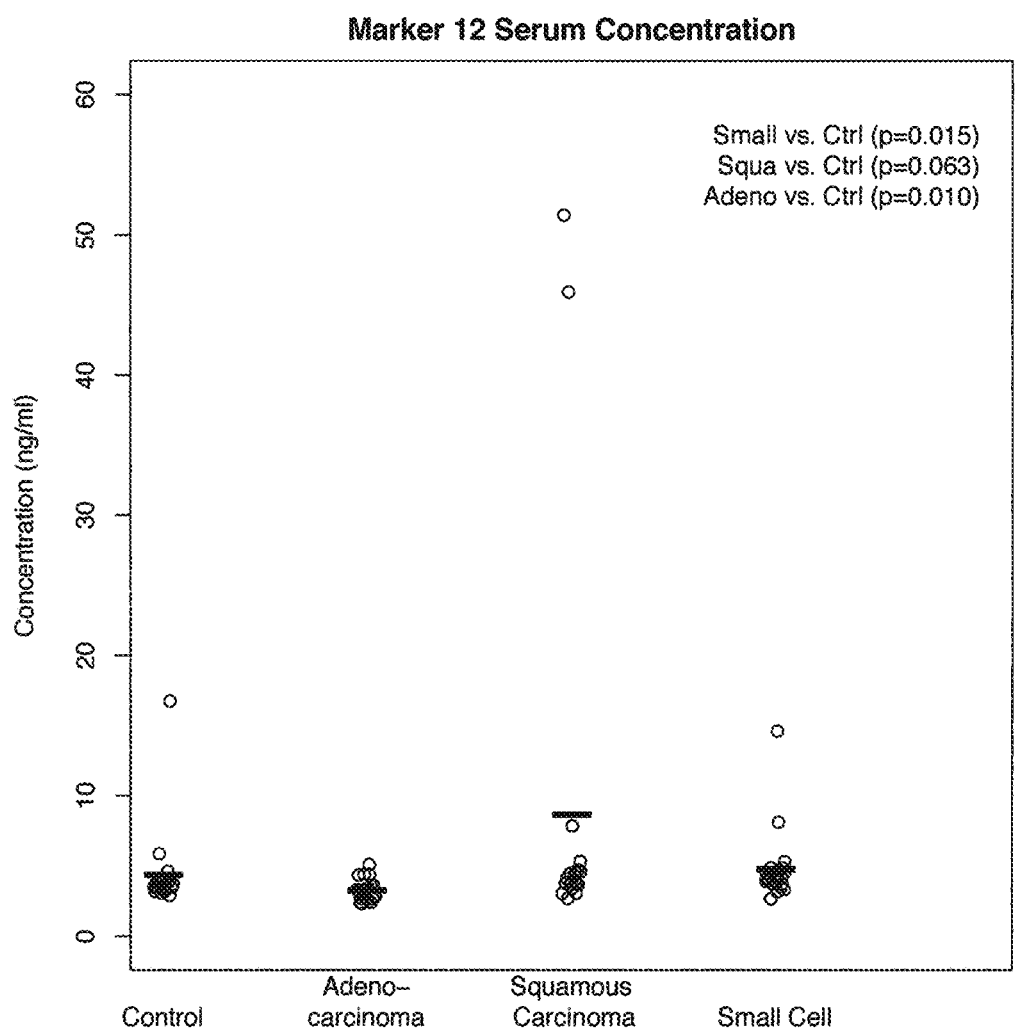
FIG. 20. (A) Marker 12 Serum Concentration by cell type; (B) ROC Curves: Marker 12
Figure 20B:
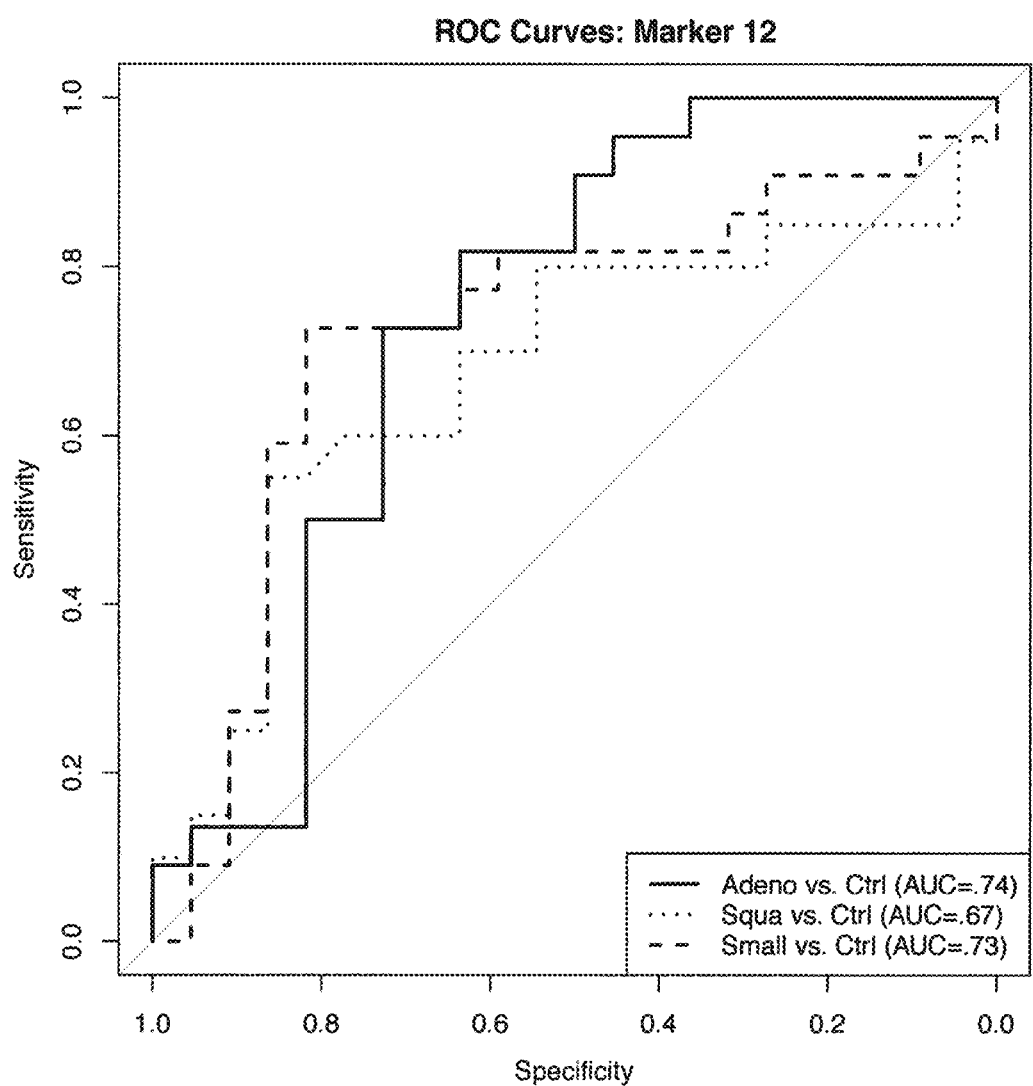
Figure 21A:
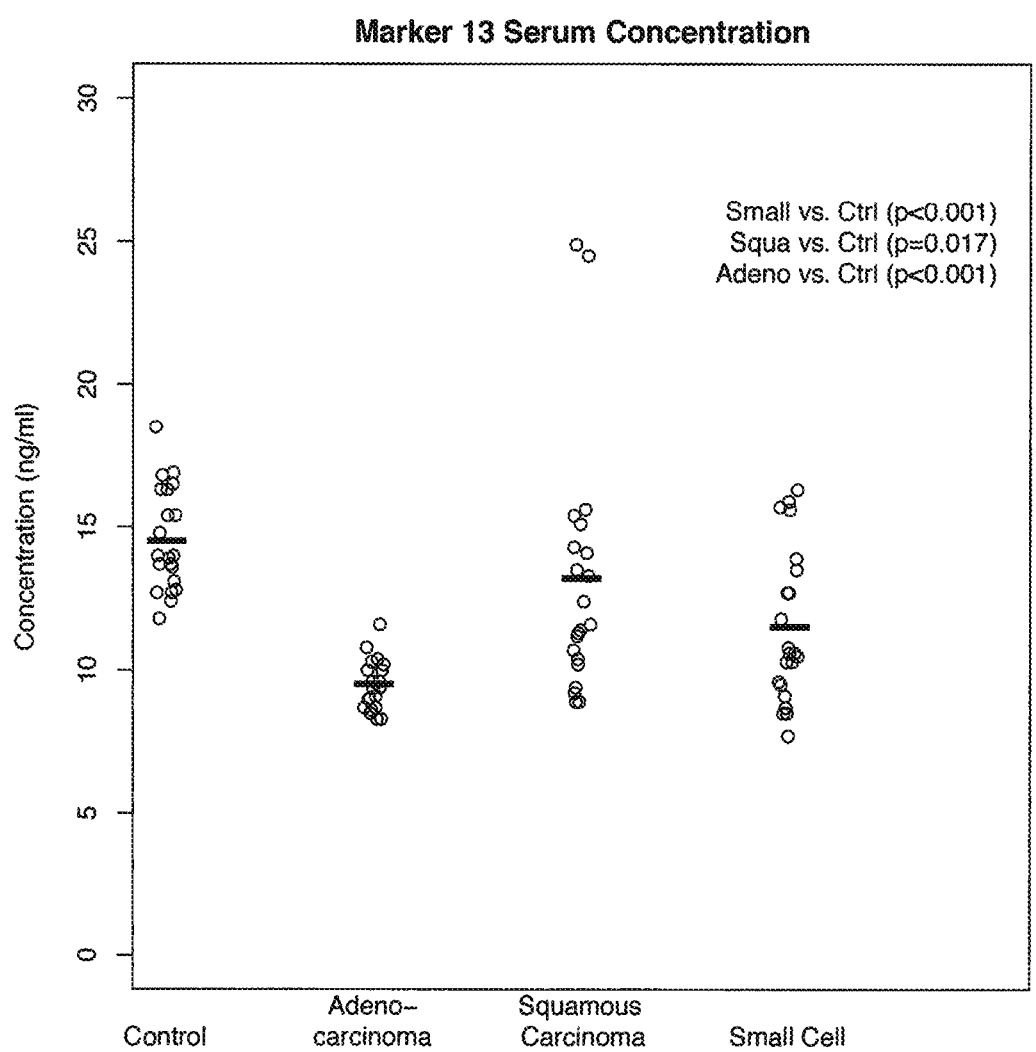
FIG. 21. (A) Marker 13 Serum Concentration by cell type; (B) ROC Curves: Marker 13
Figure 21B:
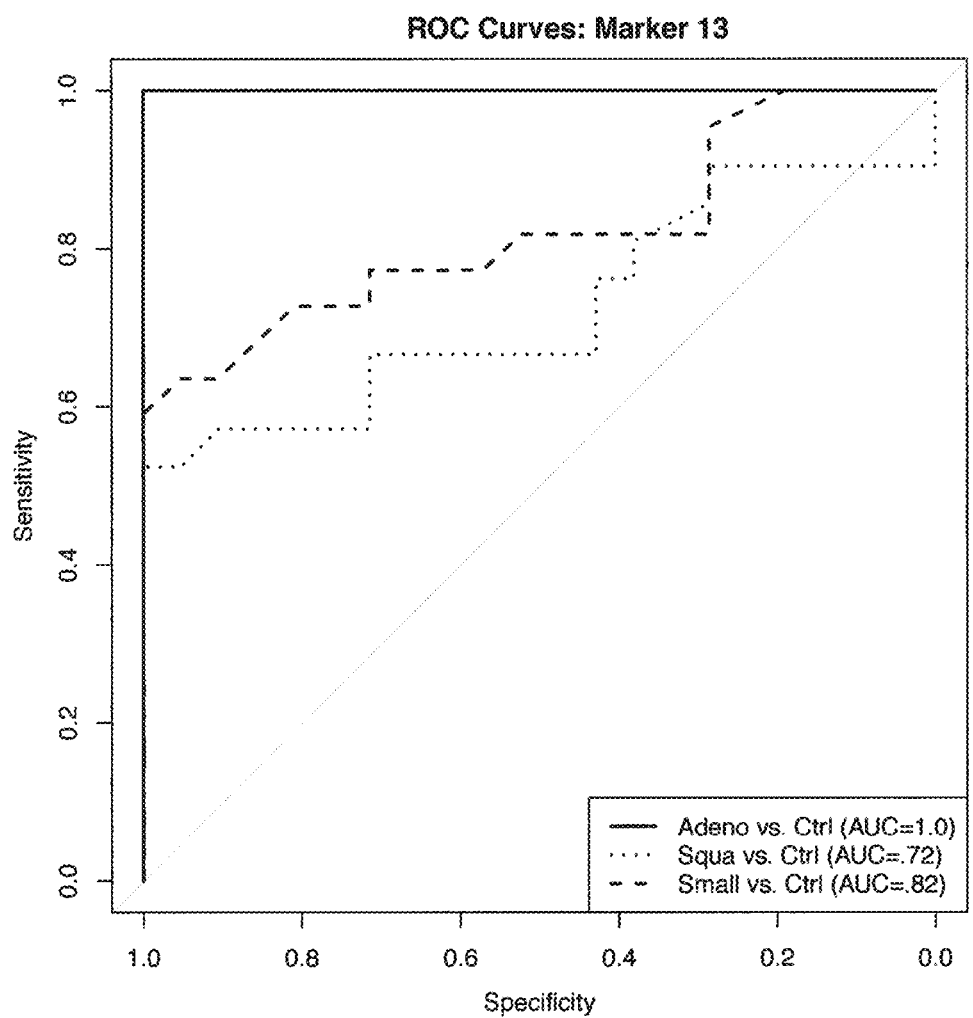

Indeed, the CHI3L1 protein concentration in the serum of human patients with several types of lung cancer was significantly elevated (FIG. 8). CHI3L1 expression plays an important role to facilitate lung cancer pathogenic process by promoting inflammation, as demonstrated in FIGS. 3A and 4A. Recombinant CHI3L1 fusion protein directly stimulated LLC proliferation and growth (FIG. 7).

Therefore, CHI3L1 is a biomarker for inflammation-induced lung cancer prediction in animal models. Additional secretory proteins may be combined with CHI3L1 as biomarkers for lung cancer.

After characterizing each one of selected secretory proteins in the lung cancer animal models and human tissues, the inventors combined the selected proteins as a panel to discriminate cancer-related conditions.

Methods described are applicable to stratifying patients into high-risk, moderate-risk, and low-risk categories for lung cancer. Periodic testing of some of all of the identified biomarkers can be used to monitor progression, remission, treatment, or relapse. For example, a patient may present with a lung cancer characterized by over-expression of particular biomarkers described. The profile or signature of up-regulated biomarkers is documented, the patient is treated. During and after treatment, test samples of serum or BALF are collected and tested, and the test results are documented. Test sample results over time are collected. Levels of biomarker detection, and trends over time, distinguish or classify the lung cancer progression or responsiveness to treatment.

Often the mechanism of action is not known in detail when a treatment is introduced in a clinical setting. Insight into the molecular background of the mode of action of some chemotherapeutics is emerging, and examples of relationships between the effect of treatment with a specific chemotherapy and specific genetic changes in the cancer cells have been shown.

By monitoring response to chemotherapy using biomarkers, determination of efficacy or responsiveness can be assessed at an earlier stage. This enables a patient-tailored therapy, with drug selection and dosage adjustment based on patient response to administered therapeutic agents. An advantage of using the described biomarkers is to aid in determining the effectiveness of treatments despite uncertainty in the mechanism of action.

An advantage of using the disclosed biomarkers is the opportunity for earlier diagnosis and less invasive monitoring of at-risk patients. In a particular embodiment, a patient is classified as at-risk if the patient presents with one or more of the following conditions: chronic obstructive pulmonary disorder (COPD), family history of lung cancer, asbestosis, silicosis, work history of mining, history of smoking, air pollution exposure, emphysema, radon exposure, or advanced age over 65.

Another advantage of using biomarkers is in post-surgical assessment. If a biomarker signature of a cancer persists or recurs after surgical removal of cancer tissue, there is an indication that: not all tumor tissue was removed, the cancer has metastasized, or the patient has relapsed. This indicates a need for additional and more aggressive treatment. In some embodiments, the post-surgical sample is taken 6-10 weeks after the surgery, 2-4 months after the surgery, or 3-6 months after the surgery. In some embodiments, periodic post-surgical samples are tested regularly.

Treatment with cytotoxic agents is a well-established standard for most advanced cancers and is also increasingly becoming an integrated part of treatment in primary and early cancers. Cytotoxic chemotherapy in early cancers may be administered as the primary treatment, before surgery and radiotherapy. It may also be administered with, or as an adjuvant to, other therapies.

Many chemotherapy regimens for first-line treatment of lung cancer use two drugs. Frequently, a platinum compound, such as cisplatin (Platinol™) or carboplatin (Paraplatin™), is used in conjunction with another chemotherapeutic compound. Compounds administered may include: paclitaxel (Taxol™), bevacizumab (Avastin™), gefitinib (Iressa™), Erlotinib (Tarceva™), Pemetrexed (Alimta™), 5-Fluorouracil (5-FU), gemcitabine, docetaxel, vinblastine (vindesine or vinorelbine), or other compounds known in the art. If a cancer does not respond to the first set of drugs administered, a second-line chemotherapeutic compound may be selected. Docetaxel (Taxotere™), Erlotinib (Tarceva™), Gefitinib (Iressa™), or Pemetrexed (Alimta™) are commonly used as second-line treatments.

In some embodiments, a particular drug treatment is contraindicated if the biomarker profile indicates that a patient would receive little benefit from the drug treatment. In some embodiments, biomarker profiling results indicate a need for greater monitoring or cessation of a particular drug treatment. In some embodiments, little or no change in the biomarker signature of selected biomarkers in a post-treatment assessment, as compared with a pre-treatment assessment, prompts the cessation of the treatment or elicits the inception of a second treatment. The second treatment may be a change in dosage, dosing schedule, type of medication, use of radiation therapy, or other treatment. In some embodiments, the threshold change is 50%, 40%, 25%, 20%, 15%, or 10%. In some embodiments, a worsening of a condition at the molecular level indicates a need to cease a particular treatment. For example, a change further deviating from a non-cancerous control in the sampled biomarker signature of the selected biomarkers in a post-treatment assessment, as compared with a pre-treatment assessment, contraindicates use of the treatment.

Embodiments of the invention include methods of determining coverage or denial of health insurance reimbursement and/or payment for treatments for disease based on the result of diagnostic and prognostic methods described herein. Provided is a method of excluding a treatment from insurance coverage, the method comprising: identifying a patient having health insurance; receiving a result of a diagnostic procedure on the patient, wherein the diagnostic procedure comprises determining a biomarker profile for the patient in relation to a drug treatment; and denying health insurance coverage for the drug treatment, if the biomarker profile is outside of a specified classification or range.

A biomarker signature may include detection and measurement of proteins, protein fragments, epitopes, oligonucleotides, or mRNA corresponding to the described biomarkers.

Methods detecting biological markers can be applied using a variety of detection formats including immunohistochemistry, immuno cytochemistry, in situ hybridization, flow cytometry, polymerase chain reaction (PCR), enzyme immuno-assay (EIA), and enzyme linked immunoassay (ELISA). In addition to ELISA, western blot analyses, protein array, and microfluidics reaction on filter are particularly useful in a clinical setting.

Detection of a target biological marker in a biological sample or specimen may be achieved by contacting the target with a molecule which specifically binds to the target. The molecule may be, for example, a protein or a nucleic acid probe (for example, for use in in situ hybridization or Southern or northern blots). The molecule may be linked, either directly or indirectly to a detectable substance, thus permitting the staining and detection of the target contained in a biological sample. Detectable substances that are commonly used include dyes such as Texas red, and FITC, as well as radioactive isotopes, metal particles and enzymes which upon catalysis of a specific substrate permit colormetric detection of the target biological marker (see e.g. Coons et al. 1941, Proc Soc Exp Biol Med 47:200; Nakane and Pierce 1966, J Histochem Cytochem 14:929). One system for the detection of biological markers relies on immunologically derived molecules which specifically bind to a desired target biological marker in a sample.

Antibodies may be produced recombinantly or synthetically. To minimize cross reactivity between binding agents, for example where multiple markers are detected, antibodies derived from different species can be used. Antibodies that may be used include monoclonal and polyclonal antibodies, engineered antibodies including chimeric, CDR-grafted and artificially-selected antibodies produced using phage display or alternative techniques. Recombinant DNA technology may be used to produce the antibodies according to established procedure, in bacterial, yeast, insect or mammalian cell culture.

Immunologically based detection of biological markers advantageously exploits the specificity of immune derived proteins such as antibodies for specific biological markers of interest. Typically, the antibody will recognize a specific epitope on the target biological marker which permits the target to be distinguished and thus detected from other biological markers contained within a given biological sample or specimen. A variety of formats capable of detecting biological markers of interest may be used, including enzyme linked immuno-assays (ELISA), flow cytometry, western blots, radioimmunoassay (RIA) and immunohistochemistry (IHC).

A first binding agent may comprise a nucleic acid probe, e.g., a DNA molecule, an RNA molecule, for use in in situ hybridization. Nucleic acid probes may be synthesized chemically or produced recombinantly in cells (see e.g. Sambrook et al. (1989) Molecular Cloning: A Laboratory Manual, 2nd ed. Cold Spring Harbor Press). In some embodiments, the probe is comprised of a peptide nucleic acid (PNA). A peptide nucleic acid is a nucleic acid molecule in which the deoxyribose or ribose sugar backbone, usually present in DNA and RNA is replaced with a peptide backbone. Methods of making PNAs are known in the art (see e.g. Nielson, 2001, Current Opinion in Biotechnology 12:16) (hereby incorporated by reference). In other embodiments, the probe is comprised of locked nucleic acids (LNA)

(Sorenson et al. 2003, Chem. Commun. 7(17):2130). In some embodiments, the nucleic acid probe specifically binds to the biological marker, e.g., a nucleic acid molecule contained within the biological sample.

A nucleic acid probe, in particular embodiments, comprises at least a sequence that specifically hybridizes to a sequence in the biological sample. In some embodiments, the nucleic acid probe hybridizes to a target sequence in a sample, for example, a nucleic acid sequence such as a genomic DNA sequence or an mRNA sequence, under specific conditions of stringency. As used herein, the term "hybridization under stringent conditions," is intended to describe conditions for hybridization and washes under which nucleotide sequences that are significantly complementary to each other remain bound to each other. The conditions are such that sequences at least 70%, at least 80%, at least 85-90%, at least 95-100% complementary remain bound to each other.

The characterization of lung cancer by secretory proteins is conducive to minimally invasive sample collection, however more invasive sampling techniques may also be used. In addition to sampling serum and BALF, samples may be also obtained from lung tissue and by transbronchial needle aspiration. Samples may be frozen or stored in any manner that minimizes protein degradation.

Characterization of biomarkers may be normalized or compared with measurement of one or more endogenous markers, wherein the marker is infrequently influenced by cancer status or progression. For example, measurement of the biomarker levels in a serum sample could be characterized with regard to albumin. As another example, measurement of the biomarker levels in a lavage sample could be characterized with regard to a pulmonary surfactant-associated protein, such as SFTPA1, SFTPB, SFTPC, or SFTPD.

Certain embodiments of the present invention are defined in the Examples herein. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. All publications, including patents and non-patent literature, referred to in this specification are expressly incorporated by reference herein. Citation of the any of the documents recited herein is not intended as an admission that any of the foregoing is pertinent prior art. All statements as to the date or representation as to the contents of these documents is based on the information available to the applicant and does not constitute any admission as to the correctness of the dates or contents of these documents.

EXAMPLES

Example 1. Materials and Methods

Animal Care

All scientific protocols involving the use of animals have been approved by the Institutional Animal Care and Use Committee (IACUC) of Indiana University School of Medicine and followed guidelines established by the Panel on Euthanasia of the American Veterinary Medical Association. Protocols involving the use of recombinant DNA or biohazardous materials have been approved by the Biosafety Committee of Indiana University School of Medicine and followed guidelines established by the National Institutes of Health Animals were housed under (IACUC)—approved conditions in a secure animal facility at Indiana University School of Medicine.

ELISA

For mouse serum collection, the abdominal cavities of doxycycline-treated or untreated CCSP-rtTA/(TetO)$_7$-CMV-Stat3, CCSP-rtTA/(TetO)$_7$-CMV-MMP12, CCSP-rtTA/(TetO)$_7$-CMV-Api6, c-fms-rtTA/(TetO)$_7$-CMV-Api6 and c-fms-rtTA/(TetO)$_7$-CMV-MMP12 bitransgenic mice were opened after anesthetizing with triple sedative by intraperitoneal (IP) injection. The mouse blood samples were collected from interior vena cava (IVC). Sera were separated by centrifugation at 10,000 rpm for 10 minutes at 4° C. For bronchioalveolar lavage fluid (BALF) collection, the trachea was isolated and cannulated with a 20 gauge luer stub adapter. Using a 1 cc syringe, bronchoalveolar lavage fluid (BALF) was collected by perfusing the lung with 1 ml aliquot of 0.9% sodium chloride and withdrawing back fluids. BAL fluids were centrifuged for 5 minutes at 1,000 rpm and 4° C. to remove cell pellets. CHI3L1 concentrations in mouse and human serum (50-100 µl) were determined by Mouse Chitinase 3-like 1 Quantikine ELISA Kit and Human Chitinase 3-like 1 Quantikine ELISA Kits according to the manufacturer's instruction (R&D Systems, Minneapolis, Minn.). The human serum samples of normal objects and lung cancer patients were obtained from the Biosample Repository Core Facility (BRCF) of Fox Chase Cancer Center in Philadelphia (supported by NCI). The human serum samples were diluted to 1:100 before assay.

Western Blotting

For Stat3C-Flag fusion protein detection, CCSP-rtTA/(TetO)$_7$-CMV-Stat3 bitransgenic mice were anesthetized and lungs were removed and homogenized in radioimmunoprecipitation assay (RIPA) buffer. Lung lysates (10 µg) were fractionated on a Novex® 4-20% Tris-Glycine Mini Gel (Invitrogen, Carlsbad, Calif.). After transferring to the polyvinylidene difluoride membrane (Bio-Rad, Hercules, Calif.), the membrane was blotted with 5% nonfat dry milk PBS and hybridized with rabbit anti-Flag antibody (Sigma, St Louis, Mo.). Following incubation with secondary antibody, the proteins were detected with chemiluminescent substrate (SuperSignal, Rockford, Ill.). For CHI3L1 protein detection, BALFs from doxycycline-treated or untreated CCSP-rtTA/(TetO)$_7$-CMV-Stat3 bitransgenic mice were collected as described above and diluted with Laemmli sample buffer (Bio-Rad, Hercules, Calif.) at 1:1, then heated in boiling water for 5 min Gel electrophoresis and antibody hybridization were performed following the same procedure as above except that rat anti-mouse ChI3L1 primary antibody (1:1,000, R&D, Minneapolis, Minn.) and goat anti rat IgG secondary antibody (1:3000, Vector Laboratories, Burlingame, Calif.) were used. The protein bands were visualized with a Vectastain Elite ABC kit (Vector Laboratories) following a procedure recommended by the manufacturer.

Immunohistochemistry and Immunofluorescent Staining

For immunohistochemical staining, the lungs from doxycycline-treated or untreated CCSP-rtTA/(TetO)$_7$-CMV-Stat3, CCSP-rtTA/(TetO)$_7$-CMV-MMP12, CCSP-rtTA/(TetO)$_7$-CMV-Api6, c-fms-rtTA/(TetO)$_7$-CMV-Api6 and c-fms-rtTA/(TetO)$_7$-CMV-MMP12 bitransgenic mice were inflated with a fixative solution (4% paraformaldehyde, 1×PBS), dissected out, and stored in fixative at 4° C. for 24 hours as previously described. After fixation and embedding in paraffin, tissues were sectioned at 5-µm thick. Multiple sections from each lung were blocked with nonfat milk (4% in 1×PBS) for 30 min., then incubated with rat anti-mouse CHI3L1 (1:100; R&D Systems, Minneapolis, Minn.) at 4°

C. overnight. Tissue sections were washed and incubated with biotinylated secondary antibody goat anti-rat IgG. The signals were detected with a Vectastain Elite ABC kit (Vector Laboratories, Burlingame, Calif.) following a procedure recommended by the manufacturer.

For immunofluorescence staining, sections were hybridized with rat anti-mouse ChI3L1 antibody (R&D System) and rabbit anti-mouse F4/80 (abcam, Cambridge, Mass.) antibody as primary antibodies. A FITC-conjugated donkey anti-rat IgG (Santa cruz, Cruz, Dallas, Tex.) and a Cy3-conjugated donkey anti-rabbit IgG (Jackson ImmunoResearch, West Grove, Pa.) at a dilution of 1/200 were used as the secondary antibodies. Sections were co-stained with DAPI. Slides were examined under a Nikon fluorescent microscope.

Purification of Recombinant CHI3L1 Fusion Protein

The full-length murine Chi3l1 coding region was amplified by PCR, and subcloned into the pEGX 4T-1 vector (GE life science, Pittsburgh, Pa.) at the NotI/BamHI restriction enzyme sites. CHI3L1 fusion protein was expressed in BL21 E. coli by 50 µM IPTG induction and purified using Gluta-thione Sepharose 4 Fast Flow kit (GE life science) according to the manufacture's instruction.

LLC Proliferation Assay and Annexin V Assay

Lewis Lung Carcinoma (LLC) cells ($5 \times 10^3$/well) were seeded in 96-wells plate with culture medium (DMEM+10% FBS+1×PSA, Invitrogen). GST or GST CHI3L1 fusion protein (final concentration 100 ng/ml) was added to the culture medium. After 72 hours, cell numbers of proliferation were counted. For apoptotic assay, LLC cells ($2 \times 10^5$/well) were seeded in 6-wells plate with culture medium (DMEM+10% FBS+1×PSA, Invitrogen). GST or GST CHI3L1 fusion protein (final concentration 100 ng/ml) was added to the culture medium. After 72 hours, the apoptotic cell population was determined by fluorescein isothiocyanate-labeled-Annexin V (FITC-annexinV) (Apoptosis Detection Kit; BD PharMingen, Bedford, Mass.). LLC cells treated with GST or GST-CHI3L1 fusion protein were harvested and washed twice with PBS. After resuspension of the cells in Annexin V-binding buffer containing FITC-conjugated Annexin V (1:20 dilution) and incubation at room temperature for 15 minutes, stained cells were analyzed by flow cytometry as soon as possible (within 1 hour).

Statistical Analysis

The data were mean values of multiple independent experiments and expressed as the mean±SD. ANOVA and Tukey's method based on log-transformed concentration level were used to evaluate the significance of the differences. The log-transformation stabilized variance and made the statistical assumptions under ANOVA and Tukey's method more plausible. ROC (Receiver Operating Characteristic) curve analysis was used to evaluate the diagnostic ability of CHI3L1, which is quantified by the area under the ROC curve (AUC). Analysis was performed using the pROC package in the R language. Statistical significance level was set at $p<0.05$. Confidence Intervals (CIs) were also constructed for all estimates. For the ROC analysis when AUC is 1, the 95% CI has both lower and upper limits of 1, because AUC=1 corresponds to total separation of two groups by CHI3L1 and the CI construction is based on the bootstrap procedure.

Example 2. Western Blot Analysis of CHI3L1 Expression in BALF of CCSP-rtTA/(TetO)$_7$-CMV-Stat3C Mice CCSP-rtTA/(TetO)$_7$-CMV-Stat3C mice is a spontaneous lung tumor animal model. In this model, Stat3C-Flag fusion protein was highly inducible by doxycycline treatment (FIG. 1A). To test if CHI3L1 is a secretory protein in this mouse model, Western blot analysis was performed in BALF of CCSP-rtTA/(TetO)$_7$-CMV-Stat3C mice. As shown in FIG. 1, the CHI3L1 protein expression level was detectable in BALF of doxycycline-untreated mice (−DOX, Lanes 1, 2, and 3) as one band at 39 kDa molecular weight. In comparison, the CHI3L1 protein expression level was increased in one of three doxycycline-treated mice without tumor (+DOX, lane 5), indicating that CHI3L1 expression was elevated prior to tumor formation, and in all four doxycycline-treated CCSP-rtTA/(TetO)$_7$-CMV-Stat3C mice with tumor (Lung cancer, lanes 7, 8, 9, and 10).

Example 3. CHI3L1 Protein Concentration in BALF and Serum from CCSP-rtTA/(TetO)$_7$-CMV-Stat3C Mice For more quantitative analysis and accurate prediction, ELISA was used to determine the CHI3L1 concentration in BALF of wild type, doxycycline-untreated, treated without tumor, and treated with tumor CCSP-rtTA/(TetO)$_7$-CMV-Stat3C mice. The average CHI3L1 concentration was 8.3±6.4 ng/ml in wild type mice, 8.8±10 ng/ml in doxycycline-untreated CCSP-rtTA/(TetO)$_7$-CMV-Stat3C mice. In comparison, the average CHI3L1 concentration was increased more than 11-fold (100.0±49.0 ng/ml, $p<0.001$) in doxycycline-treated mice without tumor, further supporting that CHI3L1 expression was elevated prior to tumor formation, and was increased more than 17-fold (151.8±67.3 ng/ml, $p<0.001$) in doxycycline-treated mice with tumor (FIG. 2, upper panel). The AUCs of the ROC curves are 1 (95% CI: 1-1, $p<0.001$) for discriminating doxycycline-treated mice with tumor vs. doxycycline-untreated mice, 1 (95% CI: 1-1, $p<0.001$) for doxycycline-treated mice without tumor vs. doxycycline-untreated mice, and 0.74 (95% CI: 0.56-0.93, $p=0.1$) for doxycycline-treated mice with tumor vs. doxycycline-treated mice without tumor.

The CHI3L1 concentration in the blood was further tested. When compared with doxycycline-untreated mice (6.2±3.7 ng/ml), the average CHI3L1 concentration was increased more than 5-fold (33.5±35.6 ng/ml, $p<0.001$) in doxycycline-treated mice without tumor (prior tumor formation), and was increased more than 26-fold (159.0±90.0 ng/ml, $p<0.001$) in doxycycline-treated mice with tumor (FIG. 2, lower panel). The AUCs of the ROC curves are 0.95 (95% CI: 0.87-1, $p<0.001$) for discriminating doxycycline-treated mice with tumor vs. doxycycline-treated without tumor mice, 1 (95% CI: 1-1, $p<0.001$) for doxycycline-treated mice with tumor vs. doxycycline-untreated mice, and 0.89 (95% CI: 0.77-1, $p<0.001$) for doxycycline-treated mice without tumor vs. doxycycline-untreated mice. This result demonstrates that increase of the CHI3L1 protein concentration in BALF and blood is associated with Stat3C-induced inflammation and lung tumor. CHI3L1 protein increase occurred prior to spontaneous lung tumor formation in the CCSP-rtTA/(TetO)$_7$-CMV-Stat3C mouse model, therefore serves as biomarkers.

Figure 3A:
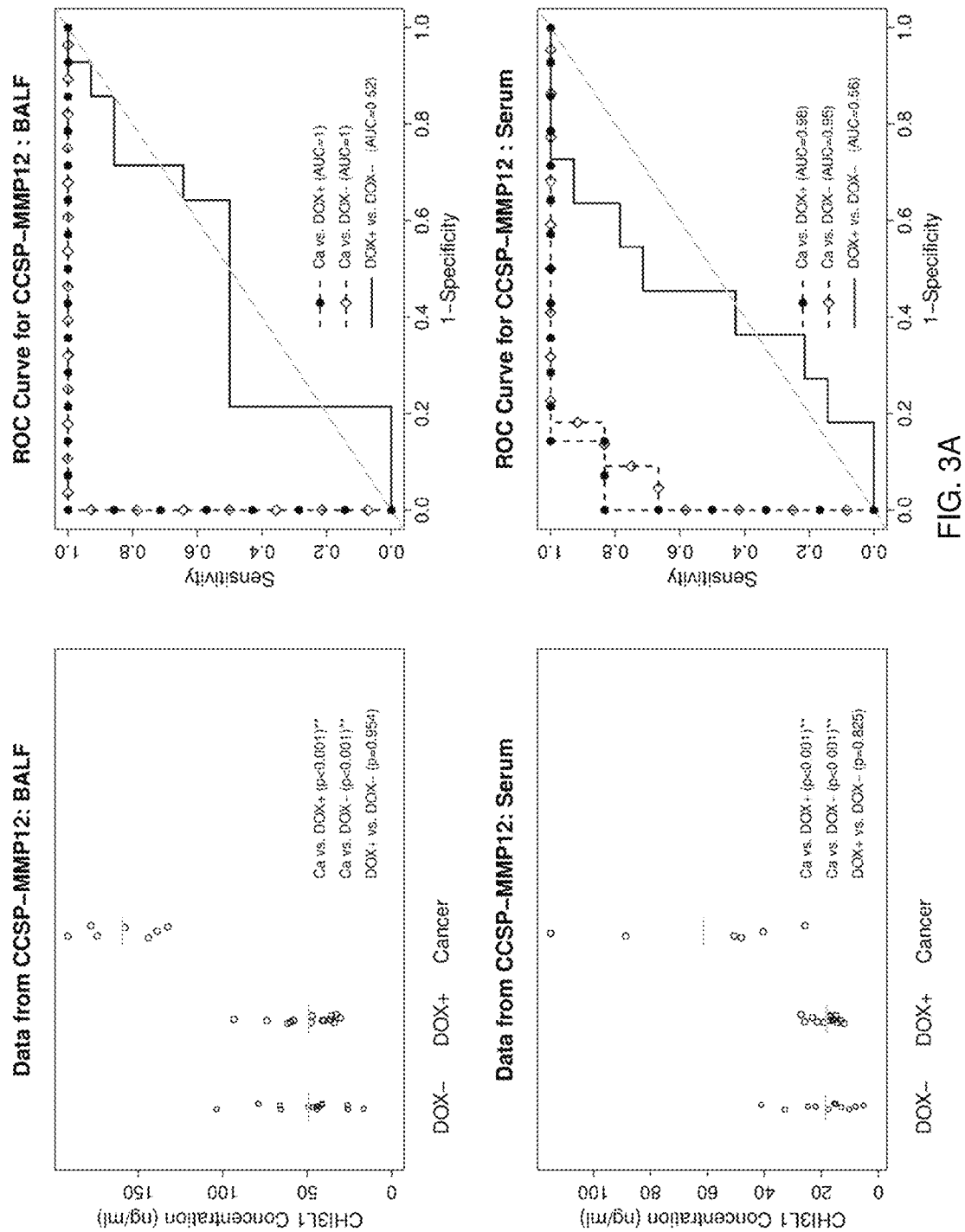
FIG. 3. ELISA analyses of CHI3L1 protein in BALF and serum of regional inflammation-induced lung tumor mice. Left: CHI3L1 protein concentrations in BALF and serum of doxycycline-treated and untreated bitransgenic mice. Right: ROC (Receiver Operating Characteristic) curve analyses to determine the area under the curve (AUC). Dox−: doxycycline-untreated mice; Dox+: doxycycline-treated mice without showing lung tumor; Cancer, doxycycline-treated mice with lung tumor. A) CCSP-rtTA/(TetO)$_7$-CMV-MMP12 mice. Mean±SD in BALF (n>7), DOX−: 49.6±22.8, DOX+: 49.4±18.1, Cancer: 159.7±22.4. Mean±SD in serum (n>7), DOX−: 18.6±10.9, DOX+: 18.2±4.6, Cancer: 61.4±33.5. The gray lines represent the mean values; B) CCSP-rtTA/(TetO)$_7$-CMV-Api6 mice. Mean±SD in BALF (n>3), DOX−: 82.4±37.1, DOX+: 93.8±23.0, Cancer: 409.8±49.2. Mean±SD in serum (n>3), DOX−: 14.0±7.2, DOX+: 30.7±43.1, Cancer: 295.2±194.0. The gray lines represent the mean values.

Example 4. ChI3L1 Protein Concentration in BALF and Serum of Regional Inflammation-Induced Lung Tumor Animal Models To test if secretory CHI3L1 protein is up-regulated in a broader application, other inflammation-induced spontaneous lung tumor mouse models were tested. Matrix metalloproteinase 12 (MMP12) is a smoking-induced matrix metalloproteinase. Over-expression of MMP12 in lung alveolar type II epithelial cells induced local inflammation, emphysema and lung tumor. In the CCSP-rtTA/(TetO)$_7$-CMV-MMP12 spontaneous lung tumor mouse model, the average CHI3L1 concentration in BALF of doxycycline-treated mice with tumor was 3-fold higher (159.7±22.4 ng/ml) compared with that in BALF of doxycycline-untreated mice (49.6±22.8 ng/ml, p<0.001, FIG. 3A, upper left panel). There was no significant difference between doxycycline-treated mice without tumor (49.4±18.1 ng/ml, p=0.954) and doxycycline-untreated mice. A similar result was observed in the serum of MMP12-induced tumor mice (FIG. 3A, lower left panel). ROC analysis indicated impressive capability of CHI3L1 concentration in discriminating the tumor group with the non-tumor group and the doxycycline-untreated group. The AUCs are 1 (95% CI: 1-1, p<0.001) in doxycycline-treated group with tumor vs. treated group without tumor and in doxycycline-treated group with tumor vs. doxycycline-untreated group, and 0.52 (95% CI: 0.29-0.75, p=0.46) in doxycycline-treated group without tumor vs. dxycycline-untreated group (FIG. 3A, upper right panel). A similar result was observed in the serum of CCSP-rtTA/(TetO)$_7$-CMV-MMP12 spontaneous lung tumor mouse model (FIG. 3A, lower right panel).

Figure 3B:
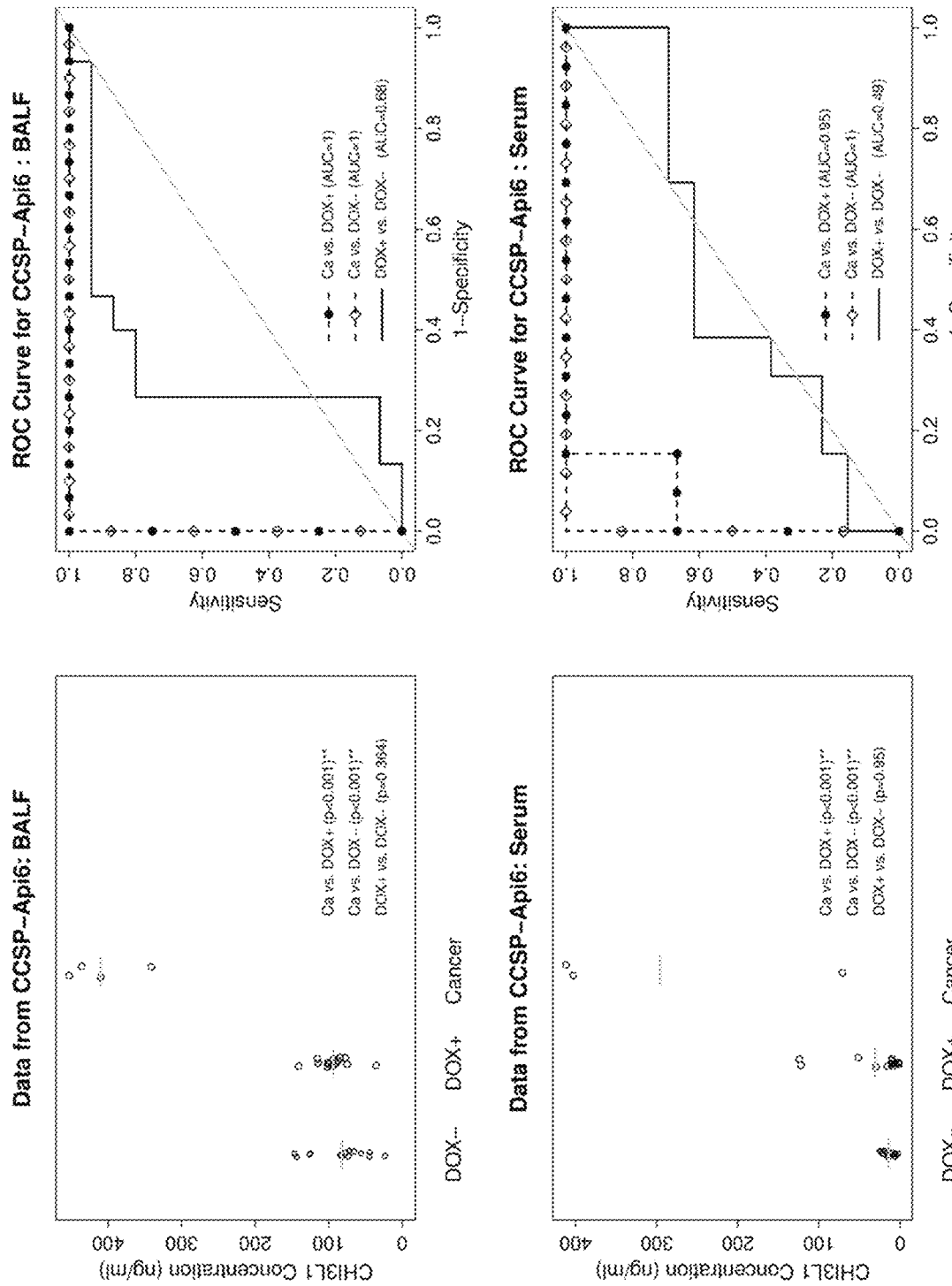

Apoptosis inhibitor 6 (Api6) is another pro-inflammatory molecule that induces inflammation and lung tumor when over-expressed in lung alveolar type II epithelial cells. In the CCSP-rtTA/(TetO)$_7$-CMV-Api6 spontaneous lung tumor mouse model, the average CHI3L1 concentration in BALF of doxycycline-treated mice with tumor was 409.8±49.2 ng/ml, compared with that in BALF of doxycycline-untreated mice (82.4±37.1 ng/ml, p<0.001, FIG. 3B, upper left panel). Similarly, there was no significant difference between doxycycline-treated mice without tumor (93.8±23.9 ng/ml, p=0.364) and doxycycline-untreated mice. A similar result was also observed in the serum of Api6-induced tumor mice (FIG. 3B, lower left panel). The AUCs from the ROC analysis are 1 (95% CI: 1-1, p<0.001) in doxycycline-treated group with tumor vs. doxycycline-treated group without tumor and in doxycycline-treated group with tumor vs. doxycycline-untreated group, and 0.68 (95% CI: 0.45-0.90, p=0.22) in doxycycline-treated group without tumor vs. doxycycline-untreated group (FIG. 3B, upper right panel). A similar result was also observed in the serum of CCSP-rtTA/(TetO)$_7$-CMV-Api6 spontaneous lung tumor mouse model, FIG. 3B, lower right panel).

Figure 4A:
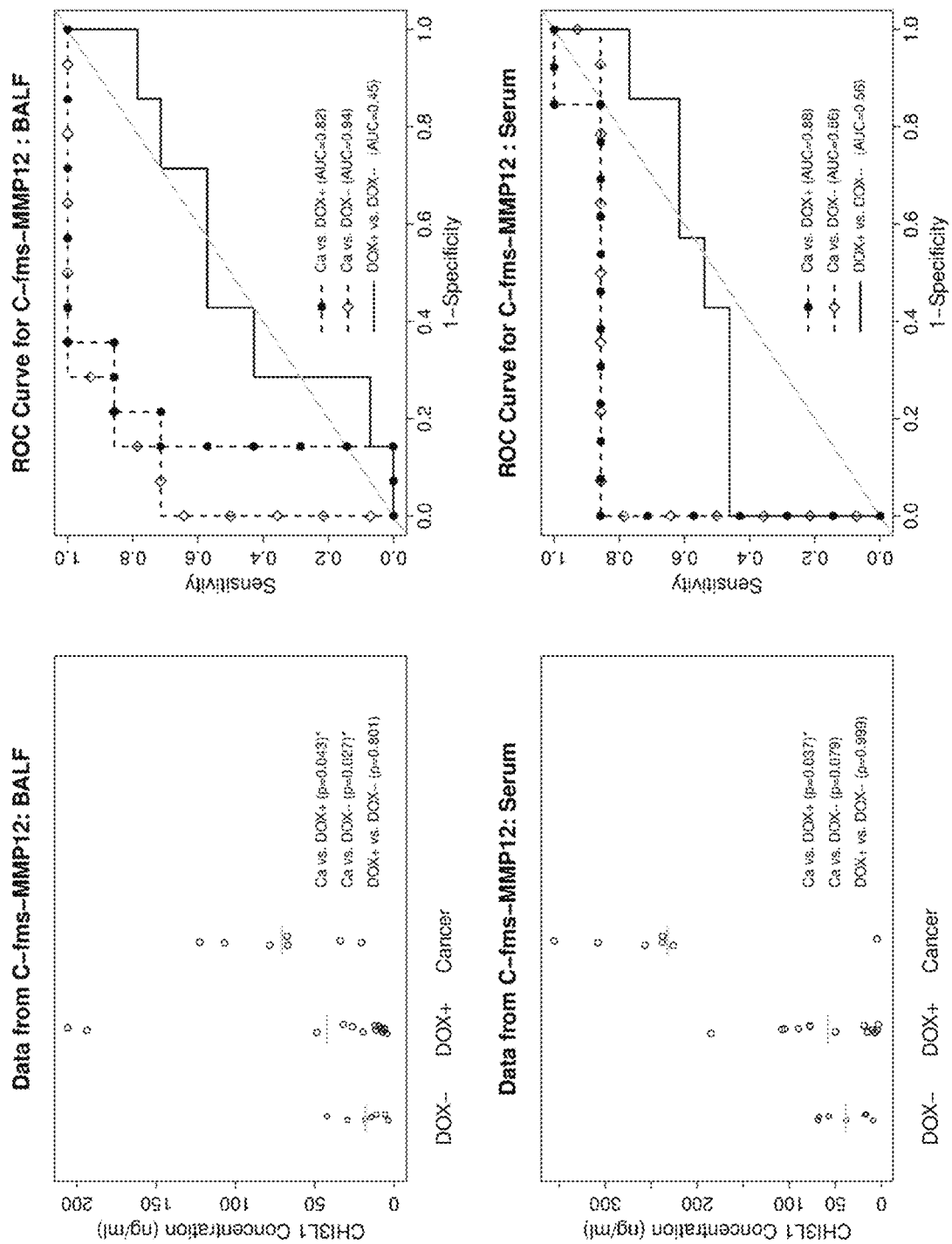
FIG. 4. ELISA analyses of CHI3L1 protein in BALF and serum of systemic inflammation-induced lung tumor mice. Left: CHI3L1 protein concentrations in BALF and serum of doxycycline-treated and untreated bitransgenic mice. Right: ROC (Receiver Operating Characteristic) curve analyses to determine the area under the curve (AUC). Dox−: doxycycline-untreated mice; Dox+: doxycycline-treated mice without showing lung tumor; Cancer, doxycycline-treated mice with lung tumor. A) c-fms-rtTA/(TetO)$_7$-CMV-MMP12 mice. Mean±SD in BALF (n>7), DOX−: 17.7±13.8, DOX+: 42.1±67.9, Cancer: 70.9±36.5. Mean±SD in serum (n>7), DOX−: 39.1±25.6, DOX+: 57.7±55.5, Cancer: 232.3±110.6. The gray lines represent the mean values; B) c-fms-rtTA/(TetO)$_7$-CMV-Api6 mice. Mean±SD in BALF (n>6), DOX−: 69.6±16.6, DOX+: 73.2±28.1, Cancer: 189.9±47.2. Mean±SD in serum (n>6), DOX−: 25.2±7.3, DOX+: 21.0±11.7, Cancer: 69.5±19.1. The gray lines represent the mean values.

Example 5. CHI3L1 Protein Concentration in BALF and Serum of Systemic Inflammation-Induced Lung Tumor Animal Models In contrast to lung regional inflammatory animal models, when MMP12 or Api6 was over-expressed in myeloid cells, systemic inflammation is initiated from malformation and malfunction of myelopoiesis from the bone marrow. Lung tumor formation was observed in both MMP12 and Api6 bitransgenic mouse models. This represents a different cellular mechanism for lung cancer formation. In the c-fms-rtTA/(TetO)$_7$-CMV-MMP12 spontaneous lung tumor mouse model, the average CHI3L1 concentration in BALF of doxycycline-treated mice with tumor (70.9±36.5 ng/ml) was 4-fold increase in comparison with that in BALF of doxycycline-untreated mice (17.7±13.8 ng/ml, p=0.027, FIG. 4A, upper left panel). Doxycycline-treated mice without tumor (42.1±67.9 ng/ml, p=0.043, FIG. 4 A) also showed the increased CHI3L1 concentration compared with doxycycline-untreated mice. A similar result was observed in the serum of c-fms-rtTA/(TetO)$_7$-CMV-MMP12 spontaneous lung tumor mouse model with tumor (FIG. 4, lower left panel), in which the average CHI3L1 concentration was more than 6 times higher in tumor mice than that of doxycycline-untreated control mice. The AUCs from the ROC analysis were 0.82 (95% CI, 0.62-1, p=0.05) in doxycycline-treated group with tumor vs. doxycycline-treated group without tumor, 0.94 (95% CI, 0.82-1, p<0.001) in doxycycline-treated group with tumor vs. doxycycline-untreated group, and 0.45 (95% CI, 0.17-0.73, p=0.57) in doxycycline-treated group without tumor vs. doxycycline-untreated group (FIG. 4A, upper right panel). Similar results were observed for serum samples of c-fms-rtTA/(tetO)$_7$-CMV-MMP12 spontaneous lung tumor mouse model (FIG. 4A, lower right panel).

Figure 4B:
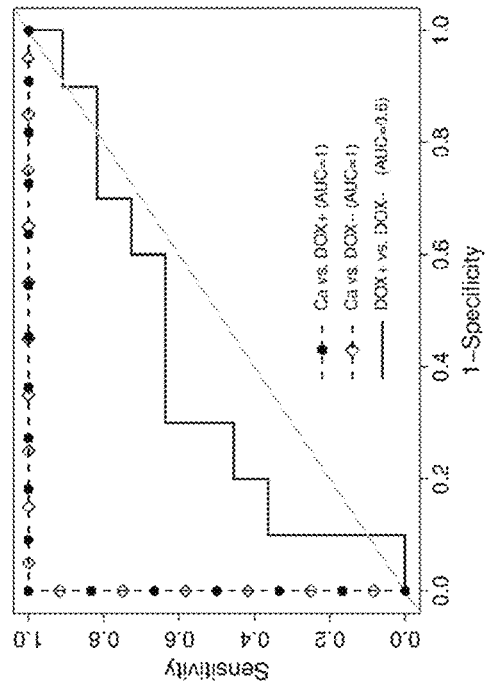
Figure 4B:
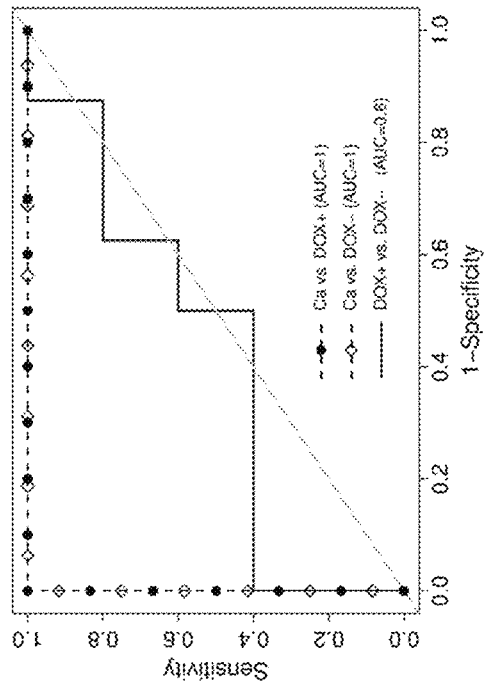
Figure 4B:
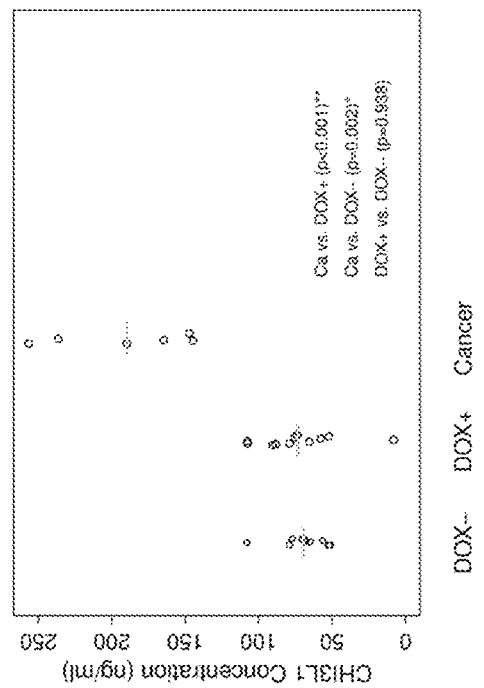
Figure 4B:
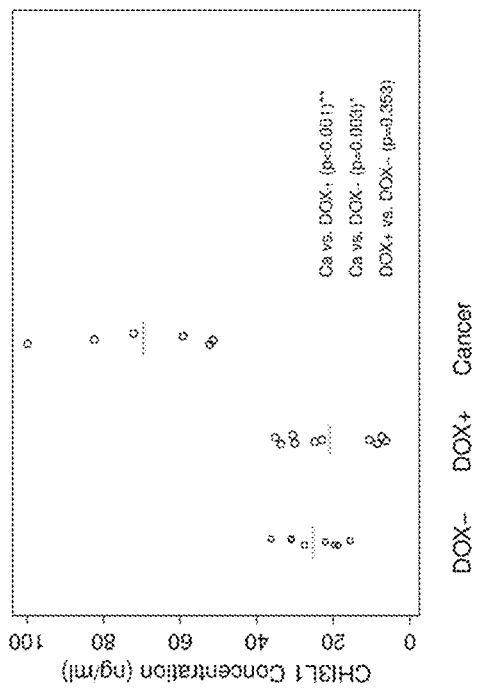

In the c-fms-rtTA/(TetO)$_7$-CMV-Api6 spontaneous lung tumor mouse model, the average CHI3L1 concentration in BALF of doxycycline-treated mice with tumor (189.6±47.2 ng/ml) was ~3-fold higher than that in BALF of doxycycline-untreated mice (69.6±16.6 pg/ml, p=0.002, FIG. 4B, upper left panel) Similarly, there was no significant difference between doxycycline-treated mice without tumor (73.2±28.1 ng/ml, p<0.001) and doxycycline-untreated mice. A similar result was also observed in the serum of Api6-induced tumor mice (FIG. 4B, lower left panel), in which the average CHI3L1 concentration was 3 times higher in tumor mice than that of doxycycline-untreated control mice. The AUCs from the ROC analysis are 1 in doxycycline-treated group with tumor vs. doxycycline-treated group without tumor, 1 in doxycycline-treated group with tumor vs. doxycycline-untreated group, and 0.6 (95% CI, 0.34-0.86, p=0.35) in doxycycline-treated group without tumor vs. untreated group (FIG. 4B, upper right panel). Similar results were observed for serum samples of c-fms-rtTA/(TetO)$_7$-CMV-Api6 spontaneous lung tumor mouse model (FIG. 4B, lower right panel).

Example 6. Lung Immunohistology

Figure 5B:
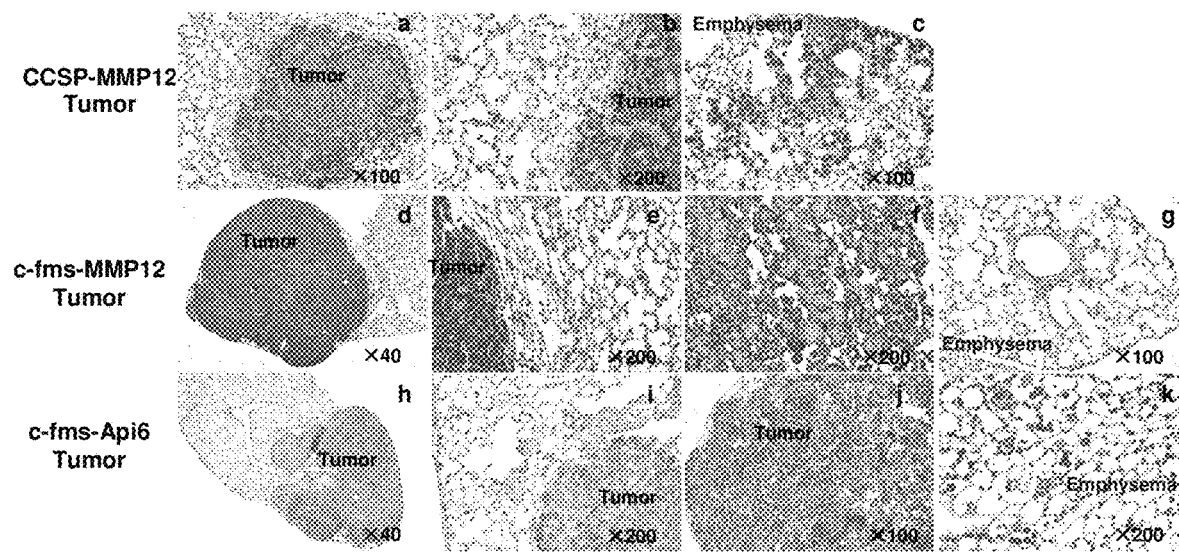

It is important to locate where CHI3L1 is expressed in the lung of above spontaneous lung tumor mouse models. Lung tissue sections from doxycycline-untreated mice, -treated without tumor, and -treated with tumor mice were immunohistochemically stained with anti-CHI3L1 antibody. In doxycycline-untreated CCSP-rtTA/(TetO)$_7$-CMV-Stat3C mice, CHI3L1 was mainly expressed in epithelial cells along the conducting airways (FIG. 5 A a), distal bronchiolar epithelial cells (FIG. 5A b), and alveolar type II epithelial cells (FIG. 5 A c) (red arrows). CHI3L1 was also expressed in alveolar macrophages. In doxycycline-treated CCSP-rtTA/(TetO)$_7$-CMV-Stat3C mice when inflammation was induced but with no tumor appearance, some areas showed tissue remodeling (FIG. 5A e) and emphysema (FIG. 5A f). Almost all infiltrated macrophages were stained positively with CHI3L1 (FIG. 5A e, green arrow). In doxycycline-treated CCSP-rtTA/(TetO)$_7$-CMV-Stat3C mice with tumor appearance, CHI3L1 expression was detected in tumor cells and surrounding macrophages (FIG. 5A g, h, i). Co-localization of CHI3L1 in alveolar macrophages was further confirmed in the lung of doxycycline-treated bitransgenic mice with anti-CHI3L1 and anti-F4/80 antibodies in immunofluorescent staining A representative result from CCSP-rtTA/(TetO)$_7$-CMV-Stat3C mice was presented in FIG. 6.

These observations were repeatable in other MMP12 and Api6-induced spontaneous lung tumor mouse models. Regardless of lung tumor initiated from alveolar type II cells or myeloid cells, CHI3L1 was over-expressed in tumor cells of these MMP12 and Api6-induced spontaneous lung tumor mouse models. Macrophages surrounding emphysema (FIG. 5B c, g, k) and tumor cells (FIG. 5B b, e, f, i) were also intensely stained by anti-CHI3L1 antibody (green arrow). This helps explain why the CHI3L1 concentration was higher in both BALF and blood of tumor mice.

Example 7. CHI3L1 Stimulation on Cancer Cells

To test if CHI3L1 possesses the stimulatory effect on lung cancer cells, recombinant CHI3L1-GST fusion protein and GST protein were prepared and purified from bacteria (FIG. 7A). Recombinant CHI3L1-GST fusion protein or control GST protein was incubated with LLC cells. CHI3L1-GST fusion protein significantly stimulated cancer cell proliferation compared with that of GST control protein (FIG. 7B). The apoptotic activity of CHI3L1-GST fusion protein treated LLC cells was reduced compared with that of GST control protein (FIG. 7C). This indicates that CHI3L1 stimulates lung cancer proliferation and growth.

Example 8. CHI3L1 Protein Concentration in the Serum from Human Lung Cancer

Approximately 30 serum samples from human patients of lung adenocarcinoma, lung squamous carcinoma and lung small cell cancer were tested by ELISA. It was found that the mouse model results translates to humans and CHI3L1 protein concentration correlates well with tumor occurrence in both regional inflammation and systemic inflammation-initiated spontaneous lung tumor mouse models.

Compared with human serum samples without any cancer (normal), the CHI3L1 protein concentration was significantly elevated in human serum samples from all categories of lung cancer patients (FIG. 8, upper panel). The AUCs are 0.83 (95% confidence interval, 0.69-0.92, P=0.005) for adenocarcinoma vs. Control, 0.87 (95% confidence interval, 0.77-0.97, P<0.001) for squamous carcinoma vs. Control, and 0.81 (95% confidence interval, 0.72-0.94, P=0.001) for small cell carcinoma vs control (FIG. 8, lower panel).

Figure 22:
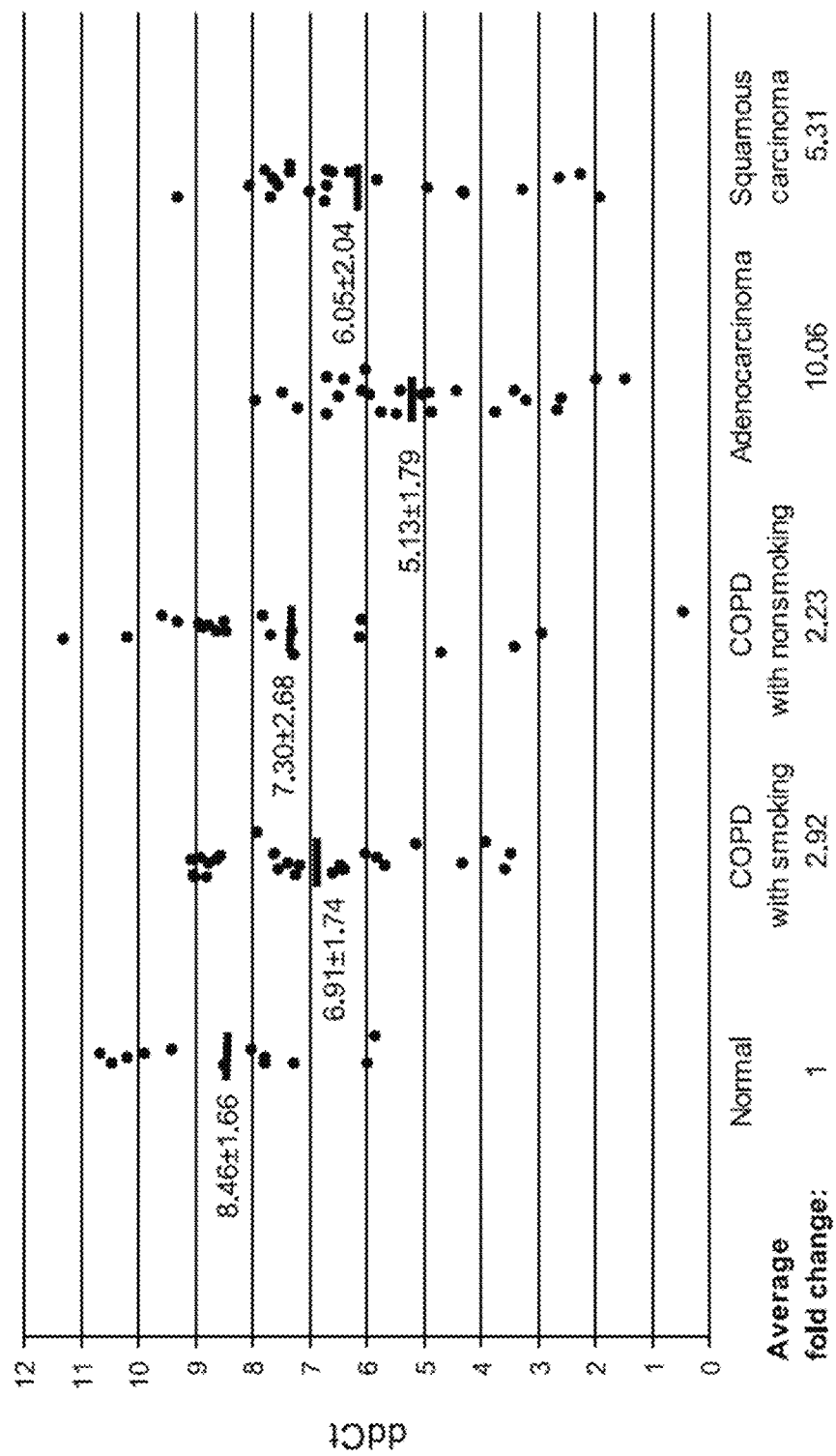
FIG. 22. Marker 14: Expression of MMP12 mRNA in human tumor and COPD was measured by Real-Time PCR and normalized by GAPDH mRNA expression.

Example 9. MMP12 Up-Regulation in Human Adenocarcinoma, Squamous Cell Carcinoma and COPD The expression levels of MMP12 mRNA in human adenocarcinomas (n=24), squamous cell carcinomas (n=22), COPD without smoking (n=21) and COPD with smoking (n=25) vs normal samples (n=12) were examined by quantitative Real-Time PCR (FIG. 22). In comparison with normal human lungs, the average of MMP12 mRNA expression levels was 10.06-fold higher in adenocarcinomas, 5.31-fold higher in squamous cell carcinomas, 2.23-fold higher in lung tissues with COPD from non-smokers and 2.92-fold higher in lung tissues with COPD from smokers.

FIG. 22 shows expression of MMP12 mRNA was measured by Real-Time PCR and normalized by GAPDH mRNA expression. Numbers in each column represent average dCt. Average fold changes were determined by $2^{(ddCt)}$, in which dCT=dCt (cancer or COPD samples)–dCt (normal human samples). Numbers on the bottom represent average fold changes compared to the normal human samples. Normal human samples were set up as one.

Stat3 upregulation was observed in the same human samples. Co-upregulation of MMP12 and Stat3 in human patients indicates that both molecules are connected and contribute to lung cancer formation.

Chronic inflammation facilitates formation of emphysema and lung cancer. MMP12 is under the control of anti-inflammatory PPARγ and its lipid hormonal ligands. Activation of PPARγ inhibits the proliferation of lung carcinoma cells. The balance and antagonism between anti-inflammatory PPARγ and pro-inflammatory IL-6/Stat3 are a determinative factor in lung cancer formation.

Example 10. Api6 Upregulation in Human COPD and Adenocarcinoma

Figure 23:
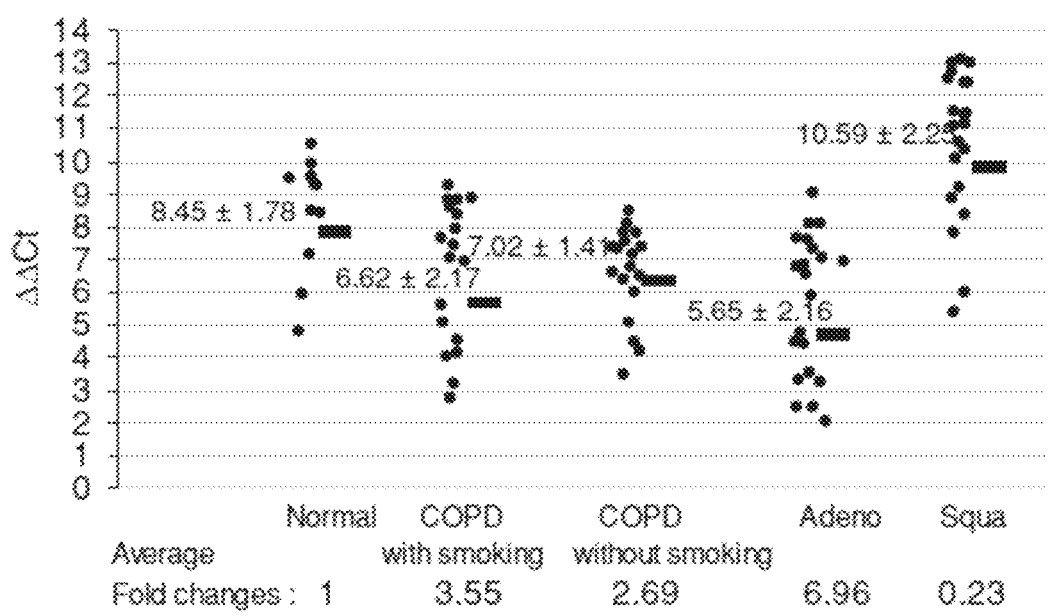
FIG. 23. Marker 15: Api6 upregulation in human tumor and COPD was measured by Real-Time PCR and normalized by GAPDH mRNA expression.
Figure 24:
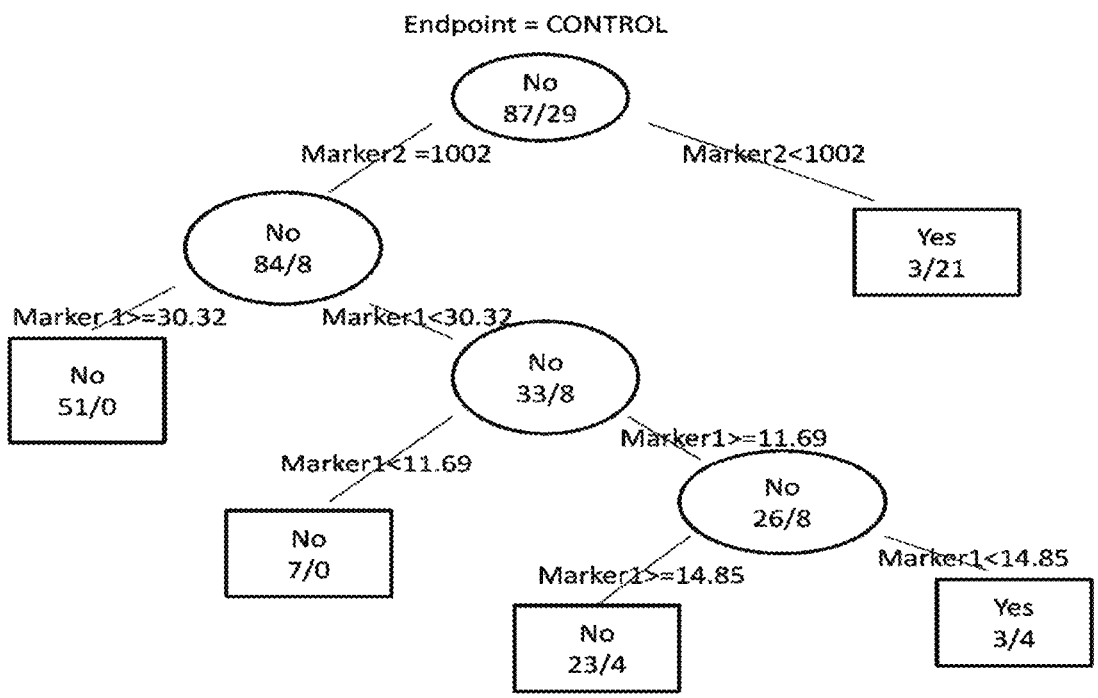
FIG. 24. Graphic depicting marker analysis example for cancer v. control
Figure 25:
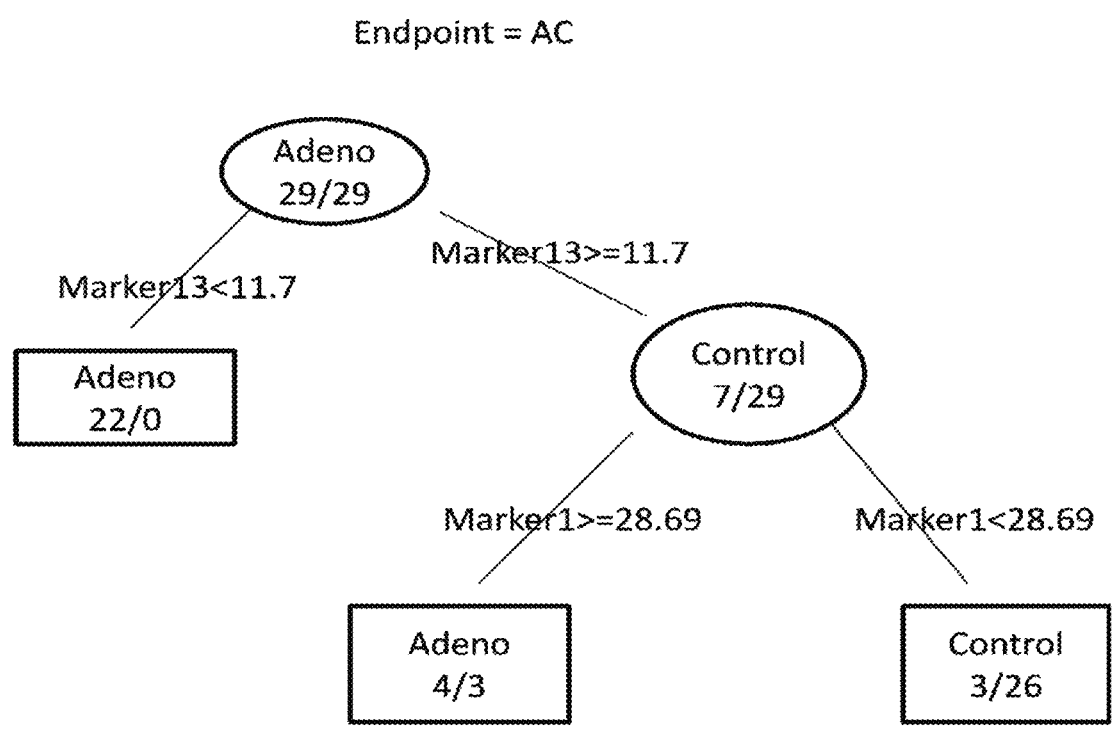
Figure 26:
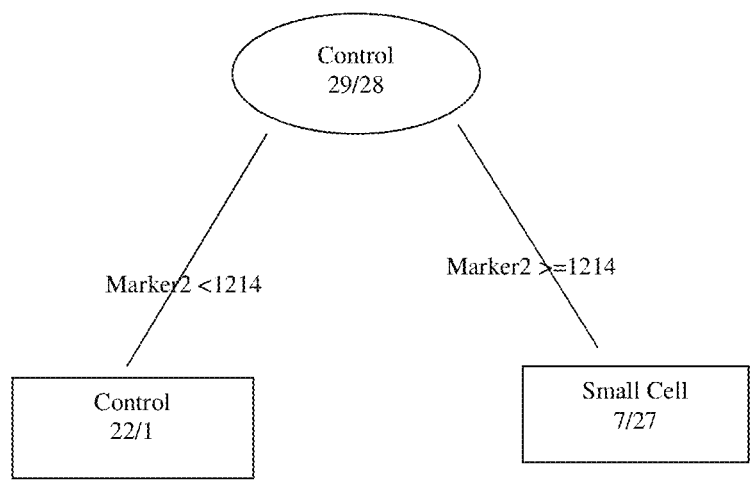
FIG. 26. Graphic depicting marker analysis example for small cell v. control.
Figure 27:
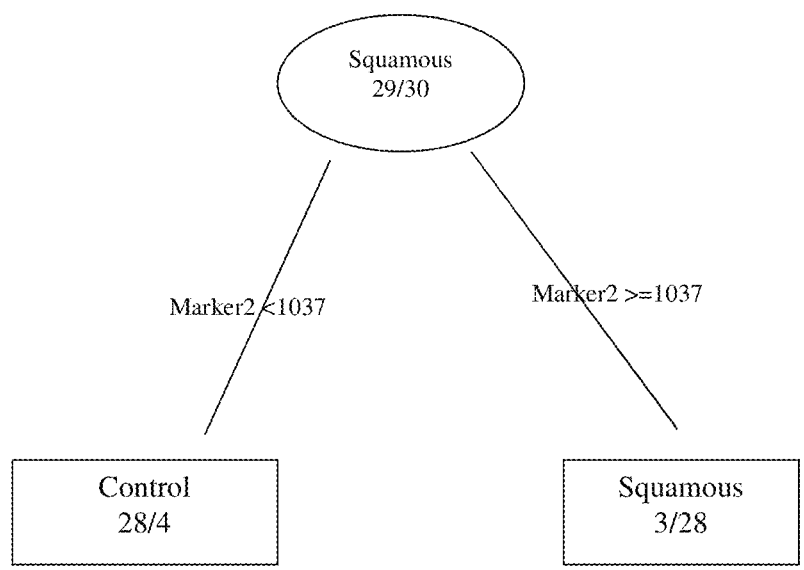
FIG. 27. Graphic depicting marker analysis example for squamous cell v. control.
Figure 28:
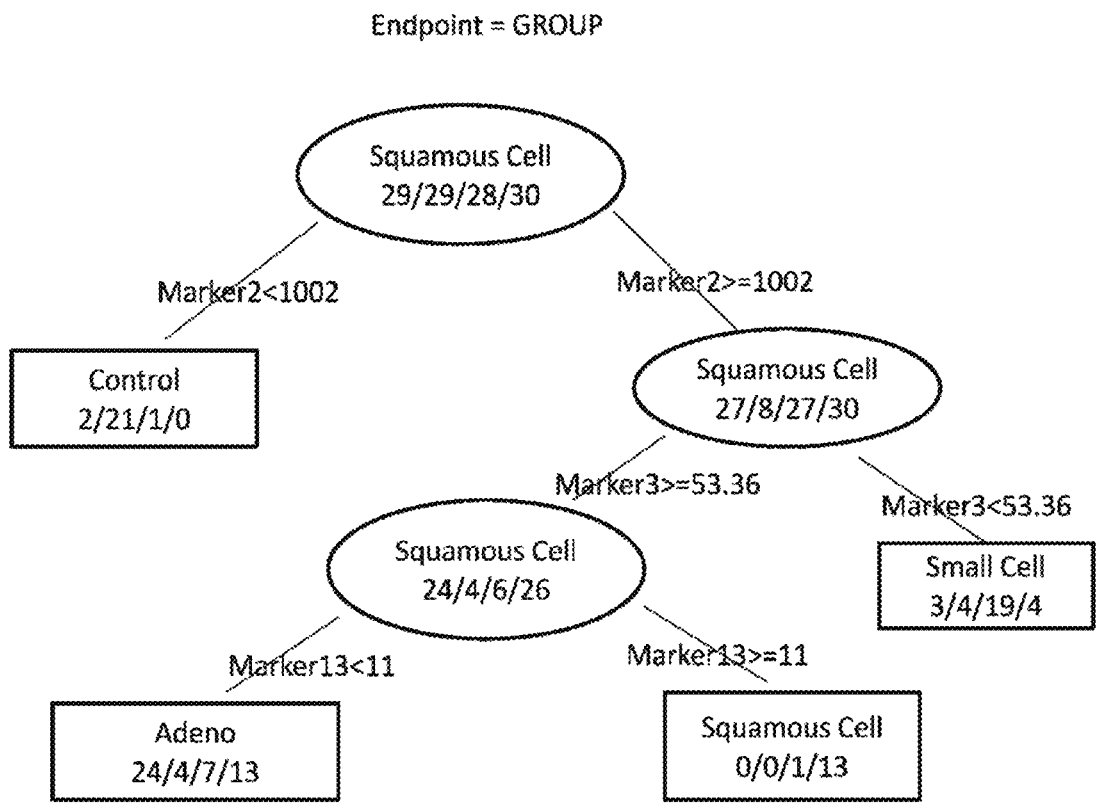
FIG. 28. Graphic depicting marker analysis example for distinguishing amongst cancers, and also distinguishing cancers from control.
Figure 29:
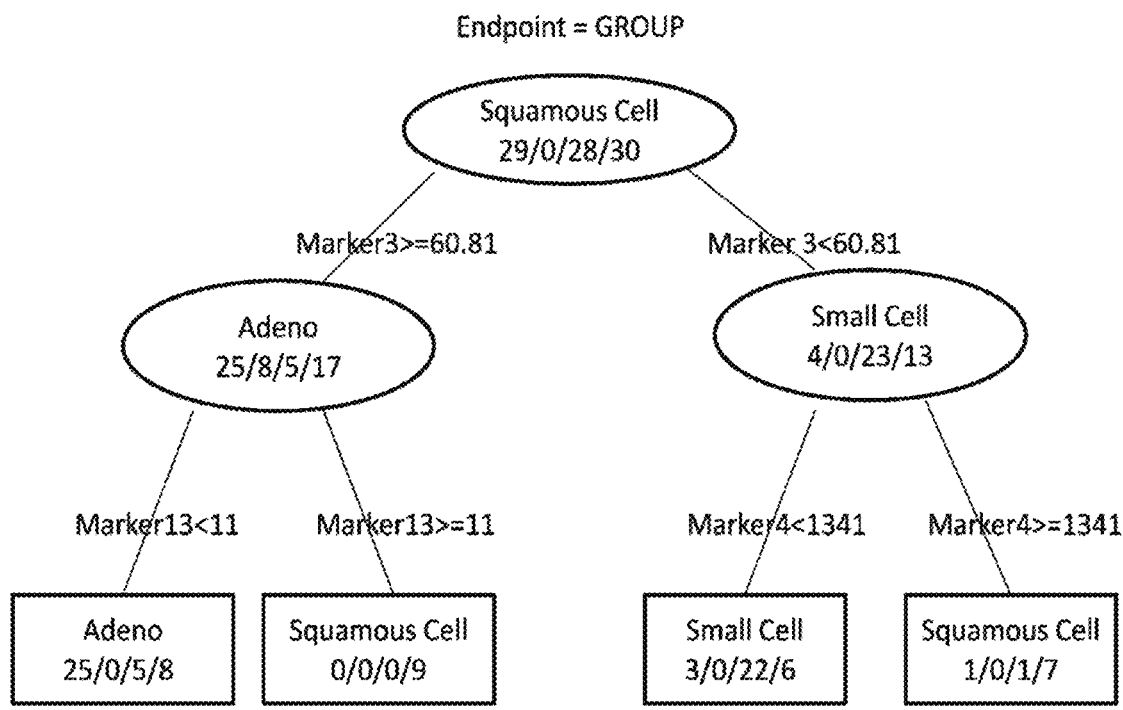
FIG. 29. Graphic depicting marker analysis example for distinguishing amongst cancers.

The expression level of Api6 mRNA in human adenocarcinomas (n=21), squamous cell carcinomas (n=20), COPD without smoking (n=18), and COPD with smoking (n=18) versus normal samples (n=12) were examined by quantitative real-time PCR (FIG. 23). In comparison with normal human lungs, the average of Api6 mRNA expression levels was 6.96-fold higher in adenocarcinomas, 2.69-fold higher in lung tissues with COPD from nonsmokers, and 3.55-fold higher in lung tissues with COPD from smokers. However, the average of Api6 mRNA expression levels was 0.23-fold lower in squamous cell carcinomas, compared with those in normal human lung groups.

FIG. 23 shows Api6 upregulation in human tumor and COPD. Real-time PCR was carried out to quantify mRNA expression levels of Api6 in human lung tissues from adenocarcinoma (Adeno), squamous cell carcinoma (Squa), and COPD patients, and normalized by GAPDH mRNA expression. Numbers in each column represent average ΔCt. Average fold changes were determined by $2^{(\Delta\Delta Ct)}$, in which ΔΔCt=ΔCt (cancer or COPD samples)–ΔCt (normal human samples). Numbers on the bottom represent average fold changes compared with the normal human samples. Normal human samples were set up as 1.

Example 11. Kits

In certain embodiments, a kit provides a first and second binding agent, at least one of which is conjugated to a polymer or is polymerizable itself and at least one detectable substance. The detectable substance may be linked to at least one of the other components of the kit, such as the first binding agent, the second binding agent, a polymer. The detectable substance may be polymerizable with the binding agent. The kit may further comprise at least one container. The kit may optionally comprise a primary antibody and instructions.

In certain embodiments, the invention provides a kit for performing immuno-histochemistry on a sample comprising a) at least one secondary antibody optionally linked to a first polymer; b) at least one tertiary antibody linked to a second polymer and a first detectable substance linked to at least one of i) the at least one tertiary antibody; ii) the first polymer; and iii) both the first polymer and the tertiary antibody; c) optionally a primary antibody; d) at least one container and optionally, instructions. The kit may further comprise a first secondary antibody linked to a first polymer and a second secondary antibody linked to a second polymer and a second detectable substance linked to at least one of a) the secondary antibody; b) the second polymer; and c) both the secondary antibody and the second polymer. In some embodiments, the first and second detectable substances are different.

Example 12. Assessing Signature of Secretory Proteins for Diagnosis of Lung Cancers in Human Subjects Methods
ELISA
The serum samples of normal human objects without cancer and lung cancer patients (adenocarcinoma, squamous cell carcinoma and small cell lung cancer) were obtained from the Biosample Repository Core Facility (BRCF) of Fox Chase Cancer Center in Philadelphia (supported by NCI). The human serum samples (22-29 in each group) were diluted to 1:100 before assay. Biomarker concentrations in human serum (50-100µ of diluted sample) were determined by Human ELISA Kits according to the manufacturer's instruction (USCN Life Science Inc, US). The protocol for an exempt study using these human tissues and blood has been approved by the IUPUI Institutional Review Committee.

Statistical Analysis

In this example, 13 markers were examined Some markers were not normally distributed. For simplicity, the distributions for all markers were compared via non-parametric methods. Kruskal-Wallis tests were done to compare all four groups overall. When significant at the 0.05 level, each tumor type was next compared to control using Wilcoxon Rank-Sum tests with a Bonferroni correction for multiple testing. Standard logistic regression techniques were used to examine the predictive value of each marker univariately. For each marker, ROC curves and c-statistics for each tumor type vs. control were generated.

To create a multivariate clinical prediction rule, CART (Classification and Regression Tree) was utilized. Tree-based techniques produce one or more tree objects that represent a series of splits from the 'root' or top of the tree. The primary methodology was the RPART method, where each split is based on finding the one predictor variable (and a given threshold of that variable) that minimizes a measure called the Gini entropy (a measure of impurity of the groups that would result from a split). As a sensitivity analyses, the inventors compare the results of the RPART method to the TREE method. In the TREE method, each split is based on finding the one predictor variable (and a given threshold of that variable) that results in the greatest change in explained deviance. Tree functions operate by doing an exhaustive search of all possible threshold values for each predictor. Once a split is made, the routine is repeated for each group separately until all deviance (or a low threshold) is explained, the entropy reducing reaches a minimum value, or there are too few samples in the remaining subset to split further.

CART models are ideal for uncovering complex dependencies among predictor variables. When you have reason to suspect there may be complex relationships among the predictor variables, suspect the variables are not normally distributed, or have many variables and don't know what to expect, a tree model is preferred over generalized linear models or linear discriminant models. RPART is preferred over TREE when there are reasonable numbers of missing data because it has a built-in rule to classify all cases. In the worst case, if it cannot classify a case, it puts it in the node with the highest frequency. TREE throws out missing data and uses only cases with data.

Example 13. Signature of Secretory Proteins for Lung Cancers Diagnosis and Monitoring These secretory biomarkers in human blood serum showed no significant differences in sex or race, though the squamous cell cancer patients did tend to have more males. When comparing sex for squamous cell, the percent male was 60% vs. 40.5% (p-value=0.06).

FIGS. 24-29 depict a graphic explanation (by CART analysis; results listed in Table 3) of how the biomarkers can be used to differentiate cancer vs control, adenocarcinomas vs control, small cell lung cancer vs control, squamous cell vs control and each type of cancer within cancer groups. Although the FIGS. 24-29 depict a sequential analysis, the analysis can also be completed simultaneously or by an alternate sequence.

For example, to identify adenocarcinomas (see FIG. 25, Endpoint AC), Marker 13 is analyzed first. If the result value<11.7 ng/ml, the sample comprises adenocarcinomas. If the result>11.7 ng/ml, the sample will be further tested by Marker 1: the result is positive for adenocarcinomas if >28.69 ng/ml and negative for adenocarcinomas if <28.69 ng/ml. In this figure, 29 out of 29 in control are >11.7 ng/ml for Marker 13, and 22 out of 29 adenocarcinomas are <11.7 ng/ml for Marker 13. Optionally, the sample may be analyzed for Marker 1. In this example, the 4 out of 7 are positive for adenocarcinomas.

To identify small cell lung cancer (FIG. 26, Endpoint SMC), Marker 2 can be analyzed. The result of >1214 ng/ml indicates positive for small cell lung cancer, and <1214 ng/ml indicates negative for small cell lung cancer.

To identify squamous cell lung cancer (FIG. 27, Endpoint SQC), Marker 2 can be analyzed. The results of >1037 ng/ml indicate positive for squamous cell lung cancer and <1038 ng/ml indicate negative for squamous cell lung cancer.

With all four groups together (FIG. 28, Endpoint GROUP), the example shows a sequential analysis: Marker 2 differentiates Control (<1002 ng/ml) and Cancers (>1002 ng/ml), followed by Marker 3, which differentiates small cell lung cancer (<53.36 ng/ml) and others (>53.36 ng/ml), and then followed by Marker 13, which differentiates adenocarcinomas (<11 ng/ml) and squamous cell lung cancer (>11 ng/ml).

Within cancer groups (FIG. 29, Endpoint GROUP), the example shows a sequential analysis: Marker 3 (>60.81 ng/ml) and then marker 13 (<11 ng/ml) identify adenocarcinomas; Marker 3 (<60.81 ng/ml) and then Marker 4 (<1341 ng/ml) identify small cell lung cancer; and Marker 3 (<60.81 ng/ml) then Marker 4 (>1341 ng/ml), or Marker 3 (>60.81 ng/ml) and then Marker 13 (>11 ng/ml) identify squamous cell lung cancer (alternative strategies may be used).

A separated data analysis by TREE method indicated Marker 2 and then 1 to differentiate cancer and control; Marker 3 to differentiate adenocarcinomas and control; Marker 2 and then 7 to differentiate small cell lung cancer and control and Marker 2 and then 13 to differentiate squamous cell lung cancer and control; Marker 3, 4, 13 and 6 to differentiate amongst cancer types.

Secretory biomarker protein concentrations in human serum were determined by enzyme-linked immunoabsorbent assay (ELISA). The area under the curve (AUC) was determined by sensitivity-specificity ROC (Receiver Operating Characteristic) curve analysis.

Marker 1: CHI3L 1—Chitinase 3-like 1;
Marker 2: TTR—Transthyretin;
Marker 3: FGb—Fibrinogen, beta polypeptide;
Marker 4: FGL 1—Fibrinogen-like protein 1;
Marker 5: GUCA2A—Guanylate cyclase activator 2A (guanylin);
Marker 6: DLK1—Delta-like 1 homolog (*Drosophila*);
Marker 7: GLUT3—Glucose Transporter 3;
Marker 8: CBLN1—Cerebellin 1;
Marker 9: ELA 1—Elastase 1, pancreatic;
Marker 10: Fga—Fibrinogen, alpha polypeptide;
Marker 11: HRG—Histidine-rich glycoprotein;

Marker 12: SHH—Sonic hedgehog homolog;
Marker 13: TMEM27—Transmembrane protein 27;
Marker 14: MMP12—Matrix-metalloproteinase 12;
Maker 15: Api6 Apoptosis inhibitor 6.

TABLE 1

Table 1 - Univariate Results

| | Distribution Shift vs Control Group p-value* | | | Area Under the ROC | | |
|---|---|---|---|---|---|---|
| | Adeno-carcinoma | Squamous Cell | Small Cell | Adeno-carcinoma | Squamous Cell | Small Cell |
| Marker 1 | <.001 | <.001 | <.001 | .83 | .87 | .80 |
| Marker 2 | <.001 | <.001 | <.001 | .96 | .995 | .98 |
| Marker 3 | <.001 | <.001 | <.001 | .998 | .97 | .84 |
| Marker 4 | <.001 | <.001 | .002 | .84 | .98 | .99 |
| Marker 5 | <.001 | <.001 | <.001 | 1.0 | .99 | .89 |
| Marker 6 | <.001 | .003 | <.001 | 1.0 | .78 | .96 |
| Marker 7 | .002 | .012 | .520 | .78 | .72 | .56 |
| Marker 8 | <.001 | .023 | .395 | .82 | .71 | .58 |
| Marker 9 | .048 | .010 | .140 | .68 | .74 | .63 |
| Marker 10 | <.001 | <.001 | <.001 | .89 | .85 | .93 |
| Marker 11 | <.001 | .170 | .870 | .86 | .62 | .52 |
| Marker 12 | .010 | .063 | .015 | .74 | .67 | .73 |
| Marker 13 | <.001 | .017 | <.001 | 1.0 | .72 | .82 |

*All overall tests were significant at the .05 level. For pair-wise Wilcoxon Rank Sum tests, compare p-value to .05/3 = .0167. Significant p-values in bold. Control group: normal human subjects.
Marker 1: CHI3L1—Chitinase 3-like 1
Marker 2: TTR—Transthyretin
Marker 3: FGb—Fibrinogen, beta polypeptide
Marker 4: FGL1—Fibrinogen-like protein 1
Marker 5: GUCA2A—Guanylate cyclase activator 2A (guanylin)
Marker 6: DLK1—Delta-like 1 homolog (*Drosophila*)
Marker 7: GLUT3—Glucose Transporter 3
Marker 8: CBLN1—Cerebellin 1
Marker 9: LA1—Elastase 1, pancreatic
Marker 10: Fga—Fibrinogen, alpha polypeptide
Marker 11: HRG—Histidine-rich glycoprotein
Marker 12: SHH—Sonic hedgehog homolog
Marker 13: TMEM27—Transmembrane protein 27

Table 1: When comparing central tendencies among the four groups (Table 1), Markers 1, 2, 3, 4, 5, 6, and 10 all showed significant differences between each tumor type and control. For the other markers, non-significant differences were seen mostly in either squamous cell, small cell, or both. The areas under the ROCs are also presented in Table 1 and display similar patterns. The lowest areas are for squamous cell and/or small cell in Markers 7-13.

TABLE 2

Table 2 - CART Results using all available data

| | n | #correctly classified | #misclassified | Error rate for RPART | Markers using Tree | Error Rate for TREE |
|---|---|---|---|---|---|---|
| Cancer vs Control | | | | | | |
| 2 splits - Marker 2 and Marker 3 | | | | | M5, 9, 2 | |
| Cancer | 87 | 81 | 6 | | | |
| Control | 29 | 22 | 7 | | | |
| | 116 | 103 | 13 | 11.2% | | 4.2% |
| Adeno vs Control | | | | | | |
| 1 split - Marker 5 | | | | | M3 | |
| Adenocarcinoma | 29 | 29 | 0 | | | |
| Control | 29 | 22 | 7 | | | |
| | 58 | 51 | 7 | 12.1% | | 0.0% |
| Small Cell vs Control | | | | | | |
| 3 split - Marker 2 | | | | | M2 and 7 | |
| Small Cell | 28 | 27 | 1 | | | |
| Control | 29 | 19 | 10 | | | |
| | 57 | 36 | 11 | 19.3% | | 2.7% |
| Squamous Cell vs Control | | | | | | |
| 1 split - Marker 2 | | | | | M5 | |
| Squamous Cell | 30 | 26 | 4 | | | |
| Control | 29 | 26 | 3 | | | |
| | 59 | 52 | 7 | 11.9% | | 0% |

TABLE 2-continued

Table 2 - CART Results using all available data

| | n | #correctly classified | #misclassified | Error rate for RPART | Markers using Tree | Error Rate for TREE |
|---|---|---|---|---|---|---|
| Using all 4 groups | | | | | | |
| 4 splits - Markers 2, 3, 13, 10 | | | | | M3, 2, 13, 6, 7, 5 | |
| Adenocarcinoma | 29 | 23 | 6 (as 2 ctl, 4 sm) | | | |
| Control | 29 | 22 | 7 (as 1 adeno, 6 sm) | | | |
| Small Cell | 28 | 18 | 10 (as 6 adeno, 3 ctl, 1 sq) | | | |
| Squamous Cell | 30 | 13 | 17 (as 10 adeno, 3 ctl, 4 sm) | | | |
| | 116 | 76 | 40 | 34.5% | | 14.1% |
| Cancer Only | | | | | | |
| 5 splits - Markers 3, 13, 4, 12, 1 | | | | | M3, 4, 13, 6 | |
| Adenocarcinoma | 29 | 25 | 4 (4 sq) | | | |
| Small Cell | 28 | 20 | 8 (7 acteno, 1 sq) | | | |
| Squamous Cell | 30 | 21 | 9 (8 adeno, 1 sm) | | | |
| | 87 | 66 | 21 | 24.1% | | 16.1% |

Table 2: To select biomarkers that can distinguish different types of lung cancers, the RPART method was used. Markers 2 and 3 were chosen to distinguish between cancer and control (misclassification=11.2%). When looking within the cancer samples only, Marker 3, 13, 4, 12 and 1 were chosen (misclassification rate=24.1%). For the TREE method, only the complete cases are used (n=71 out of 116 possible=61%). Relevant markers are shown in Table 2 Similar markers arise with both methods although Marker 5 comes up more often in the TREE method than RPART. The error rates are much lower with the TREE method, but the inventors are also throwing out 39% of the data. There were no differences in age, sex, or race between those with complete data and those who had a least one missing marker value.

TABLE 3

Table 3 - CART Results using all available data

| | n | #correctly classified | #misclassified | Error rate for RPART | Markers using Tree | Error Rate for TREE |
|---|---|---|---|---|---|---|
| Cancer vs Control | | | | | | |
| 3 splits - Marker 2 and Marker 1 | | | | | M2 and 1 | |
| Cancer | 87 | 81 | 6 | | | |
| Control | 29 | 25 | 4 | | | |
| | 116 | 106 | 10 | 8.6% | | 4% |
| Adeno vs Control | | | | | | |
| 2 splits - Marker 13 and Marker 1 | | | | | M3 | |
| Adenocarcinoma | 29 | 26 | 3 | | | |
| Control | 29 | 26 | 3 | | | |
| | 58 | 52 | 6 | 10.3% | | 0% |
| Small Cell vs Control | | | | | | |
| 3 split - Marker 2* | | | | | M2 and 7 | |
| Small Cell | 28 | 27 | 1 | | | |
| Control | 29 | 22 | 7 | | | |
| | 57 | 49 | 8 | 14.0% | | 2.7% |
| Squamous Cell vs Control | | | | | | |
| 1 split - Marker 2 | | | | | M2 and 13 | |
| Squamous Cell | 30 | 26 | 4 | | | |
| Control | 29 | 26 | 3 | | | |
| | 59 | 52 | 7 | 11.9% | | 3.2% |

TABLE 3-continued

Table 3 - CART Results using all available data

| | n | #correctly classified | #misclassified | Error rate for RPART | Markers using Tree | Error Rate for TREE |
|---|---|---|---|---|---|---|
| Using all 4 groups | | | | | | |
| 3 splits - Markers 2, 3, and 13 | | | | | M3, 2, 13, 6, 7, 4 | |
| Adenocarcinoma | 29 | 24 | 5 (2 ctrl, 3 sm) | | | |
| Control | 29 | 21 | 8 (as 4 adeno, 4 sm) | | | |
| Small Cell | 28 | 19 | 9 (1 ctrl, 7 adeno, 1 sq) | | | |
| Squamous Cell | 30 | 13 | 17 (13 adeno, 4 sm) | | | |
| | 116 | 77 | 39 | 33.6% | | 14% |
| Cancer Only | | | | | | |
| 3 splits - Markers 3, 11, and 4 | | | | | M3, 4, 13, 6 | |
| Adenocarcinoma | 29 | 25 | 4 (3 sm, 1 sq) | | | |
| Small Cell | 28 | 22 | 6 (5 acteno, 1 sq) | | | |
| Squamous Cell | 30 | 16 | 14 (8 adeno, 6 sm) | | | |
| | 87 | 63 | 24 | 27.5% | | 16% |

*the next step would be to add Marker 1. error rate would be 10.5%

Table 3: An alternative strategy (different secretory biomarkers, omitting marker 5) was used to distinguish different types of lung cancers using a different set of secretory biomarkers. The analysis was similar to that outlined in Table 2. Markers 2 and 1 were chosen to distinguish between cancer and control (misclassification=8.6%). When looking within the cancer samples only, Marker 3, 11, and 4 were chosen (misclassification rate=27.6%). For the TREE method, only the complete cases are used (n=71 out of 116 possible=61%). Relevant markers are shown in Table 3. Similar markers arise with both methods (except for Adenocarinoma vs. control). The error rates are much lower with the TREE method, but 39% of the data remains unused. There were no differences in age, sex, or race between those with complete data and those who had a least one missing marker value.

Table 4 shows selected serum biomarker levels for fifteen markers useful in stratifying samples. Measured values in a test sample can be compared with the listed values to assign the sample to, or exclude it from, a diagnostic classification for lung disease. Values are listed in ng/mL unless otherwise specified. Listed values are averages. The standard deviation (SD) is provided.

TABLE 4

Serum biomarker levels (ng/mL)

| Protein | Marker # | Normal | Adeno | Squamous | Small Cell |
|---|---|---|---|---|---|
| CHI3L 1 | 1 | 17.32 | 66.89 | 69.33 | 56.27 |
| | | SD: 7.97 | SD: 65.90 | SD: 70.23 | SD: 59.92 |
| TTR | 2 | 741.83 | 1337.88 | 1645.72 | 1958.69 |
| | | SD: 195.69 | SD: 382.31 | SD: 475.10 | SD: 524.97 |
| FGb | 3 | 41.00 | 70.05 | 61.70 | 49.66 |
| | | SD: 6.25 | SD: 6.76 | SD: 8.45 | SD: 7.11 |
| FGL1 | 4 | 461.62 | 2266.85 | 1644.44 | 837.93 |
| | | SD: 317.69 | SD: 815.91 | SD: 549.17 | SD: 358.05 |
| GUCA2A | 5 | 49.00 | 2429.21 | 718.92 | 198.72 |
| | | SD: 48.00 | SD: 1857.59 | SD: 515.87 | SD: 148.23 |
| DLK1 | 6 | 20.23 | 25.97 | 22.35 | 24.73 |
| | | SD: 1.46 | SD: 2.60 | SD: 2.39 | SD: 4.84 |
| GLUT3 | 7 | 19.63 | 144.07 | 88.29 | 41.37 |
| | | SD: 8.55 | SD: 285.26 | SD: 143.54 | SD: 65.64 |
| CBLN1 | 8 | 5.19 | 8.33 | 12.26 | 4.79 |
| | | SD: 2.92 | SD: 8.61 | SD: 24.24 | SD: 1.01 |
| ELA1 | 9 | 16.50 | 19.63 | 25.54 | 23.28 |
| | | SD: 17.23 | SD: 11.99 | SD: 21.19 | SD: 19.99 |
| Fga | 10 | 68.54 | 72.78 | 72.59 | 73.68 |
| | | SD: 3.15 | SD: 1.97 | SD: 2.13 | SD: 1.97 |
| HRG | 11 | 577.61 | 694.98 | 609.64 | 575.00 |
| | | SD: 81.65 | SD: 62.75 | SD: 64.99 | SD: 72.18 |
| SHH | 12 | 4.26 | 3.25 | 8.59 | 4.73 |
| | | SD: 2.86 | SD: 0.73 | SD: 13.79 | SD: 2.45 |
| TMEM27 | 13 | 14.54 | 9.48 | 13.16 | 11.49 |
| | | SD: 1.81 | SD: 0.89 | SD: 4.39 | SD: 2.67 |

TABLE 5

Relative biomarker mRNA expression (fold change relative to normal), all values are upregulated unless shown in parentheses.

| Protein | Marker # | Normal | Adeno | Squamous | COPD-nonsmoker | COPD-smoker |
|---|---|---|---|---|---|---|
| MMP12 | 14 | 1 | 10.06 | 5.31 | 2.23 | 2.92 |
| Api6 | 15 | 1 | 6.96 | (0.23) | 2.69 | 3.55 |

While the present invention has been described in terms of particular embodiments and examples, it will be appreciated that the spirit and scope of the invention is not limited to those embodiments, but extends to the various modifications and equivalents as defined in the appended claims.

What is claimed is:

1. A method to identify a lung cancer patient as having squamous cell lung cancer, the method comprising:
   detecting three protein levels in a biological sample from the patient, where the three proteins are TTR, FGb, and TMEM27;
   identifying the lung cancer as squamous cell lung cancer where the level of TTR in the sample is greater than 1002 ng/ml, the level of FGb in the sample is greater than 53.36 ng/ml; and the level of TMEM27 in the sample is greater than 11 ng/ml; and,
   administering a chemotherapy to the patient to treat the squamous cell lung cancer.

2. A method according to claim 1, where the step of administering a chemotherapy to the patient having squamous cell lung cancer is administering carboplatin to the patient.

3. A method to identify a lung cancer patient as having small cell lung cancer, the method comprising:
   detecting three protein levels in a biological sample from the patient, where the three proteins are TTR, FGb, and TMEM27;
   identifying the lung cancer as small cell lung cancer where the level of TTR in the sample is greater than 1002 ng/ml and the level of FGb in the sample is less than 53.36 ng/ml; and,
   administering a chemotherapy to the patient to treat the small cell lung cancer.

4. A method according to claim 3, where the step of administering a chemotherapy to the patient having small cell lung cancer is administering cisplatin to the patient.

5. A method to identify a lung cancer patient as having adenocarcinoma lung cancer, the method comprising:
   detecting three protein levels in a biological sample from the patient, where the three proteins are TTR, FGb, and TMEM27;
   identifying the lung cancer as adenocarcinoma lung cancer where the level of TTR in the sample is greater than 1002 ng/ml, the level of FGb in the sample is greater than 53.36 ng/ml; and the level of TMEM27 in the sample is less than 11 ng/ml; and,
   administering a chemotherapy to the patient to treat the adenocarcinoma lung cancer.

6. A method according to claim 5, where the step of administering a chemotherapy to the patient having adenocarcinoma is administering paclitaxel to the patient.

7. A method to identify a lung cancer patient as having adenocarcinoma lung cancer, the method comprising:
   detecting three protein levels in a biological sample from the patient, where the three proteins are FGL1, FGb and TMEM27;
   identifying the lung cancer as adenocarcinoma lung cancer where the level of FGb in the sample is greater than 60.81 ng/ml and the level of TMEM27 in the sample is less than 11 ng/ml; and,
   administering a chemotherapy to the patient to treat the adenocarcinoma lung cancer.

8. A method to identify a lung cancer patient as having small cell lung cancer, the method comprising:
   detecting three protein levels in a biological sample from the patient, where the three proteins are FGL1, FGb and TMEM27;
   identifying the lung cancer as small cell lung cancer where the level of FGL1 in the sample is less than 1341 ng/ml and the level of FGb in the sample is less than 60.81 ng/ml; and,
   administering a chemotherapy to the patient to treat the small cell lung cancer.

9. A method to identify a lung cancer patient as having squamous cell lung cancer, the method comprising:
   detecting three protein levels in a biological sample from the patient, where the three proteins are FGL1, FGb and TMEM27;
   identifying the lung cancer as squamous cell lung cancer where the level of FGL1 in the sample is greater than 1341 ng/ml and the level of TMEM27 in the sample is greater than 11 ng/ml; and,
   administering a chemotherapy to the patient to treat the squamous cell lung cancer.

* * * * *